US008955557B2

(12) United States Patent
Romano et al.

(10) Patent No.: US 8,955,557 B2
(45) Date of Patent: Feb. 17, 2015

(54) ENVIRONMENTAL NUCHAIN ENTERPRISE RESOURCE PLANNING METHOD AND APPARATUS

(75) Inventors: Jack W. Romano, Kirkland, WA (US); Adam L. Smith, Palm Desert, CA (US)

(73) Assignee: Medindica-Pak, Inc., Kirkland, WA (US)

(*) Notice: Subject to any disclaimer, the term of this patent is extended or adjusted under 35 U.S.C. 154(b) by 959 days.

(21) Appl. No.: 13/068,012

(22) Filed: Apr. 29, 2011

(65) Prior Publication Data

US 2011/0277849 A1 Nov. 17, 2011

Related U.S. Application Data

(60) Provisional application No. 61/395,346, filed on May 12, 2010.

(51) Int. Cl.
*A61M 1/00* (2006.01)

(52) U.S. Cl.
CPC ............ *A61M 1/0001* (2013.01); *A61M 1/0005* (2013.01); *A61M 1/0017* (2014.02)
USPC .................................. 141/8; 141/65; 604/319

(58) Field of Classification Search
CPC A61M 1/0001; A61M 1/0005; A61M 1/0017
USPC .............................. 141/4, 8, 65; 604/317, 319
See application file for complete search history.

(56) References Cited

U.S. PATENT DOCUMENTS

| | | |
|---|---|---|
| 3,032,037 A | 5/1962 | Huber |
| 3,661,143 A | 5/1972 | Henkin |
| 4,178,976 A | 12/1979 | Weiler |
| 4,388,922 A | 6/1983 | Telang |
| 4,397,643 A | 8/1983 | Rygiel |
| 4,620,846 A | 11/1986 | Goldberg et al. |
| 4,886,504 A | 12/1989 | Arvidson |
| 4,976,707 A | 12/1990 | Bodicki |
| 5,269,924 A | 12/1993 | Rochat |
| 5,364,384 A | 11/1994 | Grabenkort et al. |
| 5,382,244 A | 1/1995 | Telang |
| 5,514,123 A | 5/1996 | Adolf |
| 5,586,973 A | 12/1996 | Lemaire et al. |
| 5,752,234 A * | 5/1998 | Withers ........................... 705/2 |
| 5,899,349 A | 5/1999 | Moore |
| 6,318,417 B1 | 11/2001 | Davis |
| 6,942,123 B2 | 9/2005 | Wertenberger |
| 7,185,681 B2 | 3/2007 | Romano |
| 7,329,250 B2 | 2/2008 | Romano et al. |
| 7,798,181 B2 | 9/2010 | Romano |
| 7,854,729 B2 | 12/2010 | Romano et al. |
| 7,931,629 B2 | 4/2011 | Romano |
| 8,118,795 B2 * | 2/2012 | Romano et al. ............... 604/318 |
| 8,137,329 B2 * | 3/2012 | Romano et al. ............... 604/319 |

(Continued)

*Primary Examiner* — Nicolas A Arnett

(57) ABSTRACT

NuChain supply chain and disposal chain apparatus are created by NuPurposing containers and conditioning and transforming such containers from fluent material delivery containers into waste collection containers realizes operational efficiency. Novel structural features of waste collection systems allows bottle docking for the ingress of collection material into fluent material distribution containers as well as operation as a non-bottle docking waste collection system. The application moving canister and lid pillars closer together respectively operates to contain a force being drawn away from the collection system by sealing the system. The application moving other canister and lid pillars closer together operates to unseal the system.

39 Claims, 34 Drawing Sheets

(56) References Cited

U.S. PATENT DOCUMENTS

| | | | |
|---|---|---|---|
| 8,506,540 B2* | 8/2013 | Romano et al. | 604/319 |
| 8,529,533 B2* | 9/2013 | Romano et al. | 604/319 |
| 8,540,689 B2* | 9/2013 | Romano et al. | 604/319 |
| 8,561,653 B2* | 10/2013 | Romano | 141/9 |
| 2002/0128584 A1 | 9/2002 | Brown et al. | |
| 2002/0128612 A1 | 9/2002 | Andersson | |
| 2003/0079803 A1* | 5/2003 | Romano | 141/234 |
| 2003/0132249 A1 | 7/2003 | Romano | |
| 2004/0122383 A1 | 6/2004 | Romano et al. | |
| 2004/0149348 A1 | 8/2004 | Wertenberger | |
| 2005/0215961 A1 | 9/2005 | Romano et al. | |
| 2006/0217674 A1 | 9/2006 | Romano et al. | |
| 2007/0107798 A1* | 5/2007 | Romano | 141/9 |
| 2007/0244451 A1* | 10/2007 | Romano et al. | 604/319 |
| 2008/0132855 A1 | 6/2008 | Romano et al. | |
| 2009/0057347 A1 | 3/2009 | Leys | |
| 2010/0326565 A1 | 12/2010 | Romano | |
| 2011/0118681 A1* | 5/2011 | Romano et al. | 604/319 |
| 2011/0118682 A1* | 5/2011 | Romano et al. | 604/319 |
| 2011/0282306 A1* | 11/2011 | Romano et al. | 604/318 |
| 2011/0282308 A1* | 11/2011 | Romano et al. | 604/319 |
| 2012/0109055 A1* | 5/2012 | Romano et al. | 604/93.01 |
| 2012/0109081 A1* | 5/2012 | Romano et al. | 604/290 |
| 2012/0130324 A1* | 5/2012 | Romano et al. | 604/313 |
| 2012/0130328 A1* | 5/2012 | Romano et al. | 604/319 |
| 2014/0034189 A1* | 2/2014 | Romano et al. | 141/67 |
| 2014/0034190 A1* | 2/2014 | Romano et al. | 141/67 |

\* cited by examiner

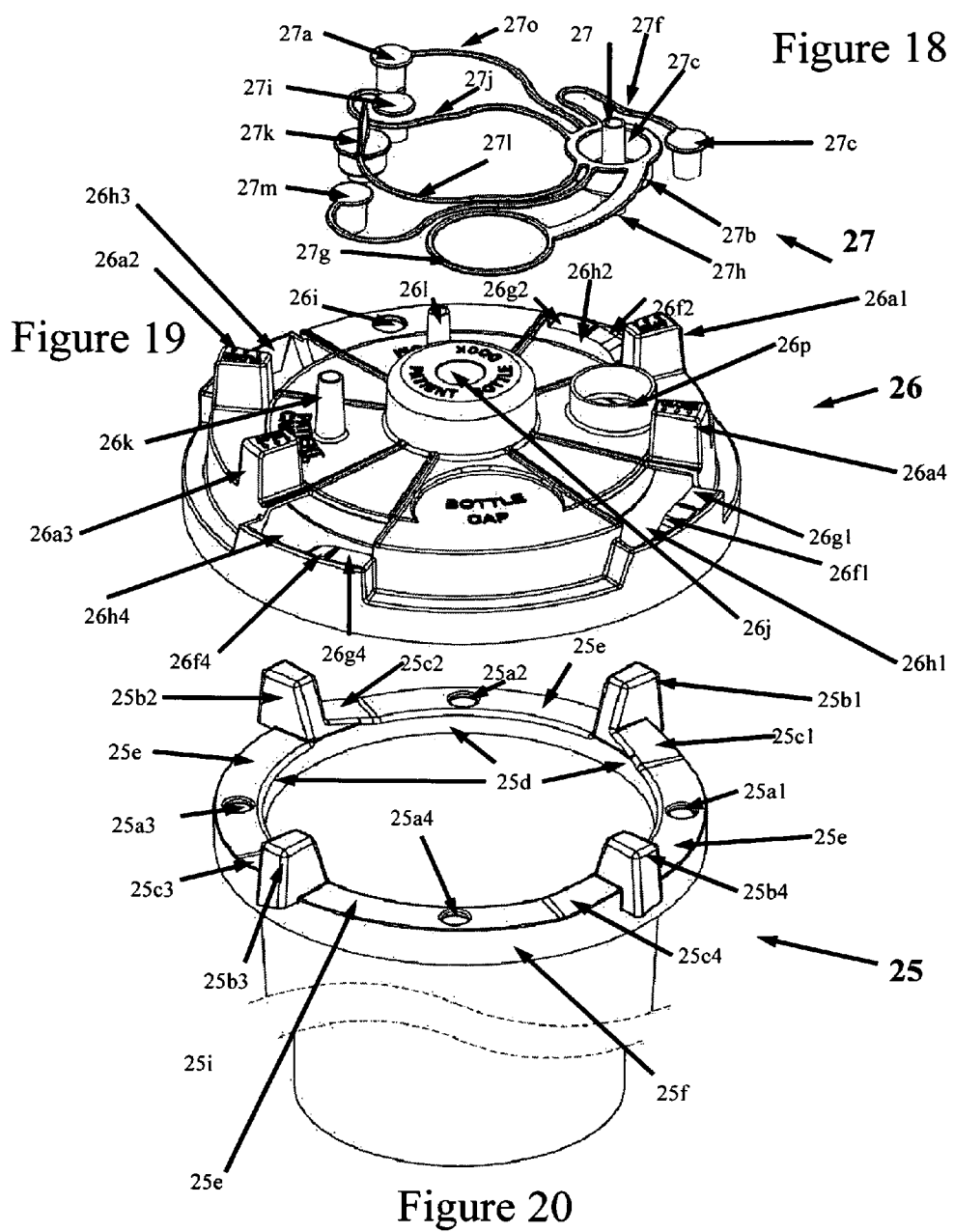

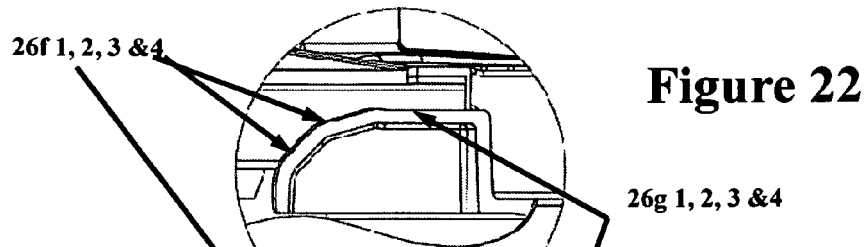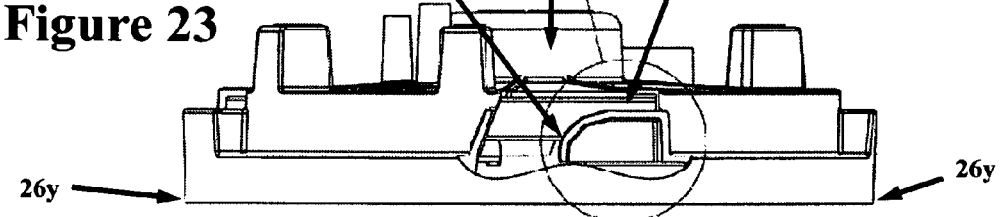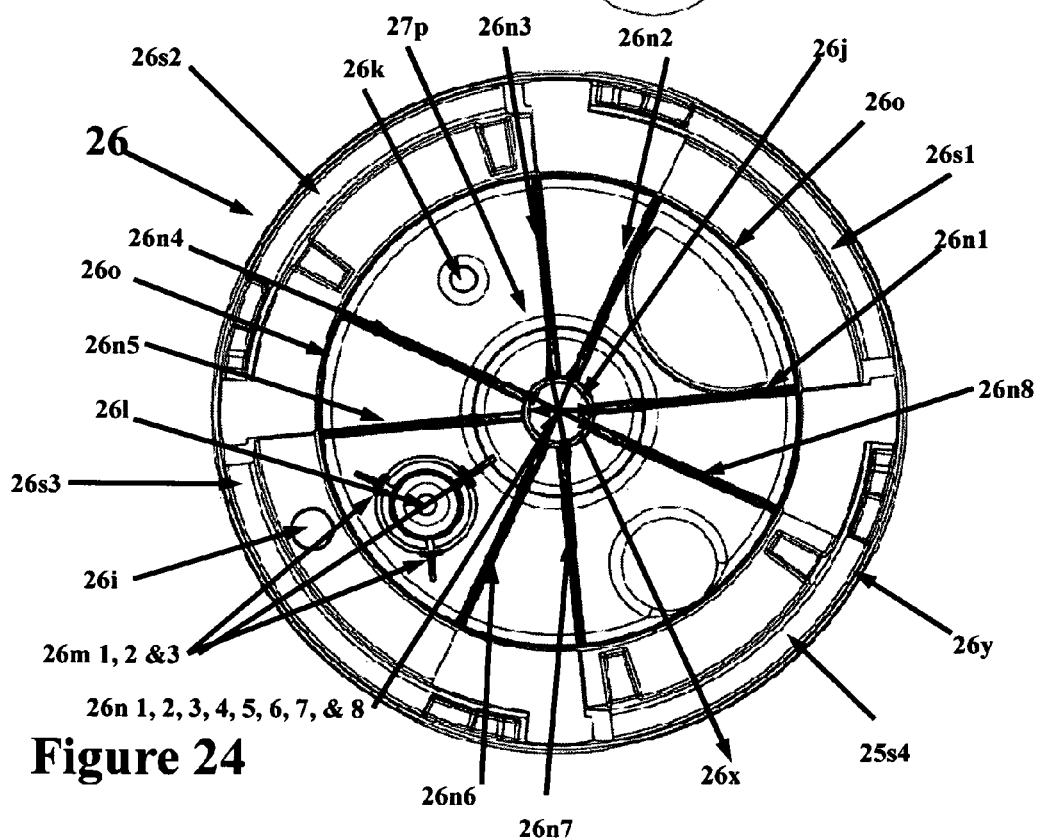

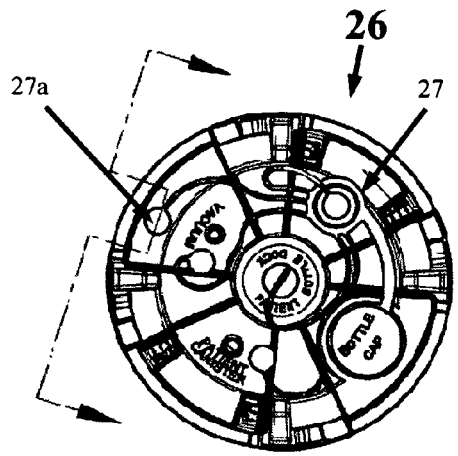
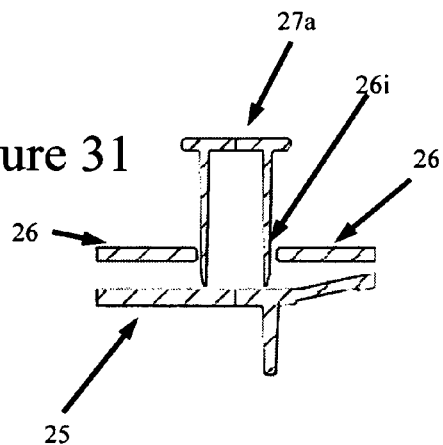
Figure 31
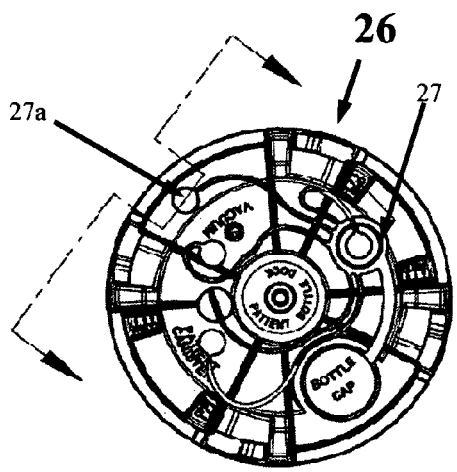
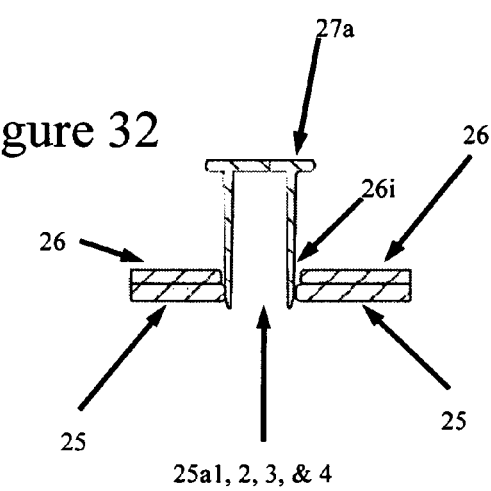
Figure 32
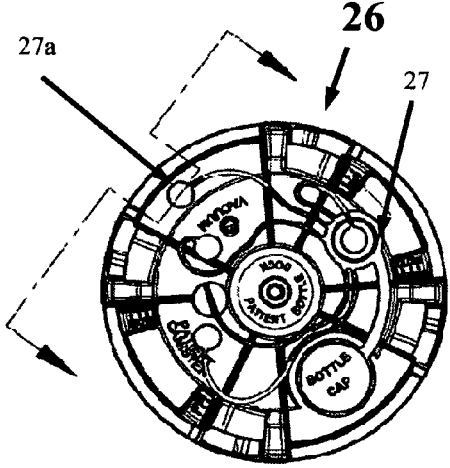
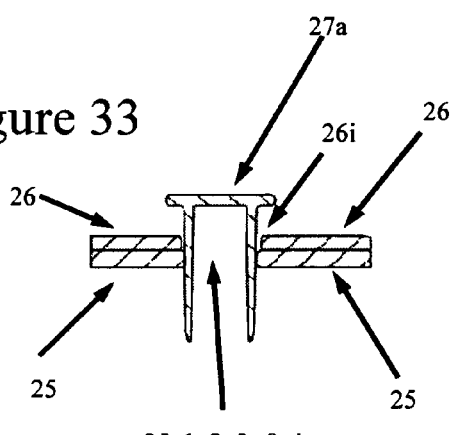
Figure 33

25 and 26 function lid pillars and canister pillars counter-rotationally urged closer along radians/arcs 28

25b1e, 2e, 3e, 4e lid pillars and canister pillars allowed to separate counter-rotationally along radians/arcs 28

Lid 26 motion/force 25e  ff  26a3    26h4    25b1, 2, 3, 4    Canister 25 Motion/force    25e
         25c1, 2, 3, 4                                              ff  260  25d

25 and 26 function

25b1e, 2e, 3e, 4e — lid pillars and canister pillars allowed to separate counter-rotationally along radians/arcs by a force of a first direction Lid pillars and canister pillars counter-rotationally urged closer along radians/arcs by a force of a second direction 28-lid 26 first motion
25e  ff1  26a3  26h4  25c1, 2, 3, 4  28-canister 25 second motion  26o  25d  ff1
25b1, 2, 3, 4  25e  ff1

25 & 26 function

ENVIRONMENTAL NUCHAIN ENTERPRISE RESOURCE PLANNING METHOD AND APPARATUS

CROSS REFERENCE TO RELATED APPLICATION

This non-provisional patent application claims the priority benefit under 35 USC 119(e) U.S. Provisional Patent Application Ser. No. 61/395,346 which was filed on May 12, 2010.

INCORPORATION BY REFERENCE

This patent application incorporates by reference herein U.S. Provisional Patent Application Ser. No. 61/395,346 filed on May 12, 2010. This patent application incorporates by reference herein U.S. Pat. No. 7,185,681. This patent application incorporates by reference herein U.S. Provisional Patent Application Ser. No. 61/395,584.

FIELD OF THE INVENTION

This invention relates to the field of reducing the waste stream burden in the medical field, but not limited to that.

BACKGROUND OF THE INVENTION

In particular, this application relates to systems used in the collection and disposal of certain medical wastes. The collection of fluent waste material is a common procedure in the medical field. Most methods of surgical waste collection are carried out using vacuum suction. Some methods use gravity, while some use impelling devices which produce suction vacuum. Examples of such impelling devices may comprise a meniscus shaver, a lipo-suction system, an arthroscopic fluid pump, a tissue ablator, an endoscopic irrigation and aspiration wand and the like. Surgical fluid waste is collected in containers commonly referred to as canister and/or canister liners. These waste collection devices are generally disposable, some are re-cycled, re-processed, or rewashed. Some collection devices are re-used. Some are partially reused while some are intermittently re-used. Some are disposable or partially disposable. Some are used in conjunction with servicing units while some are used with additive agents for treating the waste material. Some are used multiple times on multiple patients without the preferable cleaning in between treatment of different patients. In certain instances reused devices are cleaned, reprocessed, sterilized, re-sterilized and or recycled and or prepared for reuse. There are disadvantages to the use of disposable collection canisters and canister liners. One problem is that disposable collection canisters and disposable collection liners contribute contaminated infectious plastic waste to the medical waste stream which is undesirable for the environment. Reuse of disposable collection devices by recleaning or reprocessing or recycling and or sterilizing, has the disadvantages of adding costly labor and requiring additional labor costs for sorting, containing, transporting and handling of contaminated medical waste containers, and then the added costs of product re-entry into the internal/external product re-sterilization internal/external distribution system. There is a significant need to reduce medical waste. The need to reduce medical waste is a serious common goal of the United States and Internal Agencies. The Environmental Protection Agency (EPA) and the American Hospital Association entered into a landmark Memorandum of Understanding (MOU) formally establishing the goals to reduce medical waste 50% by the year 2010. Hospitals for Healthy Environment (now Practice Greenhealth) (www.H2E-Online.org) is the name of the aforementioned alliance for waste reduction, supported by formidable organizations and companies such as the American Nurses Association, Healthcare Without Harm, the EPA, plus Group Purchasing Organizations, leading health care organizations, federal, state and local government agencies and health care associations and the like.

It is important in the health care field to have good quality sturdy and reliable products. This is true especially in the field of collection of contaminated biological waste material. Containers for these purposes must be easy to use, and be designed with good human factors and ergonomics for the operators of such devices. One key important ergonomic feature is that the systems for collection of biological waste must be easy to use, and the amount of effort and strength required to assemble such systems should be easy and require little effort by the operators. The instant embodiments of the instant case provide for such ease of use. In addition other useful features which represent good quality standards for collection containers and systems and methods involve stability so that when containers are placed on a horizontal surface they are stable. The container should be puncture, leak and impact resistant and be stable and secure when dropped. They should be manufactured out of materials which function for the intended purposes, and if made form a polymer, have a durometer that should not crack or break if dropped. Labels and brackets should be made durable. The system should be autoclavable so that if desired by the customer, it may be reused. The systems should be available in various sizes to accommodate a variety of patient populations as well as be effective to operate in a number of different treatment situations and locations. The system should not have any parts that are sharp, that might compromise the operator's personal protection, and not tear gloves, or other personal protective equipment such as gowns, gloves, masks, etc. Designs of systems of this sort should promote safe clinical care and perform according to those safe clinical standards. The design should promote resistance to opening after final sealing for disposal, as well as promote easy assembly and easy opening (in this case easy sealing and unsealing) with good ergonomic and human factor attributes. All closure seals should function tightly and maintain the leak proof seal during use, handling and transport. The design should accommodate easy carrying and handling so that transport of the systems may be done safely without contaminating the surrounding environment. Grips and handles should be designed for ease of access and use. Parts should be designed for ease of decontamination, and be rugged to withstand multiple autoclaving if desired. Openings must be free of obstruction, entanglement and sub-assembly parts must be able to attach and dis-attach without requiring undue hand work or significant effort.

In addition various scenarios that occur during health care supply chain efficiency and supply chain management which requires unique features of products that encounter such scenarios. Some scenarios occur in the operating room. For example, collection systems should be designed to be easy to use during room turnover. They should be easy to use during intra-operative bottle changing. They should be easy to use after terminal sterilization and during pre-procedure room setup. And they should be easy to use when preparing an operating room at the beginning of the operating day. Such collection systems should be easy to check/test to make sure they are operating correctly. Especially in a vacuum suction collection system, testing suction and checking seals must be easy and without undue fiddling of parts or undue manipulation. This is especially significant whereas many time the individual who may be preparing the collection system for use, may do so prior to and at time different than actual use, which means the operator setting up the system for use is not the same operator using the system to collect waste. Ease of checking/testing, especially of the seals becomes important if, for example an individual does not properly assemble or prepare the system for subsequent use and then the operator must subsequently insure the system is in intended working condition at a later time. It is also desirable, when dealing with contaminated biological waste that minimum handling of unsealed containers holding biological waste material is kept to a minimum, and that containers are sealed prior to transport. It is also important that a minimum of handling be required during the various scenarios mentioned above and that hand and hand coordination may be achieved to carry out the aforementioned clinical safety features. It is understood that the aforesaid features of the aforesaid scenarios do not only apply to the operating room. Other settings as further defined by the instant application are all applicable. Another example is that safe sealing of containers containing biological waste must be achievable with one handed techniques as provided by the instant system. These practical features bring good ergonomic and human factors to the instant system while providing a good clinically safe system into the health care setting.

DESCRIPTION OF THE PRIOR ART

Certain disadvantages of the prior art in these regards will become better understood with the explanations of the following references. U.S. Pat. No. 5,792,126 to Tribastone, et. al., discloses a collection canister system comprising canister interior of preferably 5000, 10000, and 15000 cubic centimeters and taught to be effective for all procedures. A container of this size has disadvantages because it is too big for many collection applications. For example, suction collection for anesthesia where it is convenient to have a small collection canister attached to an anesthesia machine is preferable, especially in that most anesthesia suction volumes may constitute just a few cubic centimeters of sputum or pharyngeal throat saliva most of the time. Larger equipment is also inconvenient in smaller rooms where suction collection equipment is found such as in the emergency room, the intensive care unit, the coronary care unit, patient hospital rooms, the neo-natal infant care units, physician offices, physician owned surgery suites, physician office surgery and procedure rooms, outpatient surgery centers, ambulatory surgery center, including in addition, ambulances and other rooms beside operating rooms which require smaller apparatus for smaller more confined spaces. There are also concerns with cross contamination in systems where contaminated waste material remains in a room during the presence of subsequent multiple patients. Another disadvantage of the larger 5000, 10000, 15000 cc containers is weight and mobility. Such weight in the extremely large heavy volumes sometimes present difficult ergonomics imposing risk of injury to personnel such as back pain, and other injuries whereby by seams in floors and door jams which are not smooth may induce tipping over and spillage of large volumes of medical waste. Another disadvantage of such large heavy containers is its size. Such large container are more difficult to keep clean and cumbersome to handle, and because of the larger size and could cause ergonomic strain as related to the U.S. Pat. No. 5,792,126 reference. U.S. Pat. No. 5,960,837 to Cude et. al., discloses a suction canister and lid combination whereby only a destructive force will only separate the parts which renders the Cude invention to be an only disposable product which is costly whereby each time a canister is used another is purchase to replace it. A purchase is made and is costly to the customer and each plastic disposable product enters the disposal chain waste stream and another piece of garbage enters the land fills or incinerators which are disadvantages. This is expensive, and requires ongoing inventory space, inventory handling which are at an expense disadvantage. Another disadvantage is a lack of choice for the customer to re-process, re-sterilize or re-use which options are beneficial but not available with the U.S. Pat. No. 5,960,837 reference. U.S. Pat. No. 5,901,717 to Dunn et. al., discloses a canister and flushing system. This system comprises a complex system for handling a collection canister. The disadvantages of this system are that expensive equipment is required and it is complex equipment. These are expenses plus maintenance requires periodic inspection by biomedical engineering which increases labor costs associated with its presence. In addition the equipment must be kept clean which is additional requirement for daily operations. Other disadvantages of a reusable canister includes costly labor and higher personnel overhead, for internal processing, reprocessing, resterilization and reusing. In most institutions, volume of such collection systems is quite high imposing internal/external processing costs. The system discloses the disposable flush kit which maintains higher disposable costs along with the higher costs associated with internal distribution, inventory handling and higher disposable waste removal costs. U.S. Pat. No. 4,419,093 to Deaton discloses a reusable canister having a disposable lid and liner.

This system is delivered in pieces and requires subassembly by the customer prior to operation. This requires additional labor which is costly and involves the inventory tracking of a plurality of pieces of a system in sets and often times lids and liners can become separated and when out of numeral matching balance one cannot be used with out the other, whereas resulting in a incomplete set and a unusable subassembly. This disadvantage complicates the ongoing internal/external distribution and tracking of pieces which adds costly labor, inventory management and excess handling. The U.S. Pat. No. 4,419,093 reference also discloses the contribution of garbage to the waste stream which is a serious environmental concern. Other disadvantages of disposable collection containers include the difficulty in which to assemble a lid to a container body. Many disposable canister systems have a container body which is stackable. This stack ability allows the container bodies to be nested on each other with one container resting substantially within the other with the exception of about one to two inches of body length. This stack ability feature is desirable whereas the volume of container handling in the disposable application is very high. For example a busy institution may process anywhere between 10,000 or less and 50,000 or more disposable canisters per year. The stack ability feature makes these canisters easier to transport in volume. One problem with the assembly of such stackable canister and it's associated lid, is that the snap on feature of the lid must be very tight in order for the lid to be fluid leak proof in the event of tip over. In order for these canister lid interfaces to be leak proof they must fit very tightly making for a very difficult press together assembly. The force required to assemble the canister and lids of this nature is greater than a force which would normally be deemed easy to use. In fact they are very difficult to use. Good ergonomic systems include assembly and dis-assembly features that do not require undue finger, hand and/or upper body strength. Many of the prior art collection systems have snap together features that, due to their seal design, require more force to assemble, than most operators can easily provide.

This is because of the force required to snap together the seals which are not meant to come apart, must be tight enough to stay sealed during transport, handling and tipping over. The applicant believes that if a system cannot be assembled with much less force and upper body strength of the average operator, then there are human factors and ergonomics design issues. The applicant believes that the snap fit force utilized to keep a lid and canister housing together during transport and tippage is not the same force that provides for good human factor/ergonomic and good clinical handling. Applicant contents that when snap fit forces are greater that the average upper body strength of the average operator, then clinical safety is in jeopardy and personal protective equipment such as protective gloves are at risk for tearing or hole.

DESCRIPTION OF THE INVENTION

The instant embodiments provides methods and apparatus for establishing and managing NuChain ERP Systems by NuPurposing products and containers into uses and applications that provide additional value, rather than just throwing spent containers into the garbage. The embodiments of the instant case solve problems. For example, when pour bottles are NuPurposed into canister liner applications, it becomes cost effective to manufacture re-usable and permanent canister systems as taught by the instant case. Also, human factors and ergonomics involving exchanging filled NuPurposed containers becomes difficult. Switching out bottles with respect to a permanent canister system requires the minimum amount of complexity of hand movement and reasonable amount of hand strength. The instant case solves the problem of hand strength. The instant case solves the problem of human factors and ergonomics. The instant case solves the problem of cost competitive manufacturing by providing a lid, canister and capping member designs that only require single pull tooling.

The instant case solves cost problems by providing parts made from of single pull tooling that can manufacture systems at a lower cost so the system bottle dock system may also function as a disposable. The instant case solves the problem of cost competitive manufacturing of a lid, canister, and capping member design that only requires a single pull tooling for manufacturing permanent systems out of more durable and heat resistant materials for permanent autoclavable systems. The Instant case also solves the problem of what to do in a scenario whereby there are no bottles to NuPurpose. The instant case also provides a functional ergonomic system having a low parts count requiring only a few number of single pull injection molding tools. The instant case embodiments comprise utilizing fluid enclosing product transfer delivery containers which do not embody the self inherent physical construct capacity to maintain shape under reduced vacuum pressures up to minus 1 atmosphere. Examples of cost effectively fabricated fluid enclosing containers made for delivery of fluids which may not embody inherent implosion resistant structural strength and rigidity needed for suction vacuum collection may include plastic delivery containers such as plastic pour bottles and intravenous solution containers. The present invention discloses cost effective practical solutions for reducing waste, reducing labor, reducing inventory, reducing the receiving, reducing the internal distribution, and reducing the inventory handling costs and the space required to carry inventory all involved with the collection waste materials. These achievements are carried out by the instant embodiments whereby successful suction vacuum collection may be realized, using in a flexible manner, cost effectively fabricated fluid enclosing distribution, commercialization, and for transfer delivery containers. This patent application discloses collection systems that teach use of fluid enclosing product supply containers for collection, removal and disposal of waste material and in the disposal chain. In particular, delivery containers for general distribution, transfer, administration of pour bottle solutions and intravenous solutions, parenteral and enteral solution containers and the like are converted into the waste collection and disposal chain. This application also teaches use of common fluid enclosing containers for both the supply and the disposal chain. The instant application also teaches use of containers found in inventory for supply and delivery of fluids, and then, transforms them for collection removal, and disposal utility in the deposal chain. This application teaches the use of common fluid enclosing containers for the product transfer and then integrates the containers into systems for the collection and the removal of waste material. The instant application teaches waste reduction methods by integrating delivery container fabrication and the collecting and disposing of waste materials. Potential container fabrication processes applicable to the instant case comprise blow fill seal manufacturing, blow molding, or continuous blow molding, which produces open top containers that may be capped and closed or sealed. Another type of container fabrication process applicable to the instant application is a blow fill seal fabrication process commonly known as producing close top containers, e.g., a manufacturing machine and process whereby a container is formed, filled with fluid, and hermetically closed within one machine. The instant application teaches waste reduction methods by using manufacturing methods as mentioned such as blow molding, blow fill sealing, laminating sheets such as in intravenous solution container manufacturing methods to form solution enclosures. One purpose of the instant case is to transform these containers which are derived from a fluid delivery mode of product transfer and administration and then converting the container to collection removal and disposal of waste materials.

The embodiments of the instant case provides container utility options for the transfer and administration of products, consumption of products and for the waste collection removal and disposal options. The embodiments of this instant case discloses the utilization of fluid filled product transfer containers such as pour bottles and/or intravenous solution containers (IV bags) (and/or other product/fluid containing enclosures used for intravenous therapeutics and the administration of anesthetic agents as well as other medicaments) for the receiving, collecting, containment and disposal of waste. Using fluid enclosing product distribution transfer/administration containers also for the handling of waste, results in optimal reduction of waste, reduction of inventory, reduction in labor, reduction of internal/external inventory distribution/processing/re-processing/re-using/re-cycling, reduction of inventory handling and waste disposal costs (brought by the unnecessary need for separate supply and disposal containers in certain circumstances). The forgoing are all positively impacted by eliminating the supply chain costs associated with the fabrication of the said separate supply and disposal/collection containers. The question arises, why pay for disposable containers when a fluid delivery container can be derived from the supply side of the supply and disposal chain and then such containers may be converted into a collection and removal/disposal containers. Such containers are supplied clean/sterile and are made to meet certain sterility assurance levels (SAL). The instant embodiments confer options allowing consumer choices for the reduction of waste. Plastic transfer containers such as blow molded containers, continuous blow molded containers, blow fill seal containers, intravenous solution containers, containers made of laminated sheets of polymers and of foils, are commonly used for the distribution transfer and administration of fluid products and other product such as sterile water, sterile saline solution intravenous solutions for IV therapeutics, IV solutions for administration of anesthetic agents and other water for injection (WFI) based fluid formularies as used in the medical field. Also others included may be cleaning solvents, prep solutions, alcohol solution and the like. Only certain of these solutions are used for intravenous therapeutics, parenteral administration, and administration of anesthesia, wound irrigation, irrigation for arthroscopic, endoscopic, laparoscopic procedures, irrigation for urology procedures and many other types of applications. The instant application conceptualizes additional fluid materials delivered in polypropylene, and high density/low density polyethylene, and/or polyvinyl chloride containers which are all generally high volume supplies and or engage the supply chain on a just in time basis or on a vendor managed inventory basis or a customer managed basis for delivery and consumption of fluids, and the collection and disposal of waste materials.

Intravenous solution containers are also used for the distribution/commercialization of these container solution products. It is understood the disclosed teachings of the instant case are not limited to sterile liquid distribution/supply containers or the transfer of fluid filled product containers. Other product transfer containers may be suitably integrated with innovations of the instant case, to function during the delivery and waste disposal capacity. Other containers such as prep solution containers, alcohol containers, solvent containers, cleaning solution containers and the like may function suitable within the scope of the present invention for other applications. These teaching are not intended to limit the attached claims below. Other product containers may also be used in the instant inventions. These product delivery containers are commercialized/distributed to the customer having volume cubic capacity sufficient in substantial proportion to certain collection and the disposal of waste materials. The instant embodiments reduce the amount of plastic introduced to the waste stream. The instant embodiments reduce the recycling, reprocessing and labor associated with the handling and re-use procedures thereby lowering the associated costs of waste removal. The instant embodiments reduce the supply chain costs from manufacturing to disposal. Collecting fluent waste material in fluid enclosing delivery containers such as open top blow molded, or continuous blow molded containers, intravenous solution containers, irrigation solution containers, closed top blow fill seal containers or form fill seal containers, all which have been cost effectively fabricated with thin walls and which do not have the strength or construction to resist high vacuum implosion forces provide various supply chain solutions and consumption options for solving the disadvantages and problems of prior art delivery and collection containers. When the methods and apparatus embodied in the teachings in the instant application are utilized, the instant embodiments also provides for reducing the handing, reducing the labor and reducing the costly process of recycling, re-using re-processing sterilizing and or re-sterilizing. Certain product delivery transfer containers are fabricated, commercialized, and are already present or in the supply, distribution, inventory, administration chain and or in the customer facility. The present embodiments conveniently transforms converts and integrates these fluid enclosing transfer delivery containers into waste materials collection containers establishing a new type of environmental supply chain. We refer in part to this new novel environmental process as a disposal chain supply system by the deployment of supply chain supplies to collect, remove and dispose of waste material. This defines new supply and disposal chain systems, methods and apparatus for using fluid enclosing distribution containers and methods for processing systems from the clean delivery side, e.g., the fluid administration/consumption, into the dirty collection, removal and disposal side integrating the disposal chain and the supply chain for environmental purposes herein referred to as disposal chain supply systems. Disposal chain supply systems define a novel environmental process. In essence disposal chain supply systems are defined by transforming distributing containers into collection removal and disposal containers. A dispose and supply container is an environmental conversion and transformation methods. A disposal chain/supply chain container utilizing disposal chain supply chain systems confers options and advantages and disclosed by the instant case. Disposal supplies are environmentally preferred. Disposal supplying is the environmentally preferred method.

Difficulties exist with the use of certain containers when integrated into high negative pressure vacuum/suction system. Negative vacuum draw pressures at times up to minus one atmosphere of negative pressure is common for drawing surgical waste materials from a surgical site into a collection receptacle. One problem is that the common blow molded or blow fill sealed containers are cost effectively manufactured with relatively thin plastic walls sometimes down the thickness range of 0.025 inches or less and are generally made with a plastic materials such as high density polyethylene, polypropylene, polyvinyl chloride, or other like materials. Thin walled containers are commonly fabricated to reduce the plastic material mass (volume of plastic materials per unit) and hold down production costs and shipping weight. It is common practice when container manufacturing to consume the minimum amount of material used per unit to fabricate each container yet maintain user function for cost effective manufacturing purposes. Common container material durometers comprising containers having such ranges of this wall thickness in these like materials are not generally strong enough to withstand the reduced pressures of up to minus one atmosphere as commonly found in a vacuum/suction system, without imploding or deforming. Product fluid enclosing distribution transfer containers are commonly fabricated using processes know by artisans skilled in the arts of blow molding or continuous blow molding of open top containers and/or blow fill sealing of closed top containers as well as using such manufacturing processes such as thermal lamination of plastic sheet to form cavities/enclosures for the filling and production of intravenous solution containers, parenteral solution containers and other types of containers.

One solution to the problem of implosion and bottle/container deformity which may occur under high vacuum pressure is to connect a container to a suction collection system whereby the containers walls are interposed between its inner chamber and an outer space with each space subjected to a common amount of negative draw vacuum force/pressure. Such a reduced draw force is directed inside of and outside of a supply container and as said force envelopes itself inside and outside of the container which forms container wall supporting pressures which provides enforcing balances by effecting a substantially neutralizing net implosion and explosion force on the container wall at the same time eliminating negative unbalanced forces on the container wall. This is carried out by the container and canister of the instant case co-acting to egress and ingress forces, for the collection of waste under such a balance of draw forces along the composite draw path which emanate from a draw source. This addresses one issue of container deformity. This instant application discloses the neck of the pour bottle as the utilitarian area of the bottle for coupling with the lid of a canister system. The instant application discloses a throat aperture space (pour spout) of a plastic pour bottle as a utilitarian area for engagement of draw forces. The instant application discloses the throat space aperture, pour spout as a utilitarian area for coupling of a throat aperture plug. The instant application discloses a vacuum force egress and ingress exchange plug, and a bottle and canister configuration for providing communication of the draw force applied on the inside and outside of a fluid administration container. The instant application discloses locating an atmospheric pressure draw exchange at the neck of the container. The present application discloses interposing the container neck (pour spout) annularly between a plug and a lid for conversion coupling peripherally (not necessarily round). It is understood the invention is not intended to be limited to bottle neck configuration which are round. The present invention discloses positioning the plastic container throat space in a negative pressure draw vacuum system whereby an out draw force and an in draw force is disposed to be egressed out of a container and transfer and deposit waste material into the container. The embodiments of the instant case utilizes the inner chamber of a plastic pour bottle as part of the pressure vacuum draw path.

Methods of Embodiments

One object of an embodiment of realizing a NuChain supply chain and disposal chain systems by NuPurposing is to position a liquid transfer and fluid enclosing container upstream to a patient delivery sequence, and then place the container downstream in connection with the flow of a waste material. Another object of an embodiment of creating a NuChain supply chain and disposal chain systems by NuPurposing is to convert a liquid container affecting egress of the liquid and then the positioning of the container in flow confining connection downstream to a source of waste material. Another object of an embodiment of creating a NuChain supply chain and disposal chain systems by NuPurposing is to pour solution from a container and then place the container downstream along a vacuum draw path in flow control connection with a suction wand. Another object of an embodiment creating a NuChain supply chain and disposal chain systems by NuPurposing includes positioning a liquid transfer container upstream to and in vascular access connection with a patient and then position the transfer container downstream in flow control composite connection with a vacuum draw path.

Another object of an embodiment creating a NuChain supply chain and disposal chain systems by NuPurposing is to provide supply chain efficiency whereby the dispensing container is also the receiving receptacle/container. Another object of an embodiment is creating a NuChain supply chain and disposal chain systems by NuPurposing to provide the waste reducing processes whereby the egress of the container upstream from a healthcare patient is the same container positioned downstream in flow control association with a negative atmospheric air pressure draw force drawing air and in a configuration such as being adapted to be in flow confining connection with a suction wand. Another object of the embodiment creating a NuChain supply chain and disposal chain systems by NuPurposing is to provide practical steps for internal container handling including a) fabricating a transfer container, b) taking a transfer container and extending a draw path between a vacuum source and a suction wand, c) connecting a fluid enclosing delivery container to the path, d) depositing the waste material into the container. Another object of an embodiment is to provide methods and systems including a) enclosing a fluid in a container at manufacturing and transferring through distribution and administration for health care consumption, b) consuming at least a portion of the fluid product, c) converting the container into a vacuum collection system, d) removing the waste in the container e) disposing the waste. Another object of an embodiment creating a NuChain supply chain and disposal chain systems by NuPurposing includes a supply and disposal method comprising a) manufacturing a fluid enclosing container for the distribution, transfer and administration of a fluid product, b) consuming at least a portion of the liquid, c) directing a draw force to and from the container along a composite draw path, d) depositing waste material into the container. Another object of an embodiment establishing a NuChain supply chain and disposal chain systems by NuPurposing is to provide a method for reducing supplies comprising, a) providing a container fabricated for the delivery of a product, b) delivering the product, c) connecting the container to a vacuum source system, d) drawing waste material into the container, e) removing the waste material in the container, f) disposing of the waste material. Another object of an embodiment is to provide a method for reducing waste comprising a) transforming a waste receptacle from a container manufactured for enclosing and delivering a fluid, b) connecting the container to a composite waste draw conduit, c) depositing the waste material in the container, d) removing the container from the draw path, converting another delivery container into a waste receptacle comprising transformation of a fluid enclosing supply container into a waste collection receptacle. Another object of an embodiment includes providing the methods and systems for the transforming a plurality of supply containers into a plurality of waste containers. Another object of an embodiment establishing a NuChain supply chain and disposal chain systems by NuPurposing is to enclose a plurality of supply containers having been transferred into a plurality of collection container within a single enclosure. Another object of an embodiment establishing a NuChain supply chain and disposal chain systems by NuPurposing is to provide methods for transforming supplies into waste receptacles comprising a) constructing a fluid enclosing container, b) taking the container c) extending a draw path between a vacuum source and a suction wand d) connecting a delivery container to the path, e) depositing waste material into the container. Another object of an embodiment creating a NuChain supply chain and disposal chain systems by NuPurposing is to provide methods for deriving waste receptacles from supply containers including a) providing a liquid product in a selectively connectable waste receptacle b) disposing the receptacle in a vacuum collection container system, c) drawing a force along a composite draw path between a source of waste material and a vacuum source d) depositing waste in the delivery receptacle. An other object of the instant case comprises positioning a transfer container upstream in the flow of patient care sequence for liquid dispensing and administration, b) positioning the container downstream in the flow of patient care in a material receiving and receptacle mode. Another object of the embodiments herein creating a NuChain supply chain and disposal chain systems by NuPurposing is disclosed whereby the receptacle is positioned on the clean side of the supply and disposal chain for dispensing of it contents and the dispenser is position on the dirty side of the supply and disposal chain for receiving waste material as a receptacle, and such receptacle is in receiving structuration with a gravity flow system and or a composite vacuum draw path. Another object of an embodiment creating a NuChain supply chain and disposal chain systems by NuPurposing is to provide methods and systems for drawing a negative pressure within a transfer dispensing container. Another object of an embodiment creating a NuChain supply chain and disposal chain systems by NuPurposing is to provide methods for placing the container downstream to a flow control conduit depositing waste into the container under a positive push force, not a negative vacuum force. Another object of an embodiment creating a NuChain supply chain and disposal chain systems by NuPurposing is to provide methods and systems in structuration with a draw force including a) enclosing a fluid in a container at fabrication and providing the fluent material in a selectively connectable receptacle, b) disposing the receptacle in a vacuum collection canister system(s), drawing a force along a composite path from a source of waste, depositing the waste into a delivery receptacle. Another object of the embodiments herein creating a NuChain supply chain and disposal chain systems by NuPurposing as disclosed is to provide connect ability to a transfer a container into a vacuum canister for waste collection in configuration with a canister lid. Another object of an embodiment creating a NuChain supply chain and disposal chain systems by NuPurposing is to provide a composite negative atmosphere draw path formed at least in part by the interior of a transfer container. Another object of an embodiment creating a NuChain supply chain and disposal chain systems by NuPurposing is to provide a draw force directed by a composite draw path in part co-acting to transform a delivery container to dispose waste material. Another object of an embodiment creating a NuChain supply chain and disposal chain systems by NuPurposing is to provide a canister in structuration with a fluid enclosing supply transfer container forming at least a portion of a composite draw path interposed between a vacuum source and a site of material waste. Another object of an embodiment is to combine in association with the novel features cited above, a negative draw path with a material flow path. Another object of an embodiment creating a NuChain supply chain and disposal chain systems by NuPurposing is to combine a draw path with the material draw path to dispose material in a transfer container to remove waste material from a site. Another object of an embodiment creating a NuChain supply chain and disposal chain systems by NuPurposing is to provide a throat aperture space/plug/seal disposed in a transfer container access/port site forming at least a part of the draw path controlling draw force from and to a transfer container. Another object of an embodiment creating a NuChain supply chain and disposal chain systems by NuPurposing is to provide a receptacle derived from a health care delivery sequence converted to co-act with a canister, a lid, a draw force, a composite path and a bottle throat plug to dispose waste. Another aspect of an embodiment creating a NuChain supply chain and disposal chain systems by NuPurposing is to provide supply chain efficiency methods comprising a) receiving liquid enclosing delivery container, b) transferring the liquid to a delivery site, c) administering the liquid and connecting the container in structuration with a waste collection, d) collecting the waste. Another aspect of an embodiment creating a NuChain supply chain and disposal chain systems by NuPurposing is to provide supply chain efficiency methods comprising a) receiving a fluid enclosing container for the distribution of a liquid product b) distributing a liquid product, c) consuming at least a portion of the product d) directing a negative suction vacuum draw force to the container, e) connecting the container to a composite draw path having a suction wand at one end thereof, e) placing the suction wand in association with waste material and drawing the waste material into the container, f) removing the material in the container, g) disposing the material. Another object of an embodiment creating a NuChain supply chain and disposal chain systems by NuPurposing is to a) fabricate a fluid enclosing delivery container for disposal and collection in a waste collection system. Another object of an embodiment creating a NuChain supply chain and disposal chain systems by NuPurposing is to provide a method of reducing waste comprising enclosing a fluid product in a fabricated delivery container, egressing the fluid from the container, and connecting the container along a vacuum draw path, drawing waste material into the container, removing the material for disposal, disposing the material. Another object of an embodiment creating a NuChain supply chain and disposal chain systems by NuPurposing is to provide a method of collecting supplies and transforming them into waste receptacles comprising a) collecting delivery supply containers, b) placing the containers positioned to receive waste in vacuum canisters, c) drawing vacuum, d) controlling the draw force to direct waste material for disposing waste in the transfer container. Another object of an embodiment creating a NuChain supply chain and disposal chain systems by NuPurposing is to provide a method of converting containers having dispensed at least some container contents, converting the container into a vacuum collection system receptive to waste collection and or removal and or disposal. Another object of the aformenetioned objects is to provide a method of handling a dispenser and a receptacle wherein the dispenser is the receptacle. Another object of an embodiment creating a NuChain supply chain and disposal chain systems by NuPurposing is to provide a delivery collection container system using fluid enclosing bottle fabricated from a blow molding, and or a continuous blow molding process out of previously shaped polymer performs. Another object of an embodiment creating a NuChain supply chain and disposal chain systems by NuPurposing is to provide a delivery and collection container fabricated from a fluid enclosing blow fill seal manufacturing process container. Another object of an embodiment creating a NuChain supply chain and disposal chain systems by NuPurposing is to provide a suction/vacuum system which renders product distribution/transfer containers receptive to waste materials. Another object of an embodiment creating a NuChain supply chain and disposal chain systems by NuPurposing is to provide a collection system for reducing waste that is derived from product delivery. Another object of an embodiment creating a NuChain supply chain and disposal chain systems by NuPurposing is to reduce internal/external distribution, internal/external inventory management whether management is carried out by a vender management program or by a customer. Another object of an embodiment creating a NuChain supply chain and disposal chain systems by NuPurposing is for the consumer to account for the cubic volumes of incoming fluids and cubic volumes of outgoing waste materials for analysis and matching incoming and outgoing waste materials to the number of containers needed to optimize the supply purchasing process as practiced within the scope of the instant case. Another object of an embodiment creating a NuChain supply chain and disposal chain systems by NuPurposing is to provide methods and systems for sealing a vacuum draw path and for unsealing a vacuum draw path so that pour bottles, intravenous solution containers, and other types of containers may function to improve supply chain metrics relating to reducing inventory, labor, costs, shipping, and for reducing the overall mass of materials contributed to the waste stream. Another object of an embodiment creating a NuChain supply chain and disposal chain systems by NuPurposing is to provide convenient methods and systems for connecting and disconnecting a composite draw path utilizing in part at least one collection container derived from a supply chain involving the commercialization of a fluent material. Still a further object of an embodiment creating a NuChain supply chain and disposal chain systems by NuPurposing is to provide a lid handle such that movement of the handle in the other direction causes an unseal ability of a vacuum draw path between both a plug (not shown) and lid, and lid and canister. Still a further object of an embodiment creating a NuChain supply chain and disposal chain systems by NuPurposing is to provide a system using parts manufactured by single pull injection molding tools. Another object of an embodiment creating a NuChain supply chain and disposal chain systems by NuPurposing is to provide a suction canister system that functions as both a bottle docking system and a normal canister system. Another object of an embodiment creating a NuChain supply chain and disposal chain systems by NuPurposing is to provide bottle docking capability in a fashion that is ergonomic and easy to use. Another object of an embodiment creating a NuChain supply chain and disposal chain systems by NuPurposing is to provide a reduced parts count and competitive cost manufacturing so that if the user does not have bottles available to dock inside a canister, the system is cost effective and capable of use as a both disposable non-docking and re-usable non-docking canister system. Another object of an embodiment creating a NuChain supply chain and disposal chain systems by NuPurposing is to provide permanent autoclavable and re-usable canister systems to reduce the amount of waste entering the waste stream. To further illustrate the embodiments of the methods and systems of the instant case, this patent application incorporates by reference herein U.S. Pat. No. 7,185,681. In order to additionally illustrate the embodiments of the methods and apparatus of the instant case, this patent application incorporates by reference herein U.S. Provisional Patent Application Ser. No. 11/787,036. This patent application incorporates by reference U.S. Provisional Patent Application Ser. No. 61/395,584.

DEFINITIONS

Bottle dock means a permanent or disposable canister housing systems embodiments of the instant case which is capable of having a fluent material commercialization container transformed and disposed therein for the collection of fluent material waste by the NuPurposing of fluent material commercialization containers into waste collection containers.

NuChain means novel supply chain systems. methods and disposal chain systems created by the NuPurposing of containers such that the transformation and conversion of fluent material delivery containers in collection containers creates a new supply chain and disposal chain system which links the supply chain of one supply chain and disposal chain apparatus to the disposal chain of a completely separate supply chain and disposal chain apparatus. NuPurpose/NuPurposing means the creation of a new purpose for containers such that instead of using a container for an intended purpose and then throwing away such a container realizing no value, the container is utilized for a new purpose like being configured to be bottle docked.

BRIEF DESCRIPTION OF THE DRAWINGS

FIG. 2 depicts the transformation of said fluent filled containers from a first condition shown by circled 1-11, being transformed 13 into a waste collection container as shown by circled 2-12, said transformation 13 from condition 1 to condition 2 being carried out within the facility.

FIG. 5 shows the distribution and receiving of a new empty waste collection container that goes through a facility and/or point of consumption as shown by vector 18 and then leaves the facility and/or point of consumption as a separately produced waste collection container containing waste material as revealed by sequence 2, 8, 18, 9 & 4.

FIG. 11 give rise to the need for an exchange for users to learn of, access and procure containers for the transformation of, or containers which have been transformed as taught by the instant case, in the event a facility or point of consumption is in the possession of an overabundance of containers. This exchange would allow more containers to be conditioned and transformed and prevent such an overabundance of containers from being discarded and contributed to the waste stream.

FIG. 18 is a top isometric view of a locking, plugging and capping and holding member 27.

FIG. 19 is a top isometric view of a suction canister lid 26 which can also perform as a bottle docking suction canister system lid 26.

FIG. 20 is a top isometric view of a canister 25 which can also perform as a bottle docking suction system canister 25.

FIG. 22 is a side elevation view of blow up of the circle of FIG. 23, showing a canister/lid/plug/bottle seals compression ramp depicting 4 places 26/1, 2, 3, & 4.

FIG. 23 is a side elevation view of lid 26.

FIG. 24 is a bottom plan view of lid 26.

FIG. 31 is a blow up cutaway side elevation view of locking member 27a, lid 26 and canister 25.

FIG. 32 is a blow up cutaway side elevation view of locking member 27a as lid lock hole 26i may be positioned in alignment with any one of canister locking holes 25a1, 2, 3, & 4 in preparation for pressing locking member 27a down to lock the rotation and seal of the canister/lid, and the bottle docking assembly.

FIG. 33 is a blow up cutaway view of locking member 27a having been pressed down through lid lock hole 26i and/or any one of canister locking holes 25a1, 2, 3, & 4.

FIG. 37 shows a view of lid 26 And canister 25 and member 27 in a condition sealing lid 26 to canister 25 as well as forming a seal between lid 26, plug 65 (not shown), bottle 19. FIG. 37 also shows the relationship of lid pillars 26a1, 2, 3, & 4 in physical structuration with canister pillars 25b1, 2, 3, & 4. Each of canister and lid pillars are depicted by the number 28 throughout the drawings defining varying sealing and unsealing juxtaposition relation. FIG. 37 also shows capping member 27 conditioned and positioned so that plug 65 is accessible to the suction tip and suction tubing (e.g. a conduit) as shown as an exemplary embodiment so that waste materials may be drawn from a source of waste into bottle 19. Lid port 26l is also shown uncapped and available for a connection with a tubing/conduit that is connected at the other end to a source of reduced pressure.

DETAILED DESCRIPTION OF THE DRAWINGS

Figure 1:
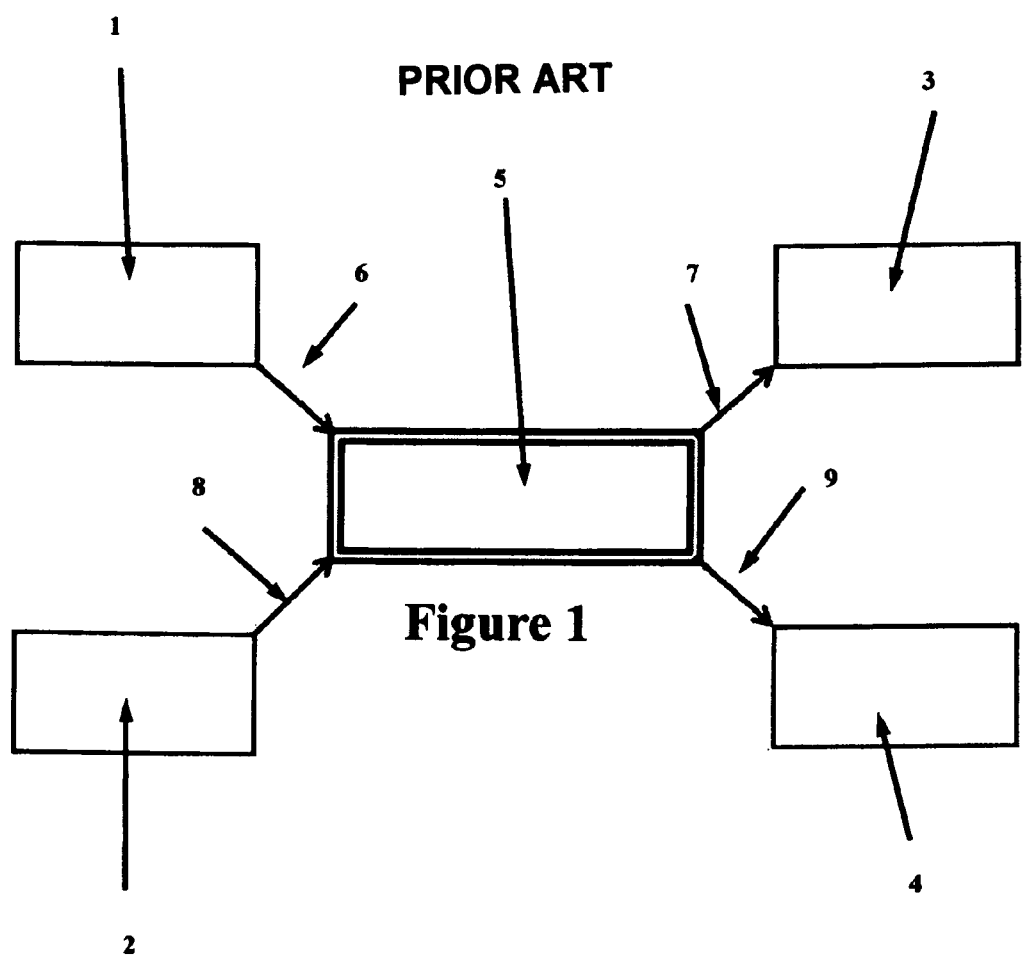
FIG. 1 is a drawing of a prior art supply chain apparatus showing how a fluent material filled container 1 may be distributed to a facility 5 and once the fluent material is used an empty container 3 is then discarded into the garbage. Similarly, a separately purchased empty container 2 may also be distributed to the facility 5 and when that empty container is used or filled it goes into a fluent filled waste container disposal chain apparatus.

Turning to FIG. 1.

FIG. 1 shows two separate prior art schematics. In these two prior art supply chain and disposal chain apparatus's FIG. 1 shows a filled container in a new condition. Number 2 shows an empty separately produced collection container in a new condition. Number 3 shows an empty container of container 1 that is being discarded as garage into the waste stream. Number 4 is a used empty collection container of number 2. Number 5 shows a facility and/or point of consumption. Number 6 shows a supply chain transfer vector showing the receiving of container 1 by a facility 5 or received at a point of consumption. Number 7 is a supply chain transfer vector showing a transfer of empty container 3 away from facility 5 to a waste receiving location. Number 8 depicts a supply chain transfer vector showing the receiving of a separately produced empty collection container 2 by facility 5 (or a point of consumption). Number 9 shows a supply chain apparatus transfer vector of contaminated and used container 2 being transferred from facility 5 to a waste receiving location.

Figure 2:
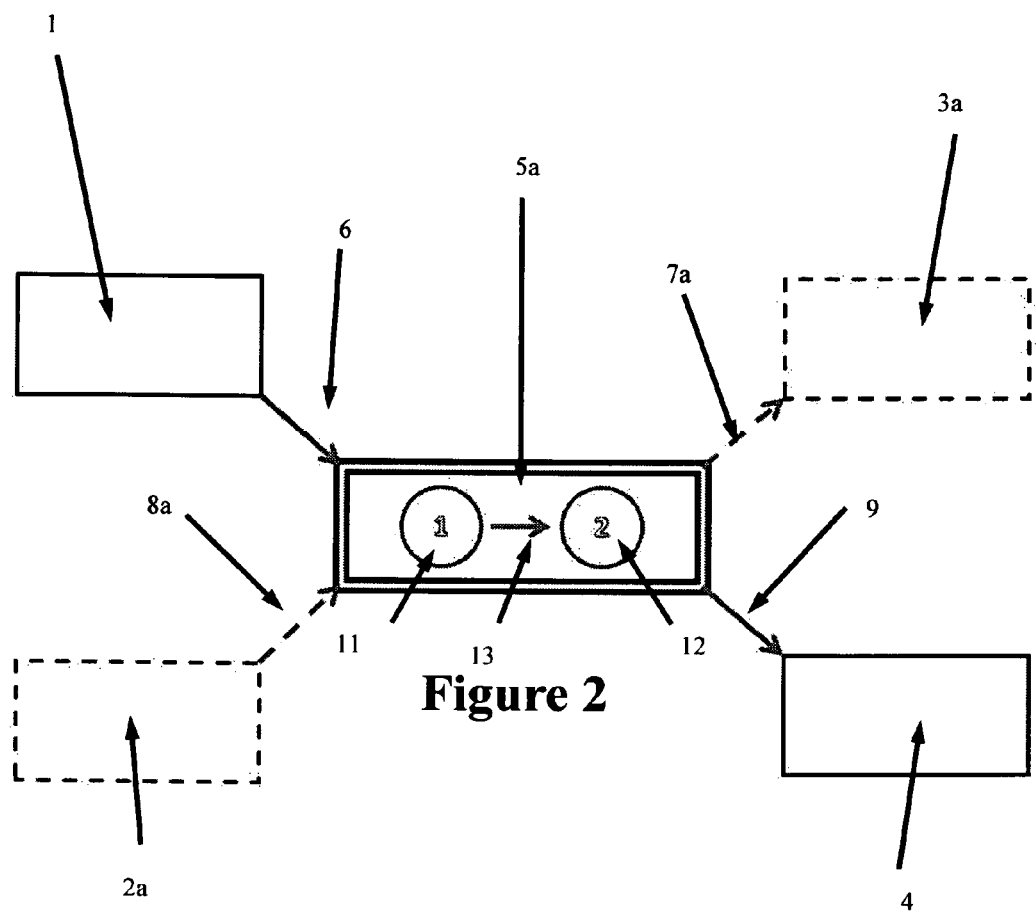
FIG. 2 is a drawing of a NuChain supply chain apparatus showing the elimination of supply chain apparatus 2a and disposal chain apparatus 3a wherein a fluent material container is transformed into a collection container linking the supply apparatus of one supply and disposal chain apparatus with the disposal apparatus of a second supply and disposal chain apparatus. This is emphasized by the broken lines depicting the eliminated portions the aforementioned apparatus.

Turning to FIG. 2.

FIG. 2 shows in broken lines the elimination of empty waste collection container 2 as depicted by 2a and the elimination of the entire supply chain apparatus of container 2-8a. Number 7a shows the elimination of the supply chain vector apparatus of empty collection container 1 and 3a shows the elimination of supply chain apparatus container 1 as an empty unused supply chain container. Also shown within facility 5a circled one is depicted by 11 which defines container 1 in a first condition. Supply chain apparatus transfer vector 13 represents the conditioning and transformation of container 1 into a different state in so far as it has been conditioned for the collection of waste as a collection container.

Figure 3:
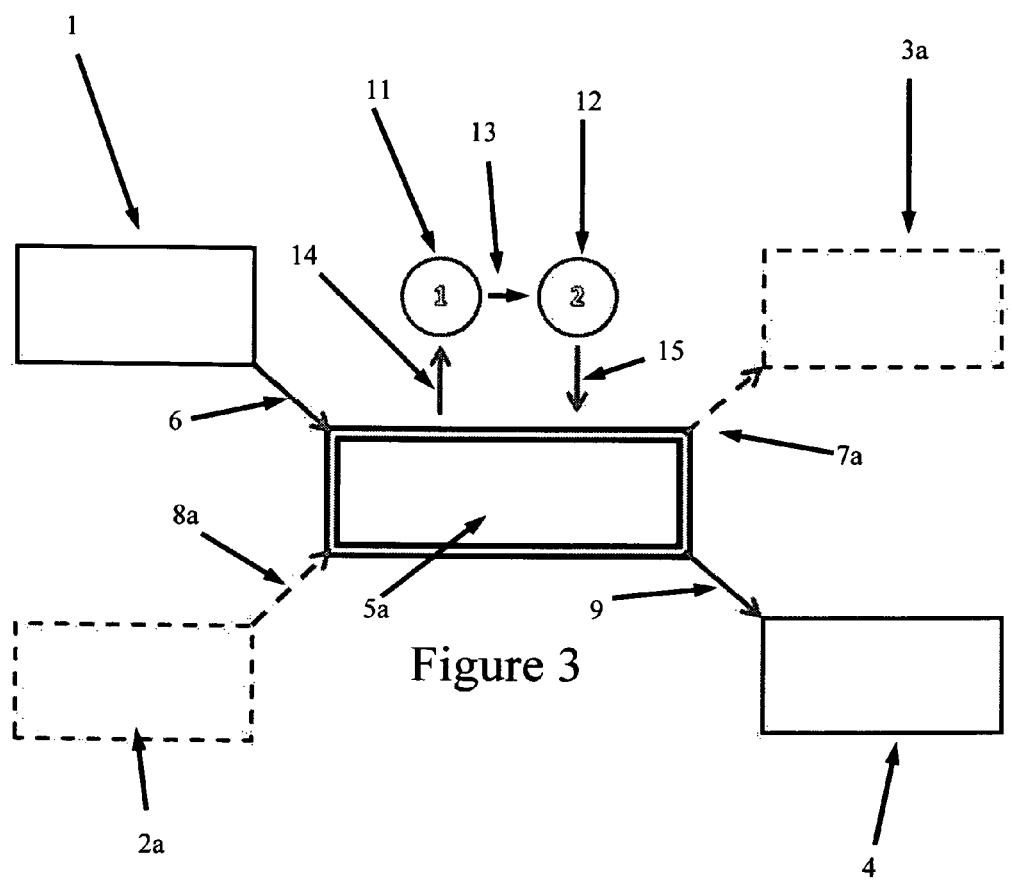
FIG. 3 shows the same drawing as FIG. 2 with the exception that the fluent filled containers circled 1 converts and is transformed 13 from a first condition circled 1-11, to a second condition 2-12 of a waste collection container circled 2-12 as shown by transportation vector 14 after leaving the facility 5a and by transportation vector 15 as shown returning to the facility transformed into a second condition. It is understood that the process shown in FIG. 3 does not depend on the containers described being the same actual physical embodiments in every instance, however in some instances the containers will be the same physical embodiments associated with facility 5a and in other instances the containers shown will be containers derived from separate facilities in that one of the underlying concepts is that NuPurposed containers may be derived from other sources.

Turning to FIG. 3.

FIG. 3 shows the supply chain apparatus of FIG. 2 however the conditioning and transformation of container 1 as depicted by 11, 13 and 12 into a different state for collecting contaminated waste material occurs outside of the facility at a location which is different from where the point of consumption of the fluids of container 1 took place. Supply chain apparatus transfer vector 14 defines the container being transferred to a location outside of facility 5a and supply chain apparatus transfer vector 15 shows container 1 being transferred back to facility 5a in its conditioned and transformed state for use in a different state as a contaminated waste collection container inside facility 5a. It is understood that facility 5a may be the same facility of a different facility in that container 1 may be traded on a NuPurposing exchange (or an online NuPurpose exchange). Container 1 enters facility 5a for egress of its fluent materials and is conditioned and transformed into a waste collection container but then ingresses fluent waste material at a different facility as a result of having been subject to procurement and acquisition rights of a completely different facility, and/or a completely separate point of consumption in a different department of facility 5a or for a different consumption or different use than facility 5a.

Figure 4:
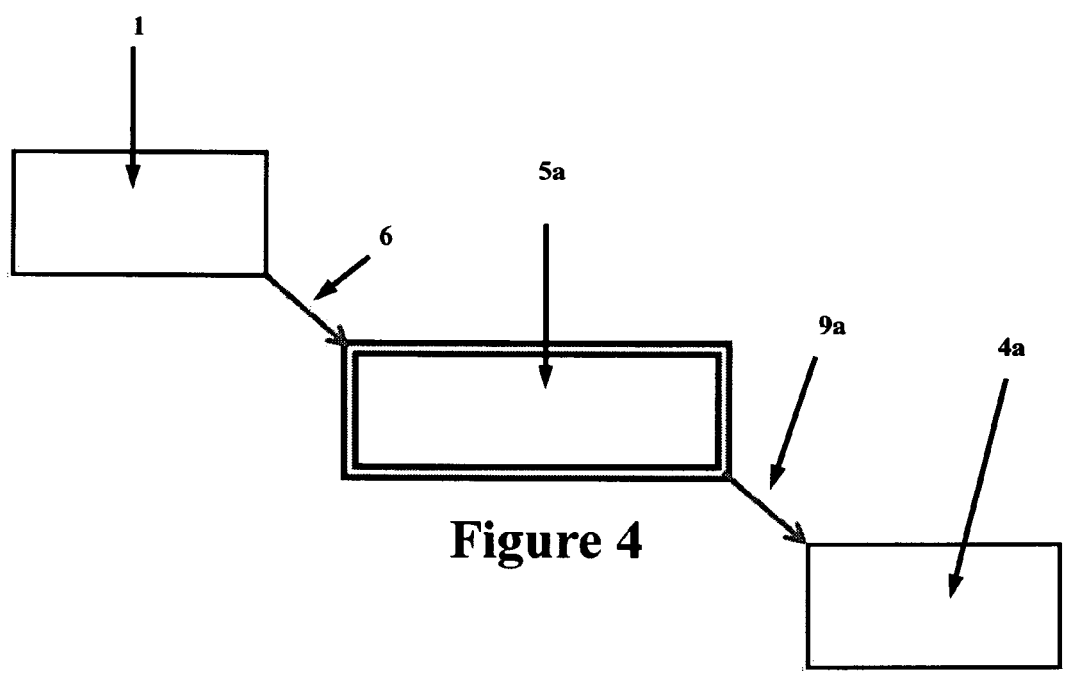
FIG. 4 shows a drawing of a NuChain apparatus wherein the distribution and receiving of empty incoming separately produced waste collection containers of FIGS. 1, 2 and 3 is eliminated, an the disposal of the empty fluent material containers are eliminated and the supply chain apparatus of a first supply chain apparatus is linked to the disposal chain apparatus of a disposal chain apparatus establishing a NuChain supply chain and disposal chain apparatus.

Turning to FIG. 4.

FIG. 4 shows a NuChain supply chain and disposal chain apparatus having eliminated the portions of the supply chain apparatus and the disposal chains apparatus of FIG. 3. The broken lines of 2a, 8a and 7a and 3a of FIG. 3 have been eliminated. FIG. 4 shows the NuChain supply chain and disposal chain system being defined as number 1 which defines a fluent material distribution container. Number 6 defines the supply chain apparatus transfer vector toward facility 5a where a point of consumption occurs and a transformation of container 1 into a waste collection container occurs. Number 9a is a supply chain apparatus transfer vector showing a container 1 having waste material contained therein and being transferred away from facility 5a towards a waste receiving location.

Figure 5:
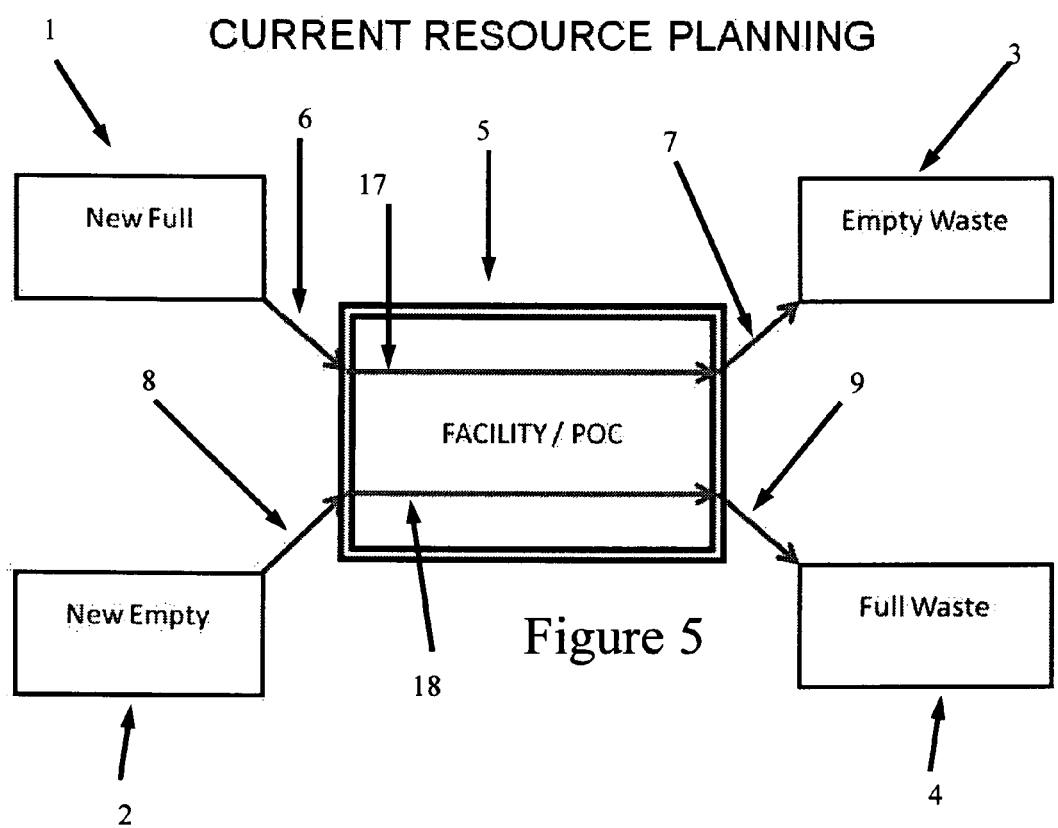
FIG. 5 shows a prior art example of a first supply chain and disposal chain apparatus and a second supply chain and disposal chain apparatus wherein a fluent material container 1 is processed through a facility and/or toward and away from a point of consumption as shown by transfer vector 17 and then leaves a facility/point of consumption as an empty waste container whereby no container transformation or reconditioning occurs in a sequence such as revealed by 1, 6, 17, 7, & 3. In addition

Turning to FIG. 5.

FIG. 5 shows two separate supply chain and disposal chain apparatus's prior art mode of operation involving current status quo enterprise resource planning showing the supply chain apparatus transfer vectors 6, 17 and 7 representing how a new full container is received by a facility at 6 and flows through a facility at 17 and then flows away from a facility at 7 wherein the new full container becomes an empty container as waste/garbage lacking further utility (e.g. not NuPurposed). Also new empty collection container is shown by supply chain apparatus transfer vector 8, 18 and 9 as being received by a facility going through the facility 18 and going away from the facility going from a newly procured new empty waste collection container being delivered to a facility in a new condition into a waste collection container for having fluent material waste enclosed therein.

Figure 6:
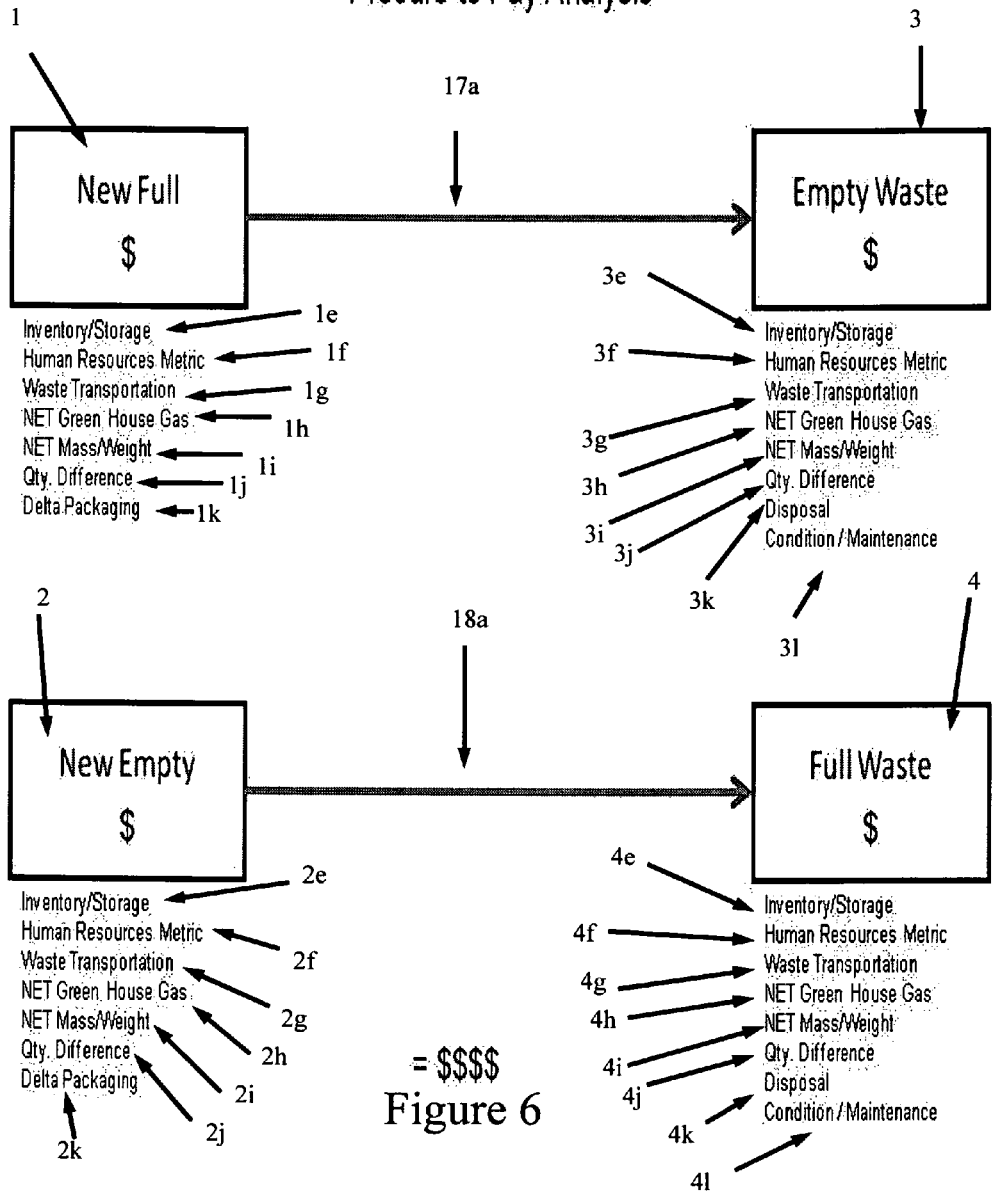
FIG. 6 shows a prior art supply chain and disposal chain apparatus and a second supply chain and disposal chain apparatus and some of the cost metrics associated with each. On a procure to pay valuation basis the cost factors shown, such as 1e-1k, 2e-2k, 3e-3l and 4e-4l as well as other metrics that are appraisable (not shown) may be appraised for each supply chain and disposal chain apparatus that is associated with a point of consumption and or a facility to obtain economic values for each.

Turning to FIG. 6.

FIG. 6 shows a prior art schematic revealing product acquisition and consumption co containers on a procure to pay appraisal basis the as an entity may procure prior art containers. Prior art enterprise resource planning and management of containers 1 and containers 2 are shown as they each respectively, separately and individually travel along their respective separate uses as they respectively flow through a facility in accordance with the prior art at 17a and 18a. New full container 1 is shown having cost associated with its procurement such as inventory/storage 1e, human resource metrics 1f, waste transportation metrics 1g, new green house metrics 1h, net mass/weight metrics 1i, quantity difference 1j, and delta packaging metrics 1k. In addition, container 1 becomes an empty waste container along 17a and has no further value which adds cost drivers associated therewith such as inventor/storage metrics 3e, human resource metrics 3f, waste transportation metrics 3g, net green house gas metrics 3h, net mass/weight metrics 3i, quantity difference metrics 3j, disposal metrics 3k, and condition/maintenance metrics 3l. In addition, newly procured empty waste collection container 2 has associated costs such as inventory/storage metrics 2e, human resource metrics 2f, waste transportation metrics 2g, net green house gas metrics 2h, net mass/weight metrics 2i, quantity difference metrics 2j, and delta packaging metrics 2k. In addition, used waste collection container 4 has associated costs such as inventory/storage metrics 4e, human resource metrics 4f, waste transportation metrics 4g, net green house gas metrics 4h, net mass/weight 4i, quantity difference 4j, disposal metrics 4k and condition/maintenance metrics 4l. This is not meant to be a complete list of metrics however the lists associated with the container conditions as in 1, 2, 3, & 4 of FIG. 6 provides enough of a representative sample to reveal the appraisal concept for the purposes of appraising the value of NuPurposing which creates the novel supply chain and disposal chain of an exemplary NuChain.

Figure 7:
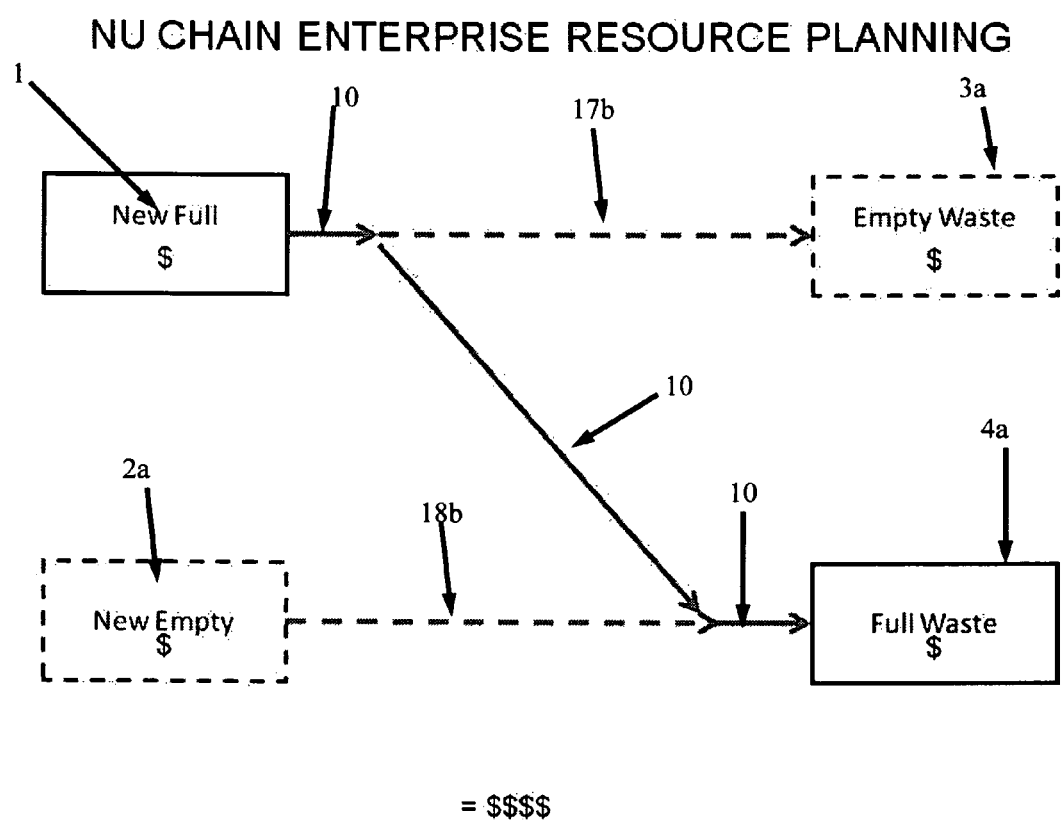
FIG. 7 shows a NuChain enterprise resource planning supply chain and disposal chain apparatus connecting two prior art supply chain and disposal chain apparatus whereby a fluent material filled product distribution container has transformed into a waste collection container and creates a new value defined as a NuChain enterprise resource planning process and NuChain supply and disposal chain apparatus.

Turning to FIG. 7.

FIG. 7 shows the NuChain enterprise resource planning supply chain and disposal chain apparatus and the elimination of the supply chain costs and the disposal chain costs with the elimination of new empty collection container procurement as depicted by the broken lines 2a and the associated supply chain apparatus costs at 18b and also defined by the cost savings of elimination of the supply chain apparatus costs 2, 2e, 2f, 2g, 2h, 2i, 2j, 2k of FIG. 6 as is depicted by broken arrow lines 2a and 18b of FIG. 7 and in addition to the elimination of the separate disposal chain apparatus costs of 3, 3e, 3f, 3g, 3h, 3i, 3j, 3k and 3l as depicted by broken lines 17b and 3a in FIG. 6 by eliminating the procurement costs of a new empty collection container and by eliminating the disposal costs of used containers going into the trash. New full collection container 1 becomes the collection container 4a as a NuPurposed container creating a NuChain supply chain and disposal chain apparatus. Container 1 is transformed and conditioned for the ingress of waste material along number 10 as marked in three placed of FIG. 7 as the NuChain supply chain apparatus and disposal chain apparatus transfer vector that connects new full container 1 with the disposal chain of fluent waste material as depicted by 4a as created by NuPurposing containers as taught by the instant case.

Figure 8:
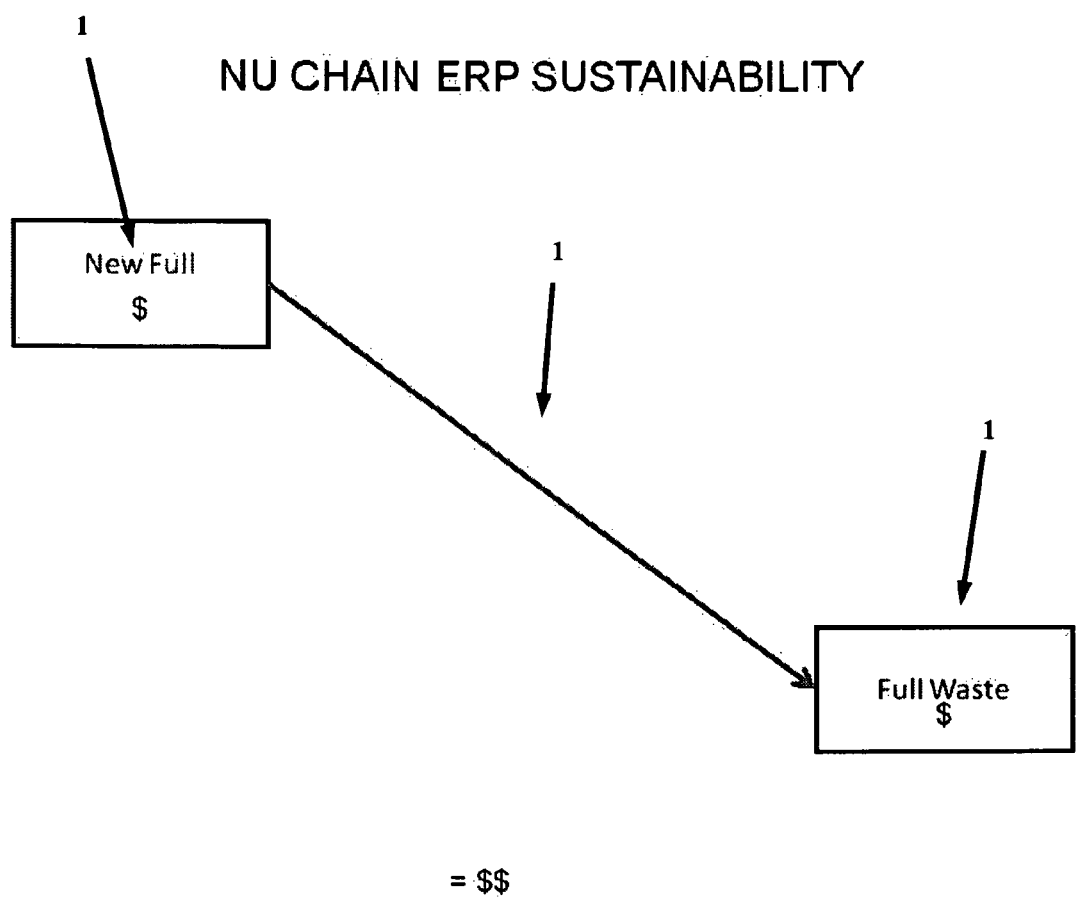
FIG. 8 shows show's a new NuChain Enterprise Resource Planning sustainability and environmentally preferred supply chain and disposal chain apparatus whereby a new filled fluent material container may be distributed to a facility and/or a point of consumption as such a container is conditioned and transformed to collect waste material.

Turning to FIG. 8.

FIG. 8 shows a direct supply chain 1 (center) connecting new full container 1 (upper left) to be conditioned and transformed to ingress waste materials 1 (lower right).

Figure 9:
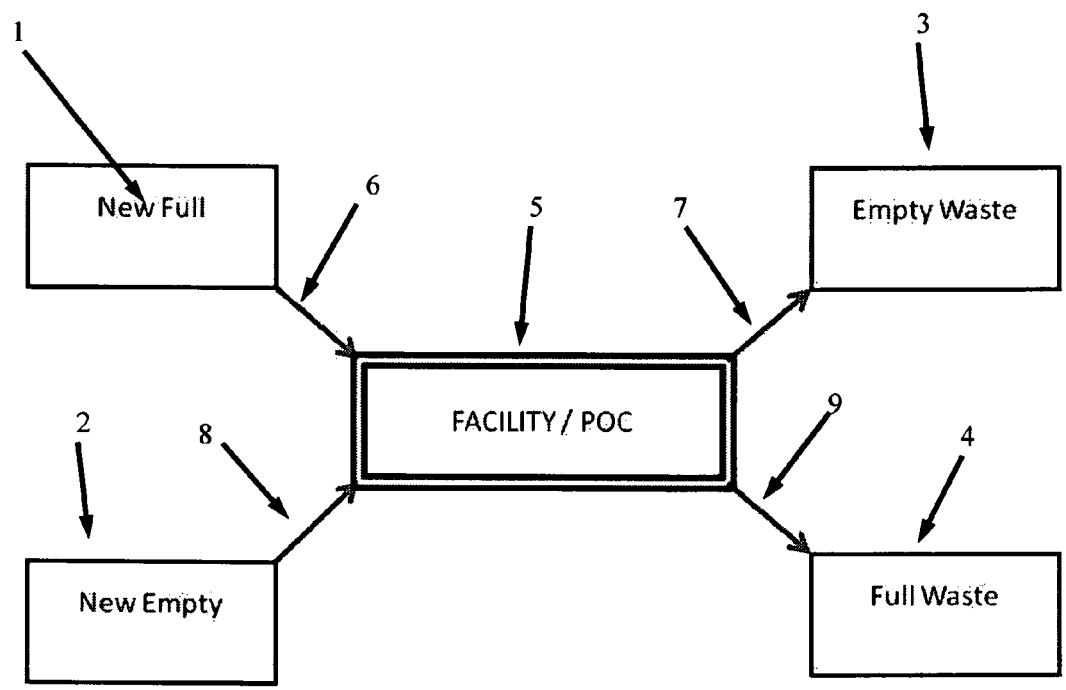
FIG. 9 shows a prior art schematic wherein a first full fluent material commercialization container and a separate second empty collection container gives rise for the need for a container transformation of the instant case and also give rise for the need for a online container trading exchange so that facilities and point of consumption may benefit from empty fluent material distribution containers being conditioned and adapted to be exchanged (not necessarily in that order of events) between departments of a facility, between point of consumption associated with various supply chain and disposal chain apparatus, and/or between separate facilities, so that a mechanism exists for users needing access to NuPurposing may acquire such, and or, may transform and condition containers for sale, and/or to find and procure containers from facilities and/or points of consumption where there may be an overabundance containers.

Turning to FIG. 9.

FIG. 9 shows the schematic of FIG. 1 and gives rise to the need of a NuChain enterprise resource planning supply chain apparatus and disposal chain apparatus online trading exchange that would benefit society by the offering and dissemination of an overabundance of containers that may not have the need to be NuPurposed in a particular facility but may be needed in another facility or by a department or subsidiary of an entity.

Figure 10:
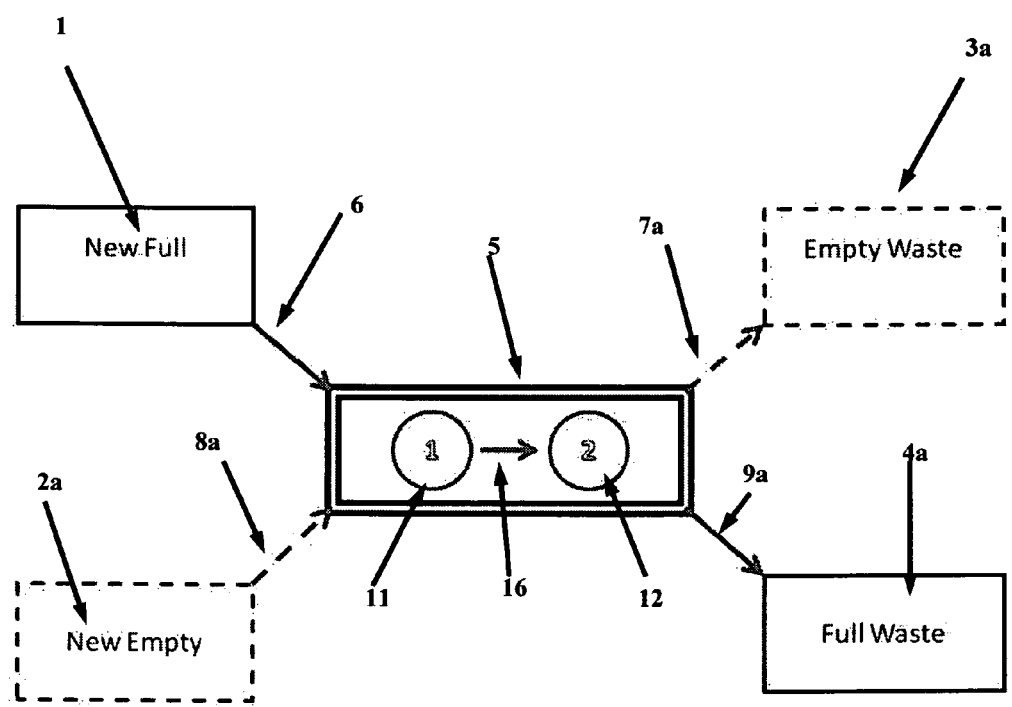
FIG. 10 shows a novel supply chain and disposal chain apparatus where the used fluent material distribution container has been transformed from a condition one-circled 1 to a condition two-circled 2 and gives rise to the need for an online exchange in the event there may be an overabundance of containers.

Turning to FIG. 10.

FIG. 10 shows the supply chain of FIG. 2 showing the elimination of 2a, 8a, 7a and 3a giving rise for the need of an online exchange for the procurement of containers where there is an overabundance of containers for NuPurposing whereby a particular facility may not have the need to NuPurpose some or all of the containers and where another facility may benefit from the procurement of and conditioning and transforming of containers NuPurposing in their separate facility. These containers are exchanged between facilities, and/or separate entities for the purposes of transforming containers into a condition for NuPurposing into waste material ingressing containers. In the event that an overabundance of containers exist and may be transformed and conditioned for a new purpose, an online exchange will allow procurers to access and procure such containers.

Figure 11:
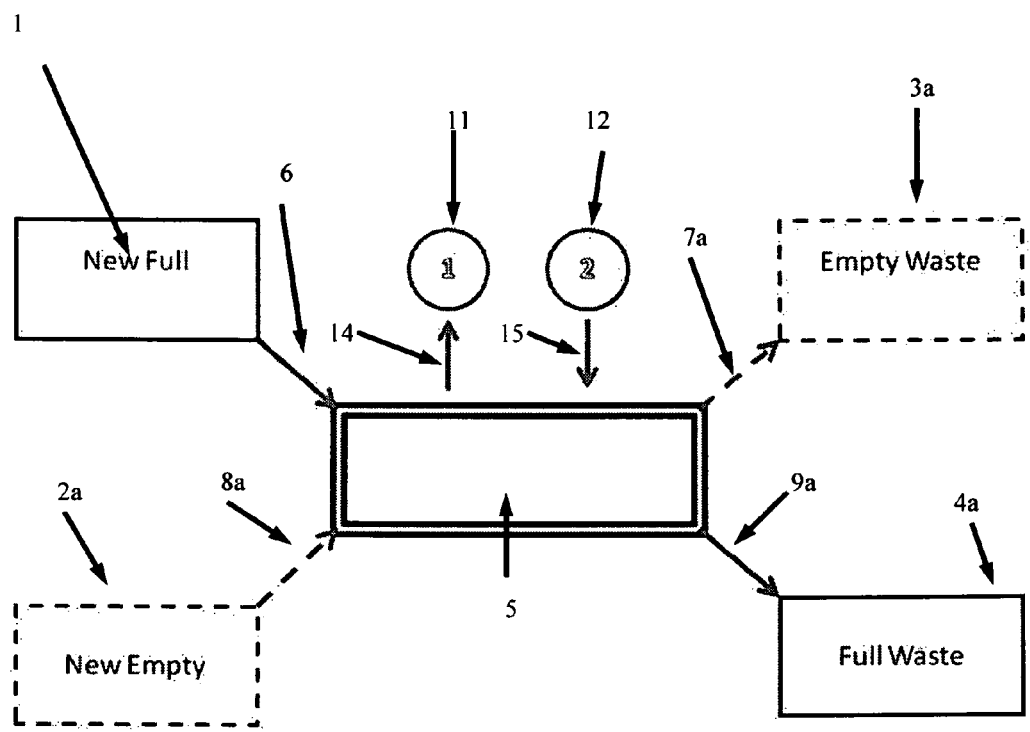
FIG. 11 shows a similar supply chain apparatus as FIG. 10 however the transformation of the new full commercialization container transforms from condition 1 to condition 2 is a process that occurs outside a facility/point of consumption as shown by transfer vectors 14 and 15.

Turning to FIG. 11.

FIG. 11 shows a NuChain supply chain and disposal chain enterprise resource planning model that teaches an online exchange user what to evaluate when considering a NuChain procurement of containers for NuPurposing in a facility that may need containers to condition for transformation into NuPurposed containers of facilities that may need to condition and transform containers for NuPurposing. This schematic gives rise to an online NuPurposing container procurement and trading exchange in the event a facility has a overabundance of containers that may be NuPurposed by another facility or in the event a facility has an inadequate supply of containers for NuPurposing at the volume levels desired and the other facility wishes to procure containers for NuPurposing to make up for the inadequate volume. The online trading exchange may be between different departments of the same facility, different departments of different facilities, between different entities, between different facilities and the like. Supply chain apparatus transfer vectors 14 and 15 show that the conditioning and or transformation of containers into a different state may be carried out by a separate facility. The online container trading exchange would allow separate facilities to become aware of and have access to the procurement of collection containers from facilities that have an abundance of collection containers without having to procure separately produced empty collection containers 2a and prevents the expense of the associated costs, as well as the supply chain costs of disposal costs at 7a and the costs of disposal of empty waste containers 3a and reduces the amount of waste introduced into the waste stream.

Figure 12:
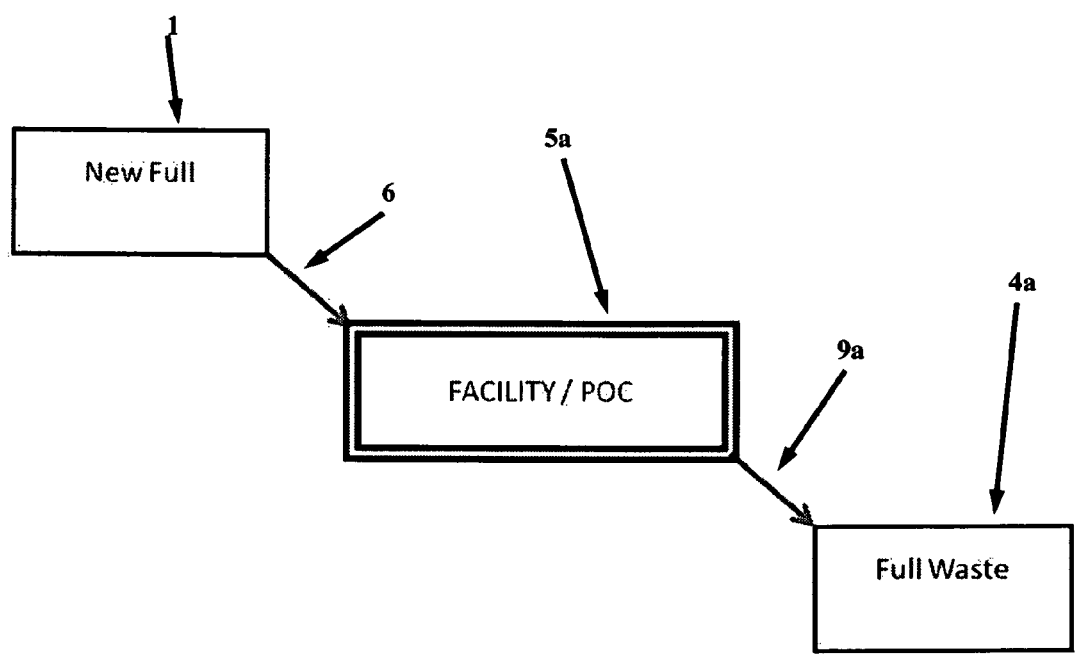
FIG. 12 is a drawing of a supply chain and disposal chain apparatus which depicts the commercialization, distribution and receiving of a new full fluent material container being received by a facility/point of consumption, being consumed at a point of consumption and then being conditioned for transformation into a waste collection container.

Turning to FIG. 12.

FIG. 12 shows the NuChain supply chain apparatus and disposal chain apparatus depicting the connection between the two separate prior art supply and disposal chains as shown in FIGS. 9, 6, 5 and 1. FIG. 12 shows a NuChain that is created by the NuPurposing of containers as taught by the instant case. NuPurposing containers creates a streamlined and cost effective practice for the delivery of new materials and for the collection of waste materials whereby container 1 is received by facility 5a along transfer vector 6 and container 1 having been conditioned and transformed into a collection container by NuPurposing leaving facility 5a as a collection container 4a. NuPurposing reduces waste. NuChain's reduce waste.

Figures 13, 14, 15:
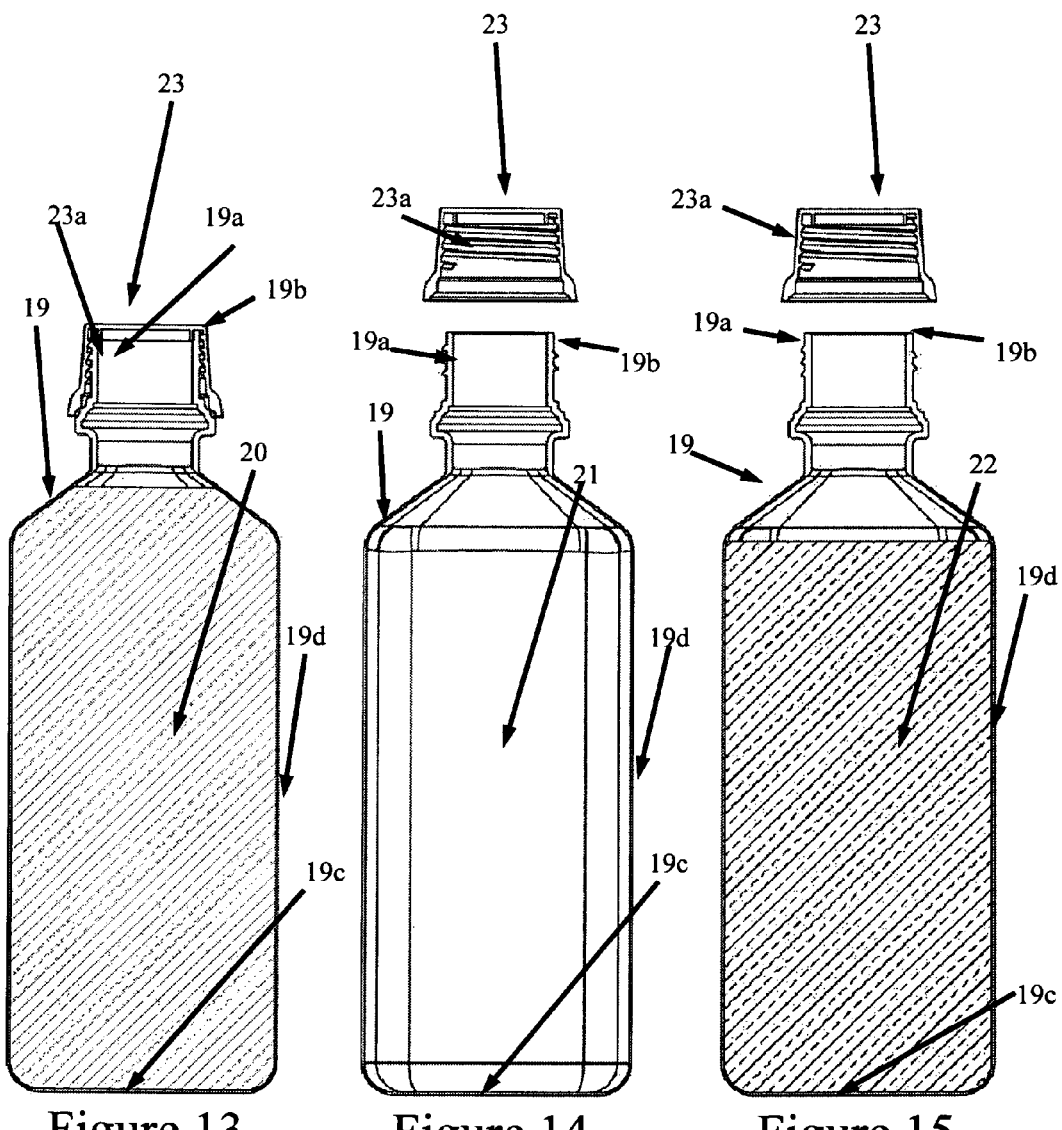
FIG. 13 is a side elevation cutaway view of a newly distributed fluent material commercialization container 19 containing unused fluent material 20.
FIG. 14 is a side elevation cut away view of a fluent material distribution container wherein at least a portion of said fluent material has egress out of said container 19 leaving cubic volume available inside 21 of container 19 for the ingress of waste material. Container 19 in FIG. 14 either has been conditioned or is in a position to be conditioned for the collection of waste materials. Cap 23 of container 19 may be held in abeyance during the conditioning and transformation of container 19.
FIG. 15 is a side elevation cutaway view of container 19 having been conditioned and transformed for the collection of waste material. The waste material 22 is seen in FIG. 15. Cap 23 may be replaced on to container 19 to provide a leak proof seal to prevent waste leakage during a disposal process of a disposal chain apparatus. It is understood that cap 23 of FIGS. 13, 14 and 15 may be the same cap or a different cap of similar construction whereas many containers are mass produced with the same dimensional specification and will serve the purpose of sealing a waste container 19 of FIG. 15. Alternative seals may be used for sealing container 19 to seal waste 22 inside container 19 as shown in FIG. 15.

Turing to FIG. 13.

FIG. 13 side elevation cutaway view showing a bottle 19 in a fluent material distribution condition. Bottle 19 is shown having a new fluent material 20 contained therein by cap 23. Cap 23 has internal threads 23a. Bottle 19 shows threads 19a and a pour spout at 19b. Bottle 19 also has an outside perimeter 19d and a bottom 19c.

Turning to FIG. 14.

FIG. 14 is a side elevation cutaway view showing bottle 19 having egressed its fluent material 20 of FIG. 13. Bottle 19 is shown having space inside available in cubic volume to ingress waste material as shown by 21. Bottle 19 is shown having cap 23 removed.

Turning to FIG. 15.

FIG. 15 is a side elevation cutaway view showing bottle 19 having ingressed waste material as shown by 22. FIG. 15 shows bottle 19 as having been bottle docked and ingressed waste materials 22.

Figure 16:
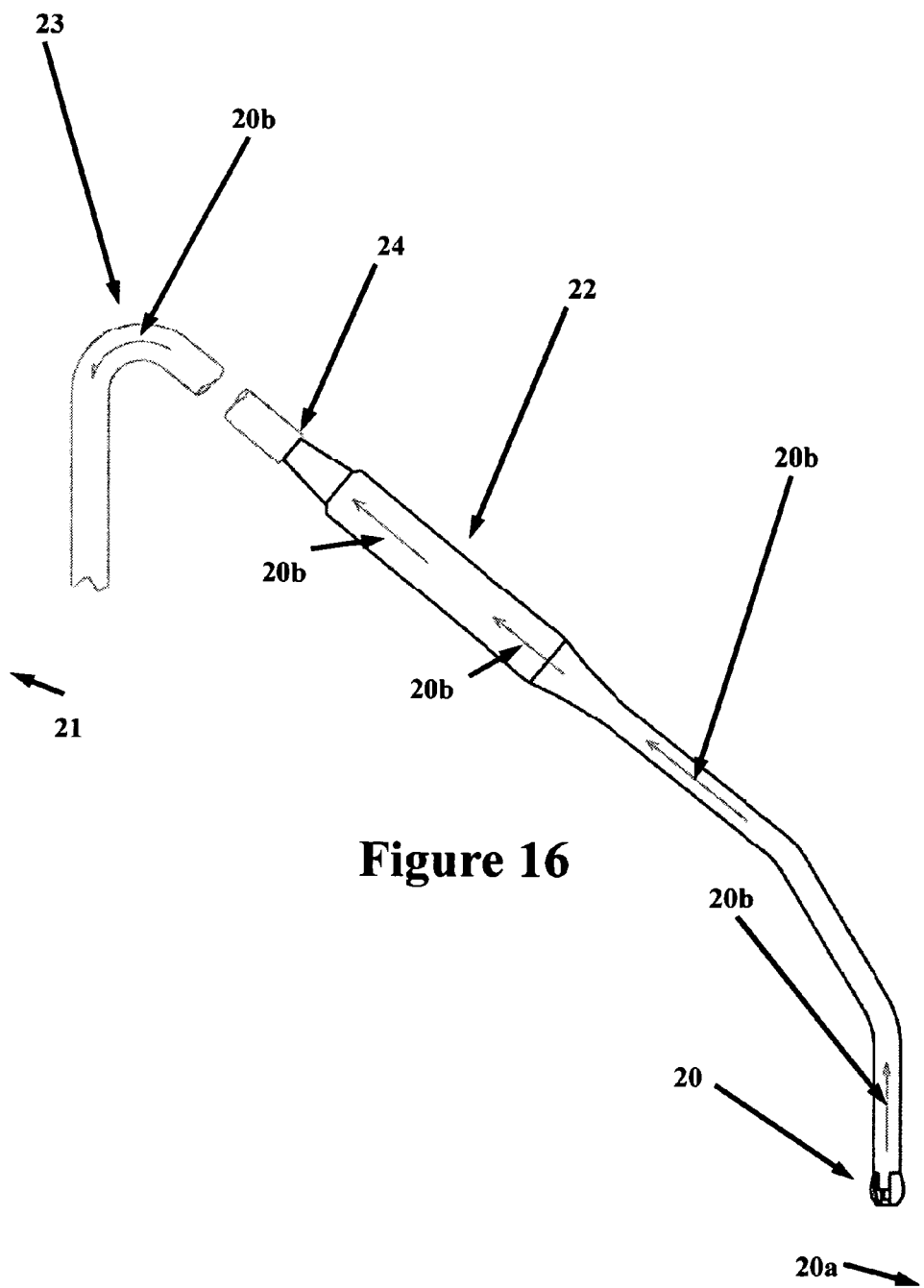
FIG. 16 is a side elevation view of a suction tip 22. Suction tips are commonly referred to as suction wands and may go by other common names such as Argyle Suction tips, Tonsil Suction tips, Pool suction tips, Adson suction tips, Frazier tips, suction and aspiration devices and the like etc. etc. The suction tip as shown in connection with a suction tubing 23 are commonly connected to form a conduit for waste material being drawn from a source of waste material into collection container such as container 19 as taught by the instant case. Said conduits are commonly used in many forms of care such as open surgery, and other procedures such as arthroscopic surgery, endoscopic procedures, robotic surgery, minimally invasive procedures, computer assisted surgery as well as such conduits are used in procedures that are performed on all parts of a human or animal.

Turning to FIG. 16.

FIG. 16 is a side elevation view showing a suction tip commonly known in the art as a suction wand showing a connection 24 to a suction tubing 23. Number 21 represents a source of reduced pressure which draws negative pressure from suction tip 22 at 20 along the arrows 20b shown in five places as the negative draw pressure draws waste material from a source of waste at 20a and along the conduit formed by the tip and tubing as the arrows are depicted in five places of FIG. 16 which passes through the connection 25 and through the suction tubing 20b toward a canister for the deposit of waste material whereby negative draw force at 21 pulls vacuum forces that draw waste materials into canister 25 and or bottle 19. conduit 23 may connect to a bottle plug (not shown) through the lid 26 at 26j, or connect to lid port 26k.

Figure 17:
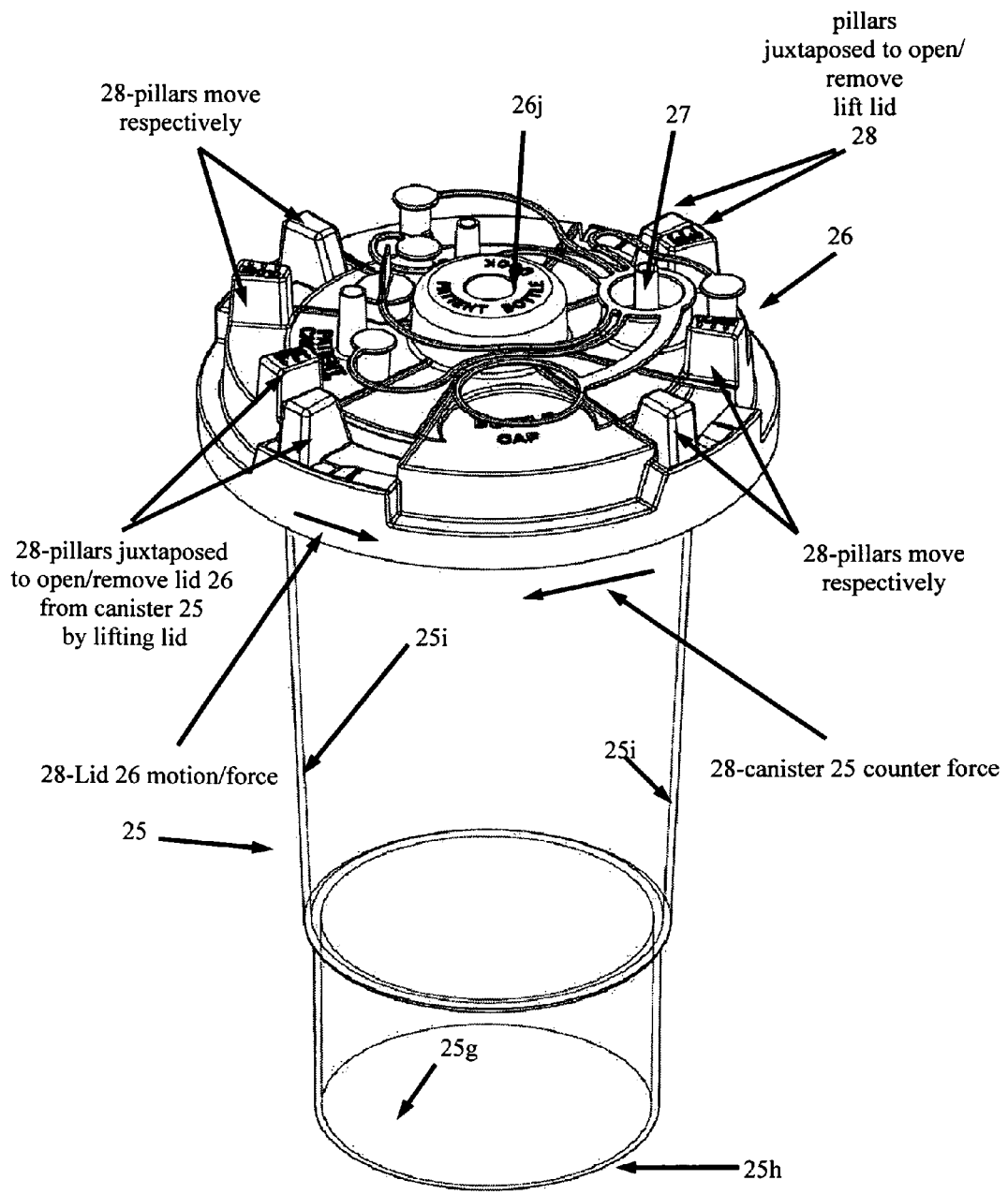
FIG. 17 is a top isometric view of a bottle docking suction canister system conditioned to operate as normal suction canister in the instance where no bottles are available or desired to dock inside the system.

Turning to FIG. 17.

FIG. 17 is a top isometric view showing the bottle docking system as taught by the instant case assembled in the operative mode of an ordinary suction canister without bottle docking a bottle 19 inside. Lid 26 is shown in the spatial and temporal process of being assembled to canister 25. Capping member 27 is disposed accordingly on lid 26. Canister pillars 25b1, 2, 3, & 4 of FIG. 25 can be seen projecting up through lid pillar apertures 26h1, 2, 3, & 4 of FIG. 21. Lid aperture 26j is shown unplugged, however during use as an ordinary suction canister would be plugged by cap member 27k of FIG. 18. Also cap member 27c of FIG. 18 would be capped. Canister 25 is shown having an outside bottom 25h and an inside bottom 25g. Canister 25 is shown having inside walls in two places at 25i.

Turning to FIG. 18.

FIG. 18 is a top isometric view of capping member 27. Capping member 27 comprises cap 27c which caps tubing port 27 of 27b. Cap 27 also comprises a plurality of retainers. Retainer 27f positions and retains cap 27c. Retainer 27o positions and retains lid lock 27a. Retainer 27j positions and retains cap 27i. Retainer 27l positions and retains cap 27k. Retainer 27p positions and retains cap 27m. Retainer 27h positions and retains bottle cap ring holder 27g. Plug 27b plugs lid pour spout 26p and positions all aspects of cap member 27 with respect to features of lid 26. Plug 27b is sized and shaped to fit and plug lid pour spout 26p of lid 26. Lid lock 27a retained and positioned for easy depression into lid lock hole 26i of lid 26. Cap 27i is retained and positioned to cap vacuum tubing port 26l of lid 26. Lid plug cap 27k is retained to plug center lid aperture 26j. Cap 27m is retained and positioned to cap patient tubing connection port 26k of lid 26.

Turning to FIG. 19.

FIG. 19 is a top isometric view of lid 26 showing the detailed features of lid 26. Lid 26 comprises four lid pillars 26a1, 2, 3, & 4. 26i represents the lid lock hole. 26k comprises the suction tubing connection port for a patient suction tubing. 26l comprises a suction tubing connection port for a source of vacuum. 26p comprises a pour spout. 26j comprises a center aperture for a patient suction tubing to be used during a bottle docking mode of operation by connection to a patient tubing connection on a bottle plug (not shown). 26h1, h4, h3, & h2 each comprise an aperture for acceptance passage and movement of canister pillars 25b1, 2, 3, & 4. 26f1, 2, 3, & 4 comprise an ascending sealing ramp that is positioned to contact the bottom side 25b1e, 2e, 3e & 4e of canister pillars 25b1, 2, 3, & 4. Ultimately when in the fully compressed condition lid contact surfaces 26g1, 2, 3, & 4 engage in contact with canister pillar bottom edge 25b1h, 2h, 3h & 4h as counter rotational motion between canister 25 and lid 26 compresses lid 26 and canister 25 together to form a seal therebetween at lid 26o of FIG. 25 and canister 25d of FIG. 20.

Turning to FIG. 20.

FIG. 20 is a top isometric view canister 25. Canister 25 comprises canister pillars 25b1, 2, 3, & 4. 25c1, 2, 3, & 4 comprise the lid lift ramp. 25a1, 2, 3, & 4 comprise canister and lid lock hole. Flat surface 25e marked in four places comprises the top flat contact surface for contact between lid 26 and canister 25. 25d marked in three places shows the canister seal that seals with lid seal 26o as shown in FIG. 24. Canister seal is disposed at the top of the inside rim of canister 25 for sealing canister 25 for sealing with the annular lid seal 26o of lid 26 as shown in FIG. 24.

Figure 21:
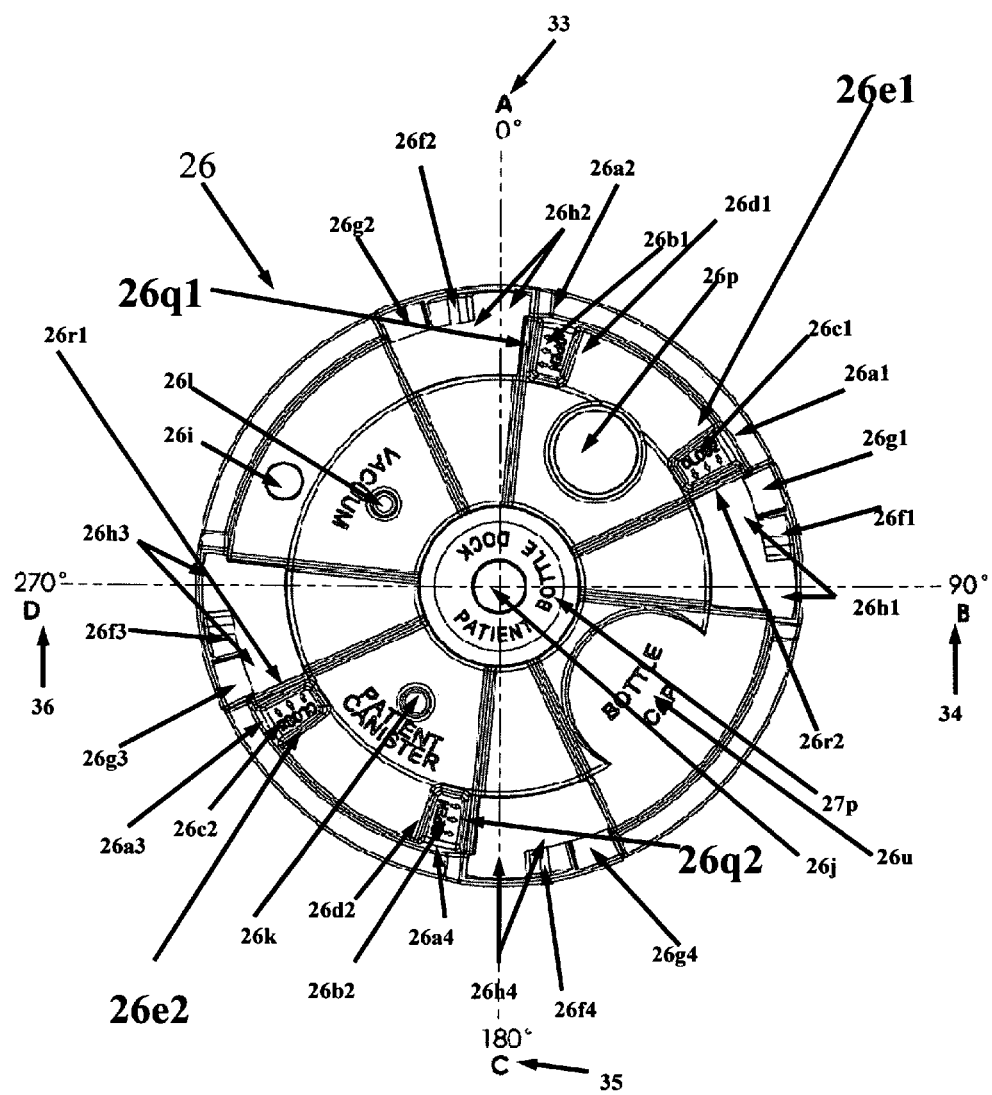
FIG. 21 is a top plan view of lid 26.

Turning to FIG. 21.

FIG. 21 is a top plan view of lid 26. FIG. 21 shows coordinates 33 A at 0, 34 B at 90, 35 C at 180 and 36 and D at 270 forming an x-y coordinate plane with cross hairs intersecting the center of lid aperture hole 26j. Lid pillars are shown at 26a1, 2, 3, & 4. Lid locking hole is shown at 26i. Tubing connection port for a source of reduced pressure is shown at 26l. Suction tubing port connection is disposed to draw waste material from a patient and/or source of waste to go into the canister when operating as a canister showing 26k. The canister pour spout is located at 26p. Canister pillar apertures are shown at 26h1, 2, 3 & 4. Canister bottom sealing surface is shown at 26g1, 2, 3, 4. Canister pillar ascending ramp is shown at 26f1, 2, 3, & 4. Lid pillar indicia at 26c1, 26c2 show the indicia "CLOSED" with each pillar depicting three arrows showing the direction of motion/force in which pressure should be applied on lid pillar sides 26e1 and 26e2 in order to rotate, close and seal the lid 26 and canister 25 with respect to the respective lid and canister pillars to move the pillars according to the indicia on top of the pillars. Indicia shown at 26b1 and 26b2 each depicting the indicia "OPEN" and each having the three arrows on each lid pillar depicting the sides 26d1 and 26d2 of lid pillars 26a2 and 26a4 showing which sides of the lid pillars 26a2 and 26a4 pressure should be exerted to open and unseal the canister and lid. 27p shows the upwardly projecting lid boss making clearance for the bottle neck and plug. 26u shows the place on the lid where the bottle cap may be placed and retained by cap retaining ring 27tg of capping member 27.

Turning to FIG. 22.

FIG. 22 is a side elevation blow up cutaway of the circled portion of FIG. 23 which depicts the ascending canister pillar compression ramps 26f1, 2, 3, & 4. Also shown in this blowup of FIG. 22 is the canister pillar bottom sealing surface 26g1, 2, 3, & 4.

Turning to FIG. 23.

FIG. 23 is a side elevation view of lid 26 with the cutaway of the lid ascending sealing ramp 26f1, 2, 3, & 4 and canister pillar bottom sealing surface 26g1, 2, 3, & 4. Also depicted are the annular outside lid skirt 26y marked in two places as well as the upwardly projecting bottle neck/plug 65 clearance boss 27p.

Turning to FIG. 24.

FIG. 24 is a bottom plan view of lid 26. The annular canister sealing surface 26o is shown. Canister struts 26n1, 2, 3, 4, 5, 6, 7, & 8 can be seen in 8 places. Annular lid plug seal can be seen at 26x. Center lid aperture 26j allows connection access to bottle plug (not shown) and patient suction tubing connection can be seen at 26j. The lid 26 annular skirt can be seen at 26y. 26s1, 2, 3, & 4 comprise rotational riding rails for each of the canister pillars 25b1, 2, 3, & 4 as the lid is located, rotationally registered, and placed on canister 25, lid 26 pillars 25b1, 2, 3, & 4 may be rotated contacting lid rails 26s1, 2, 3, & 4 until such relationship exists whereby the canister pillars are under aperture spaces 26h1, 2, 3, & 4 whereby the lid drops down onto the canister as the lid pillars 25b1, 2, 3, & 4 pass thorough the lid pillar apertures 26h1, 2, 3, & 4. The canister pillars contact the lid rails and the canister pillars slidably engaged the lid rails and are in contacting registration engagement until the canister pillars then drop through lid apertures 26h1, 2, 3, & 4 to begin the counter rotational sealing action between lid 26 and canister 25. The upwardly projecting lid bottle neck clearance boss can be seen at 27p. 26l comprises the suction tubing connection port for the source of reduced pressure. Suction tubing connection port for the patient suction tubing (for the canister only mode of operation, e.g. not for a bottle docking mode of operation) can be seen at 26k. Lid lock hole can be seen at 26i. Hydrophobic filter press fit struts can be seen at 26m1, 2, & 3 to protect the reduced pressure tubing and negative pressure source system that draws negative pressure into the canister system through tubing connection port 26l from systems materials. Also shown at a radius center point just inside the perimeter of upwardly projecting bottle neck/plug clearance boss 27p are lid struts 26n1, 2, 3, 4, 5, 6, 7, & 8 which take an upward projecting angle to act as a funnel guide, or a chamfer guide to create a precision seal fit between annular plug seal 26x and bottle plug (not shown).

Figure 25:
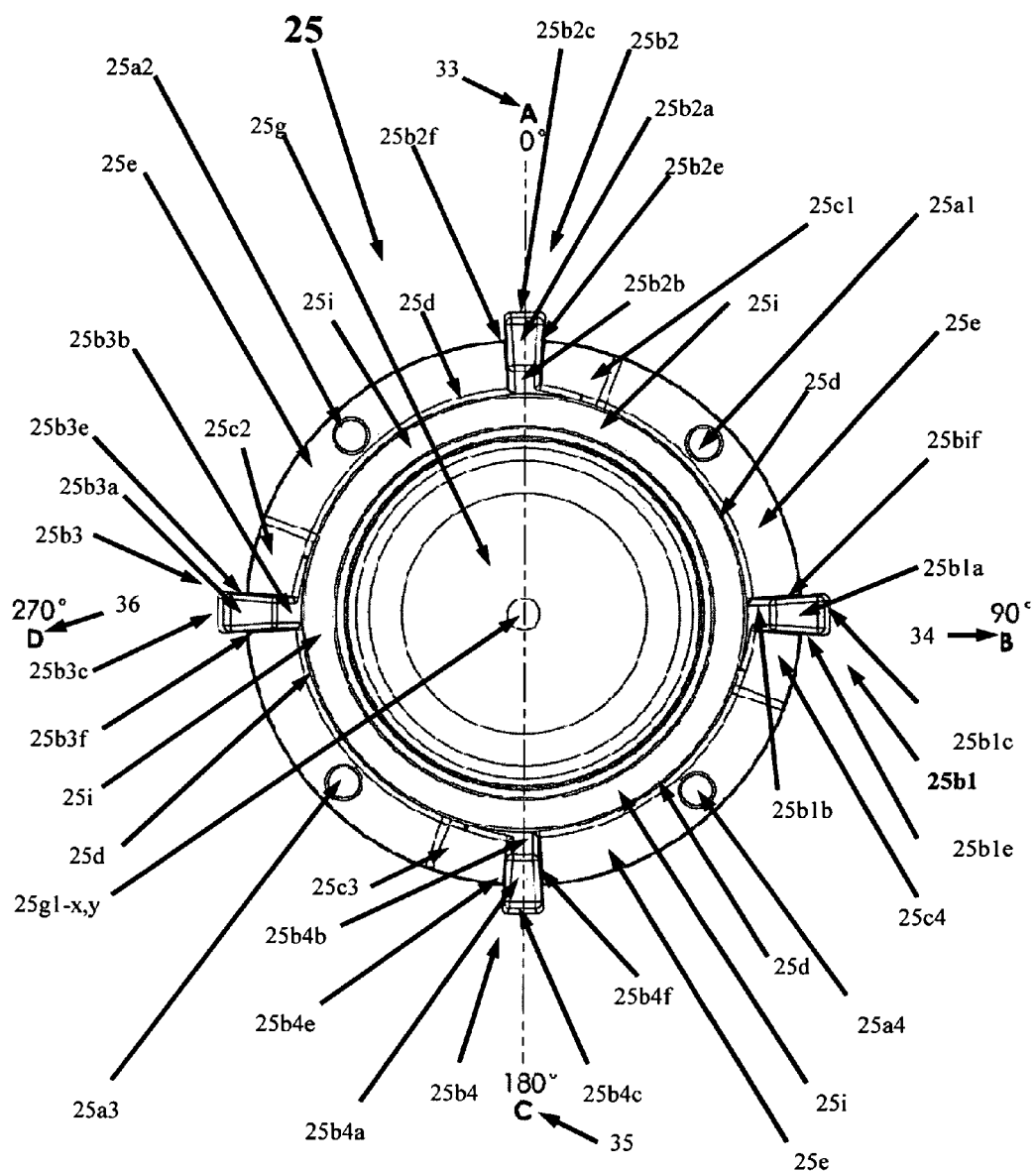
FIG. 25 is a top plan view of canister 25.

Turning to FIG. 25.

FIG. 25 is a top plan view of canister 25. Canister pillars are shown at 25b1, 2, 3, & 4. Canister locking holes are shown at 25a1, 2, 3, & 4. Canister sealing surface is shown at 25d in four places. An x,y coordinate plane is shown by 33a at 0 degrees, 34b at 90 degrees 35c at 180 degrees, and 36d at 270 degrees. The lines a-c and d-b intersect at cross hairs in the center of canister 25 as shown by 25gl-x,y. The inside wall of canister 25 is marked at 25i in four places. Canister top sealing surface at 25e is shown in four places. The canister unsealing ramp is shown at 25c1, 2, 3, & 4. Canister pillar top is shown at 25b1 a, 2a, 3a & 4a. It is the top of these canister pillars at the outside portion of 25b1a, 2a, 3a &b 4a that make slidably engagement contact with and ride on the composite annular sliding rails as shown in the lid bottom plan view of FIG. 24 at 26s1, 2, 3, & 4. The canister pillar inside angle is shown at 25b1b, b2b, b3b & b4b. Canister pillar outside angle is shown at 25b1c, 25b2c, 25b3c and 25b4c. Canister pillar side 25b1e, 25b2e, 25b3e and 25b4e are intended for force being placed thereon against canister pillar 25b1, b2, b3 and b34 to be moved in one direction. Canister pillar side 25b1f, 2f, 3f and 4f are intended to have force placed thereon to be respectively oriented to resist and or be adapted to be in the opposite rotational direction. The inside bottom of canister 25 is shown at 25g.

Figure 26:
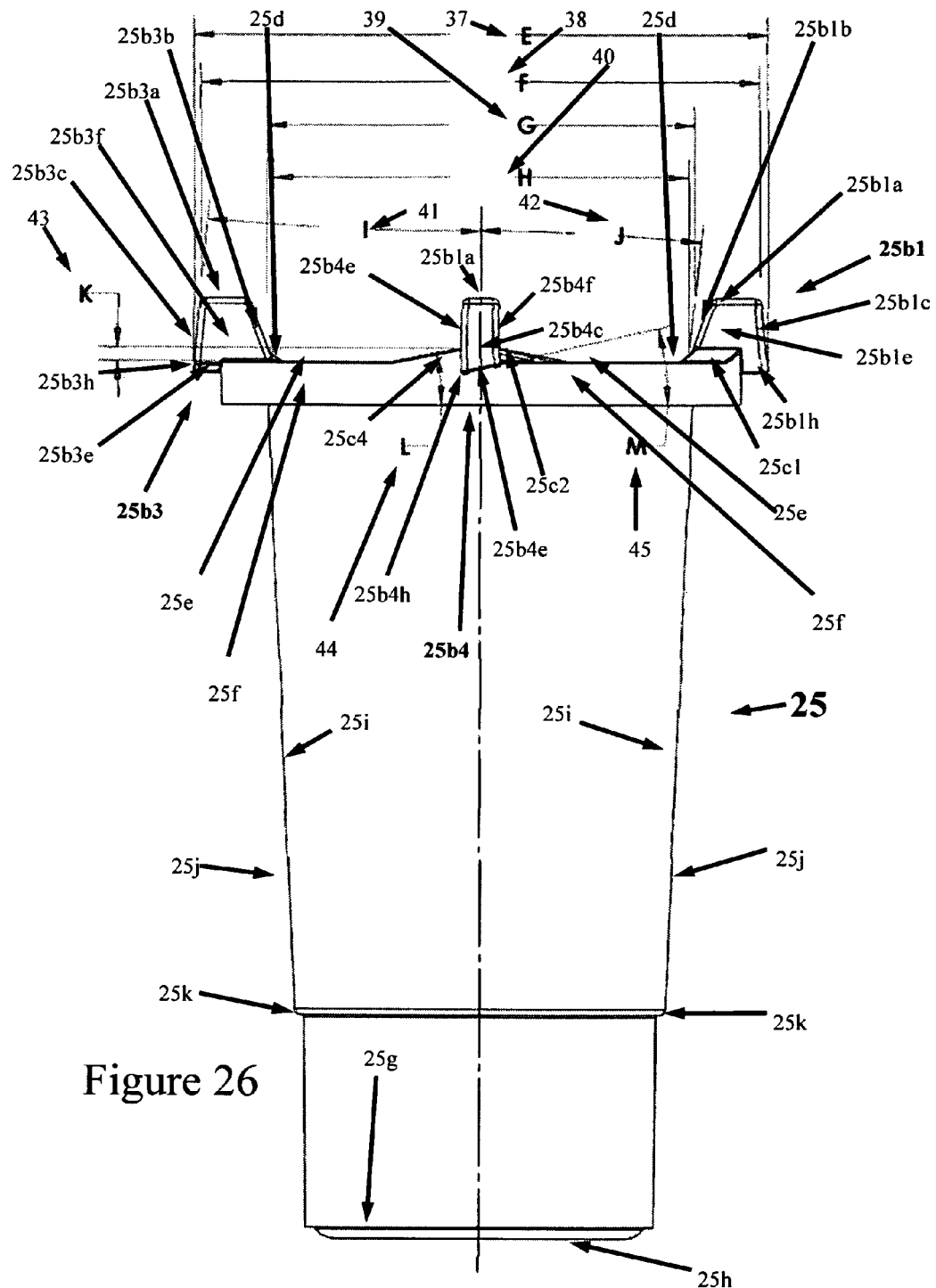
FIG. 26 is a side elevation view of canister 25.

Turning to FIG. 26.

FIG. 26 is a side elevation view of canister 25. The outside bottom canister 25 is shown at 25h. The inside bottom of canister 25 is shown at 25g. The stacking separation ridge is shown at the outside of the canister at 25k at two places. The outside ascending wall of canister 25 is marked at 25j in two places. The inside ascending wall of canister 25 is marked at 25i in two places. The top sealing lid surface of canister 25 is marked at 25e in two places. The annular lid sealing surface of canister 25 is marked at 25d in two places. Canister pillars 25b1, 25b3 and 25b4 are shown. Canister pillar 25b2 is hidden behind canister pillar 25b4. Canister pillar top is shown at 25b1a, 25b3a, 25b4a. Canister pillar top 25b2a is hidden behind canister pillar 25b4. Canister pillar inside angle 25b1b and 25b3b are marked in two places and are represented by canister pillar bottom compression ramp 25b4e and 25b3e are marked in two places and are represented by angle M at 45. Canister pillar outside angle 25b1c and 25b3c and 25b4c are marked at three places and are represented at an angle of 5 degrees L at 41. Canister lid sealing surface 25d is shown as an annular top inside rim surface of the inside of canister 25 and is represented by angle J at 42. Canister pillar side pressure surfaces can be seen at 25b3f and 25b4f. Canister side pressure surfaces are shown at 25b1e and 25b4e. Lid unsealing, lowering and sealing registration ramp is shown at 25c1, 25c2 and 25c4 and are represented by angle L at 44. Lid unsealing, lowering and sealing registration ramp 25c3 is hidden on the back side of canister pillar 25b3. Canister pillar bottom lid contact sealing surface 25b1h, 25b3h and 25b4h can be seen at three places. Downwardly projecting annular canister skirt can be seen at 25f. The height of lid unsealing, lowering and sealing registration ramp is shown at 25b3h. The distance between the outermost lower portion of outside pillar angle of 25b1 and 25b3 can be seen as E at 37. The uppermost portion of the outside angle of canister pillar 25b1, 25b3 can be seen at F at 38. The lower portion of canister pillar inside angle of canister pillar 25b1 and 25b3 can be seen as G at 39. The diameter of annular lid sealing surface 25d of canister 25 can be seen as measurement H at 40.

Figure 27:
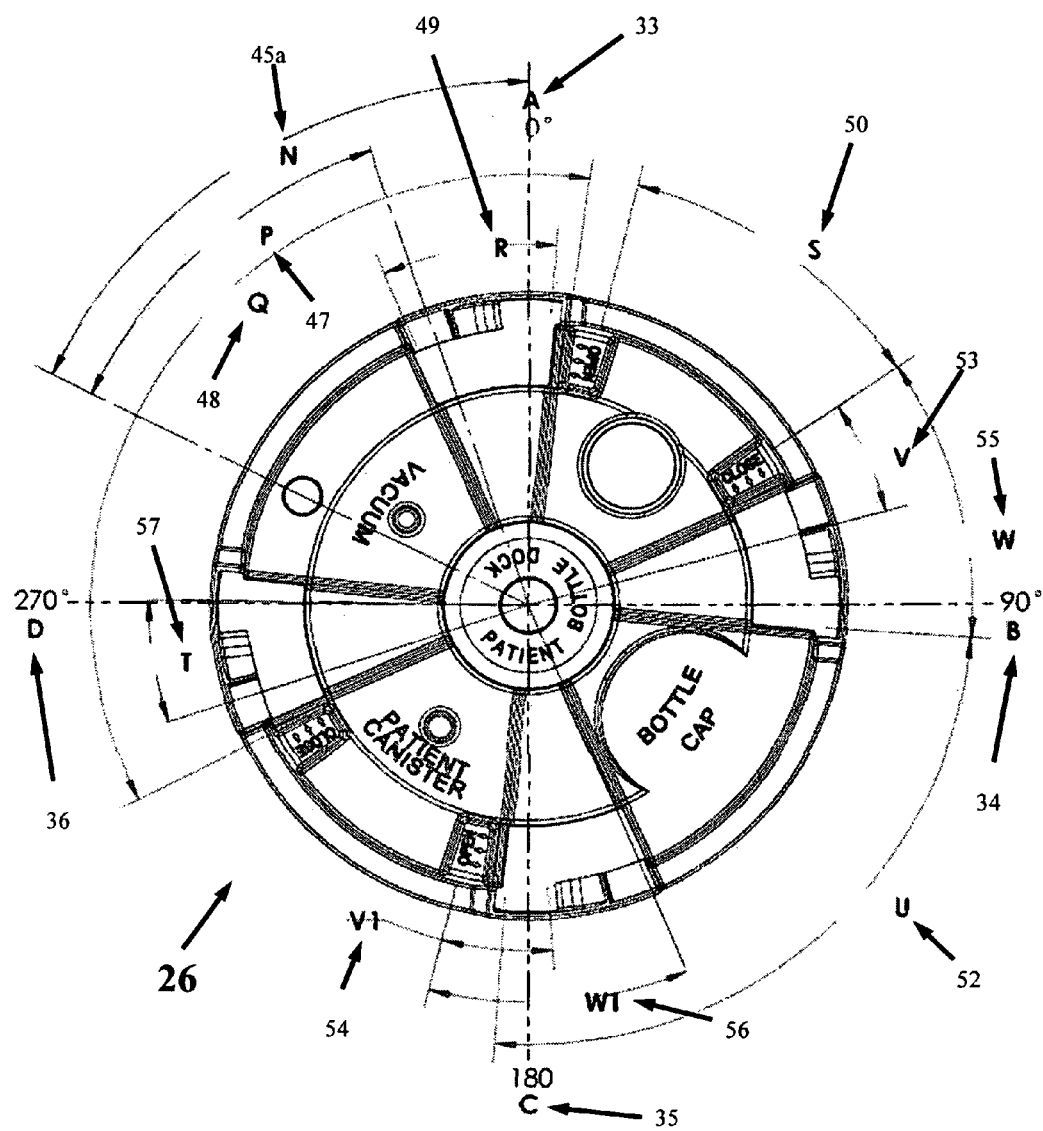
FIG. 27 is a top plan view of lid 26 showing the various features of lid 26 and where such features are arranged with respect to arcs and radians that may form a 360 degree circle. The spatial and temporal arrangements of lid 26 and canister 25 are operated by the sealing and unsealing of lid 26 and canister 25 based on the arrangements of said features.

Turning to FIG. 27.

FIG. 27 is a top plan view of lid 26. It understood arcs of FIG. 27 may be in plurality with respect to lid 26. FIG. 27 shows an x,y coordinate plane system and A defines degrees shown at 33, B defines 90 degrees shown at 34, C defines 180 degrees shown at 35 and D defines 270 degrees shown at 36. S defines an arc shown at 50 which represents an arc that begins substantially at the center of lid pillar 26a1 and extends substantially to the center of lid pillar 26a2. Letter V defines an arc which is shown at 53 which represents an arc that begins substantially at the center of lid pillar 26a1 and extends substantially to the opposite end of canister pillar bottom seal surface 26g1. Letter W defines an arc shown at 55 which represents an arc beginning at one end of canister pillar pass through lid aperture 26h1 and extends substantially to the center of lid pillar 26a1. Letter U defines an arc shown at 52 which begins substantially at one end of canister pillar pass through lid aperture 26a and extends substantially to canister pillar aperture 26h4. The clockwise facing sides of 26h1 and 26h4 are shown. Letter W1 defines an arc shown at 56 which begins substantially at the center of lid pillar 26h4 and extends substantially to the end of the counterclockwise facing end of lid aperture 26h4. Letter V1 defines an arc beginning at one end of an intermediate portion of lid pillar 26b2 and extends substantially to the other end of the counterclockwise facing end of ascending lid ramp 26f4. Letter R defines and arc shown at 49 which begins substantially at the clockwise facing side of canister pillar aperture 26h2 and extends substantially to the counterclockwise facing side of canister pillar aperture 26h2. Letter N defines an arc shown at 45a beginning at the center of lid locking hole 26i and extends substantially to letter a-zero degrees shown at 33. Letter P defines an arc shown at 47 which begins substantially at the center of lid lock hole 26i and extends substantially to an intermediate point along lid pillar bottom sealing surface 26g2. Letter Q defines a arc shown at 48 which begins substantially at the center of lid lock hole 26i and extends substantially to counterclockwise facing surface of lid pillar side 26q1. Letter T defines an arc shown at 57 begins substantially at D 270 degrees shown at 36 and extends substantially along an intermediate portion of the surface of lid pillar bottom sealing surface 26g3.

Figure 28:
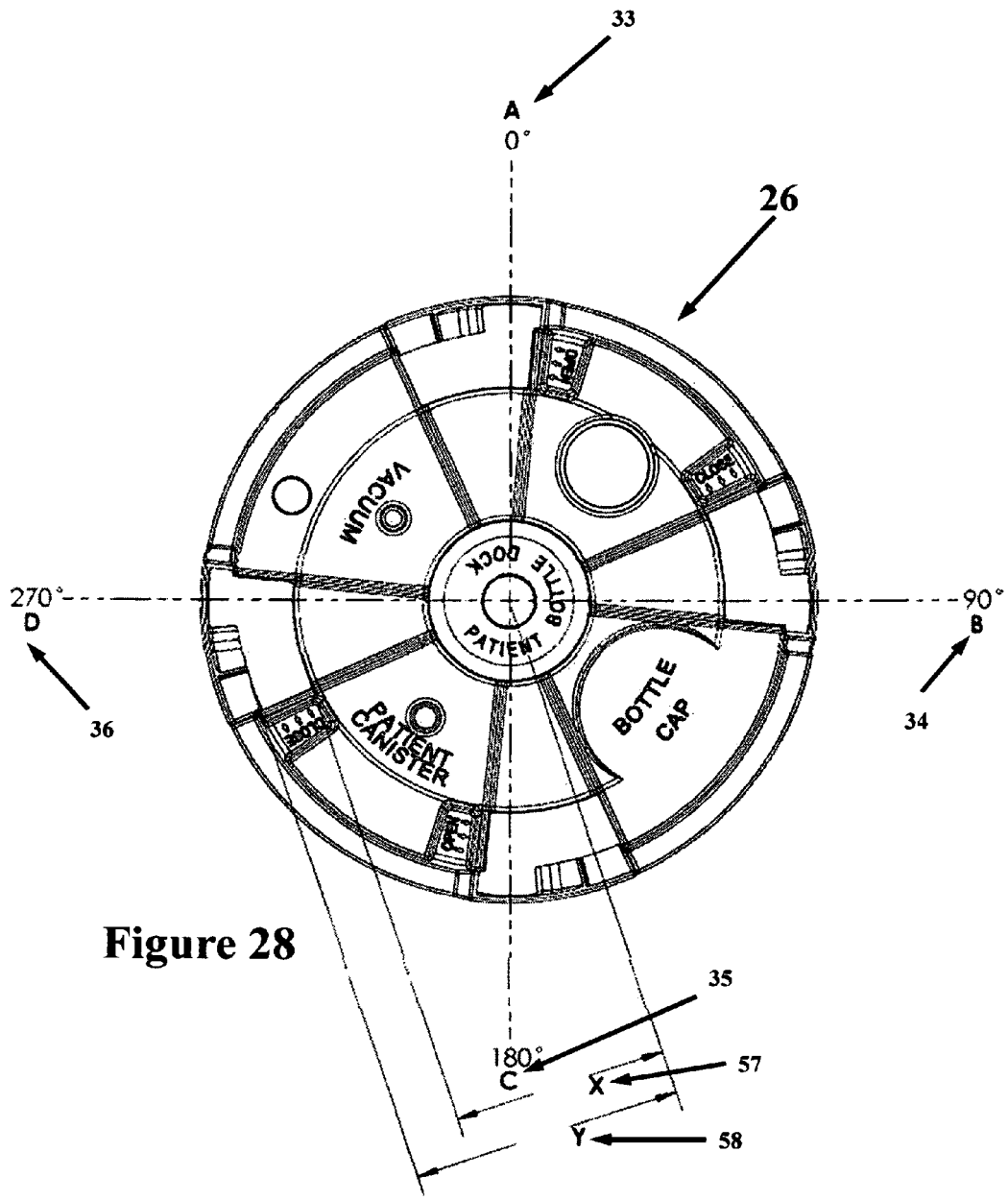
FIG. 28 is a top plan view of lid 26 showing the radiuses of lid pillars which define moment lever distances relative to the center of and with respect to other features of lid 26 and canister 25.

Turning to FIG. 28.

FIG. 28 is a top plan view of lid 26. Letter Y shown at 58 which defines a dimension beginning at the cross hairs where line AC and line BD are shown crossing substantially at the center of lid aperture 26j and extends substantially to the outside surface of lid pillar 26a1, 26a2, 26a3 and 26a4. Letter X shown at 57 defines a dimension beginning at the cross hairs where line AC and line BD cross substantially at the center of lid aperture 26j and extends substantially to the inside facing surface lid pillars 25a1, 25a2, 25a3 and 25a4. It is understood that arcs of FIG. 28 may be in plurality with respect to lid 26.

Figure 29:
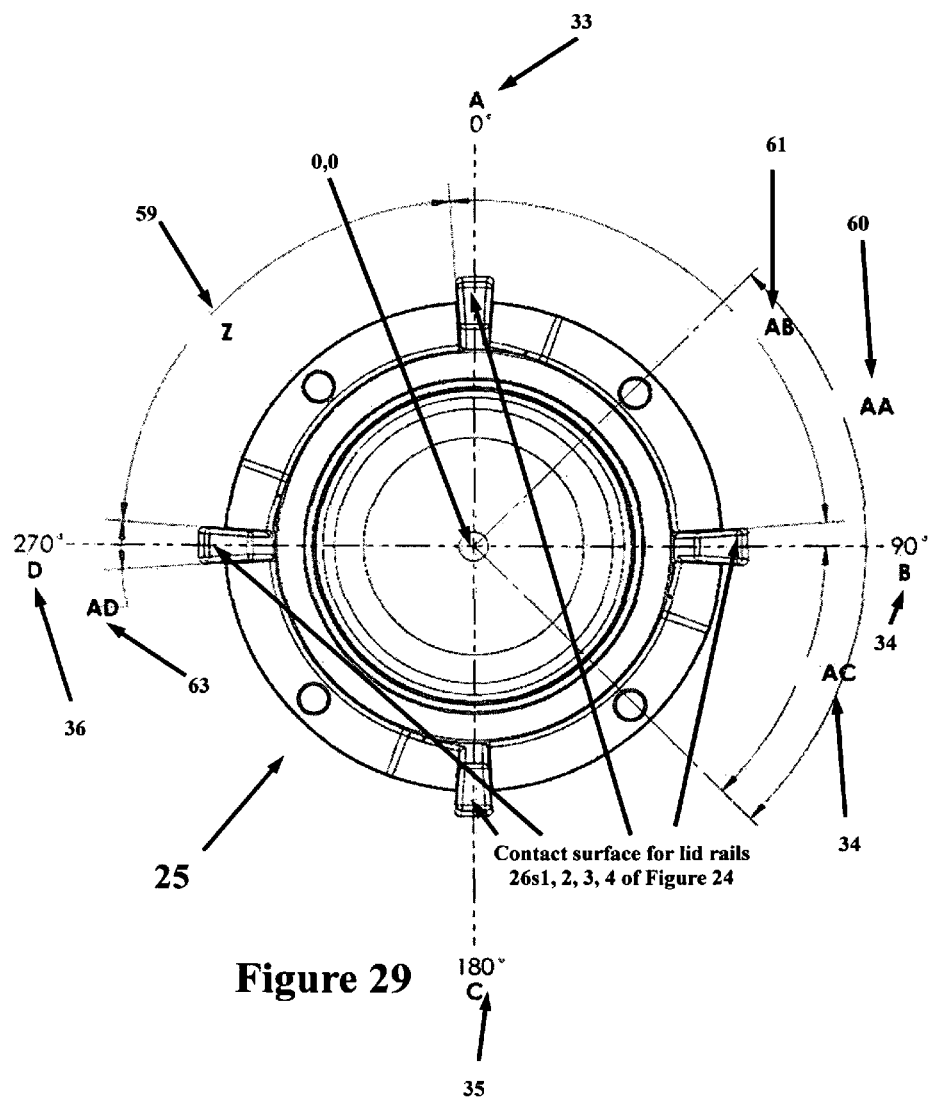
FIG. 29 is a top plan view of canister 25 showing radiuses and arcs of various features of canister 25 depicting the structural arrangements of canister 25 features that interface with lid 26. Said features operate to form a seal between lid 26 and canister 25. During the bottle docking mode of operation, said features also operate to form a seal between a bottle, a bottle plug 65 and lid 26.

Turning to FIG. 29.

FIG. 29 is a top plan view of canister 25. It is understood that arcs of FIG. 29 may be in plurality with respect to canister 25. Letter A references zero degrees shown at 33. Letter B references 90 degrees shown at 34. Letter C references 180 degrees shown at 35. Letter D references 270 degrees shown at 36. O,O reference the x,y coordinate plan defining the cross hairs where line AC and line BD cross located substantially at the center of canister 25. Letters AB defines an arc shown at 61 which begins substantially at the center of canister lock hole 25a1 and extends substantially to clockwise facing side of canister pillar 25b1f of canister pillar 25b1 of canister 25. Letters AA shown at 60 defines an arc shown at 69 which begins substantially at the center of canister lid lock hole and extends substantially to the center of an adjacent canister lid lock hole. Letters AC defines an arc shown at 34 which begins substantially passing through the center of canister pillar 25b1 and extends substantially to the center of canister lid lock hole 25a4. Letter Z defines an arc shown at 59 begins substantially at the clockwise facing side of canister pillar 25b2f and extends substantially to the counterclockwise facing side of canister pillar 25b3e of canister pillar 25b3 of canister 25. Letters AD defines an arc shown at 63 which begins substantially at the counterclockwise facing side of canister pillar 25b3e and extends substantially at the clockwise facing side of 25b3f of canister pillar 25b3 of canister 25. It is understood that the features shown associated with the values of the distances, angles, arcs and radians of FIGS. 26, 27, 28 & 29 may be modified without departing from the scope of the attached claims.

Figure 30:
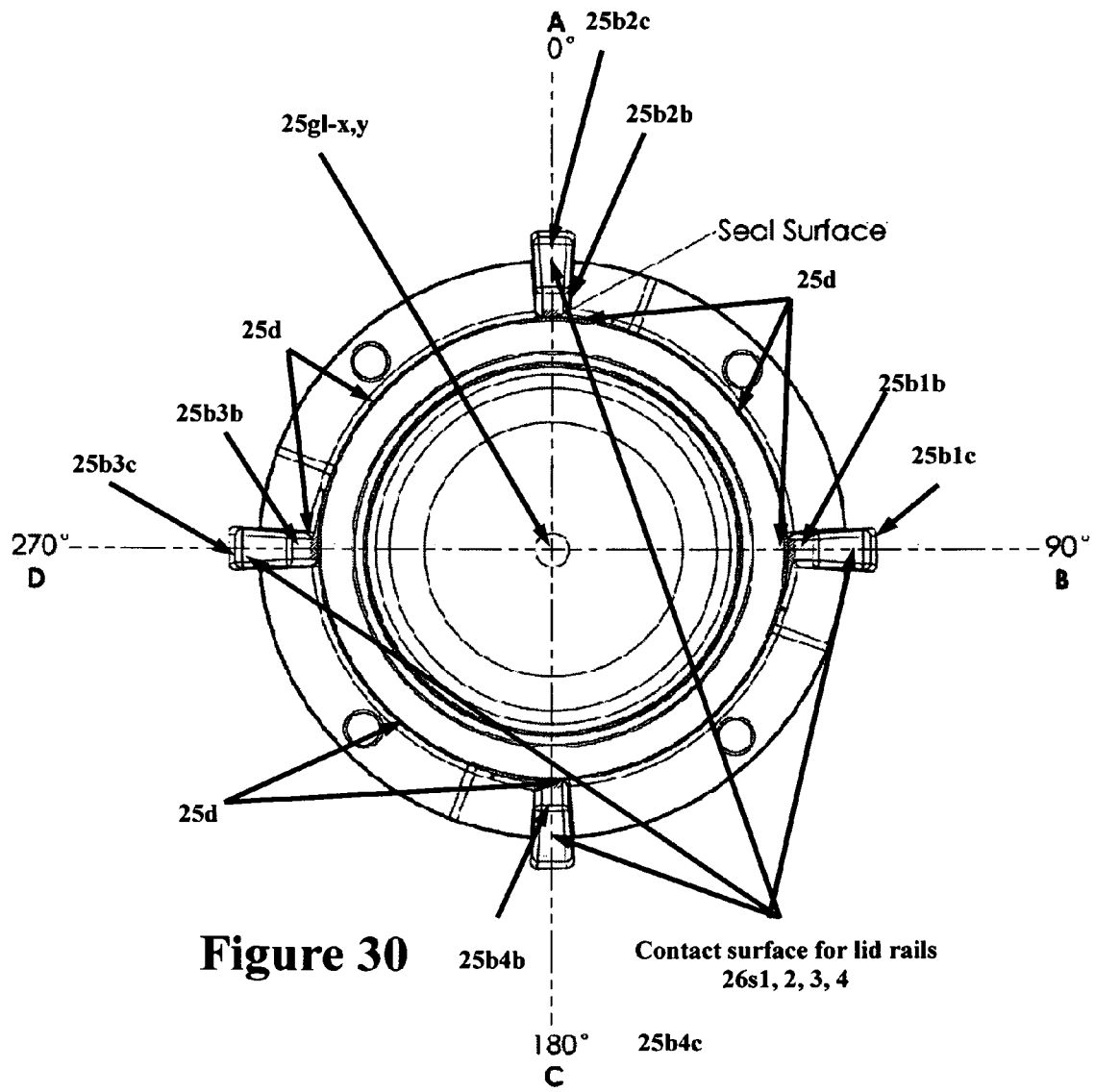
FIG. 30 is a top plan view of canister 25 showing structural arrangement of features of canister 25 which interface for the formation of seals between lid 26 and canister 25. During the bottle docking mode of operation, the said features of canister 25 also operate to form seals between a bottle, a bottle plug 65 and lid 26.

Turning to FIG. 30.

FIG. 30 is a top plan view of canister 25 and depicts annular sealing surface 25d marked by seven arrows and how the lid sealing surface 25d annularly relates to the center of canister 25 as shown at 25gl-x,y in so far as an x,y coordinate plane line AC crosses line BD at substantially the center of canister 25. This view also depicts how the inside angle of canister pillars 25b1b, 25b2b, 25b3b and 25b4b may function as a chamfer guide for guiding lid 26 and the inside edge of lid apertures 26h1, 26h2 26h3 and 26h4 to assist registration of lid 26 and canister 25 to properly seal canister sealing surface 25d with lid seal 26o. In addition, canister pillar outside surface angle 25b1c, 25b2c, 25b3c and 25b4c of canister pillars 25b1, 25b2, 25b3 and 25b4 also function as outwardly facing chamfer guides to assist with registration of lid 26 and canister 25 whereas the said outwardly facing chamfer guides interface with the outside edges of lid apertures 26h1, 26h2, 26h3 and 26h4 to guide and register lid 26 and canister 25. It is also contemplated that canister seal 25d and lid seal 26o are properly registered and aligned for sealing. Both horizontal and vertical registration between lid 26 and canister 25 are assisted so that alignment and sealing of lid seal 26o of lid 26 and canister seal 25d of canister 25 are engaged in such alignment and registration.

Turning to FIG. 31.

FIG. 31 is a side elevation blow up cutaway view of the top plan view of the assembly of lid 26 and canister 25 along the cutaway arrows shown at the left of FIG. 31, to depict the manner in which locking cap 27a may reside within lid 26 through lid lock hole 26i to contact canister 25. In this view the rotational relationship between lid 2 and canister 25 is such that lid lock hole 26i is not centered over canister lock holes 25a1, 2, 3, or 4. This structuration occurs while canister 25 and lid 26 are not in a fully sealed and operational relationship.

Turning to FIG. 32.

FIG. 32 is a side elevation blow up cutaway view of the top plan view of the assembly of lid 26 and canister 25 along the cutaway arrows shown at the left of FIG. 32 whereby the rotational relationship between lid 26 and canister 25 is in a fully sealed position which aligns lid lock hole 26i with at least one of the four canister lid lock holes 25a1, 2, 3, or 4 such that lid lock cap 27a may be directed downwardly through the centered holes in that lid 26 and canister 25 may be rotationally locked by interference fit of cap 27a.

Turning to FIG. 33.

FIG. 33 is a side elevation blow up view of the top plan view of the assembly of lid 26 and canister 25 along the cutaway arrows shown to the left of FIG. 33 which is the same disclosure as FIG. 32 with the modification that cap 27a is shown pressed down through lid lock hole 26i and at least one of canister lid lock holes 25a1, 2, 3 or 4. This rotationally stabilizes lid 26 and canister 25 by interference with cap 27a extending through holes in lid 26 and canister 25.

Figure 34:
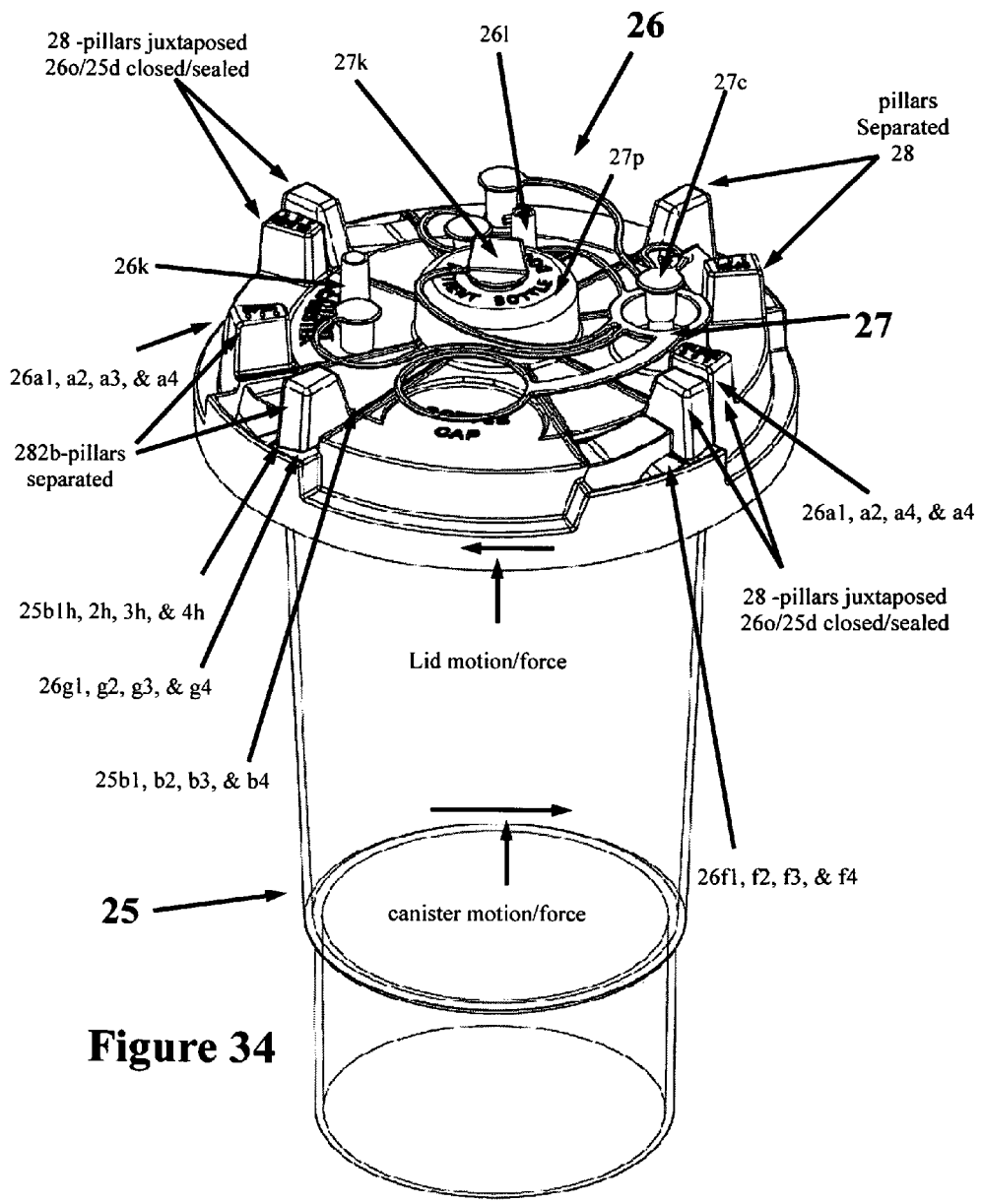
FIG. 34 is a top isometric view of a suction canister assembly of canister 25, lid 26 and member 27 in the mode of operation where bottle docking is not taking place because, for example a bottle is not available for docking. Lid port 26k is uncapped and open for connection to a patient suction tubing. Lid port 26l is uncapped and open and is available for connection to a conduit that is connected to a source of negative pressure. Lid port 26j is shown capped by member 27k. In this configuration, the suction canister 25 and associated system is in structuration of functioning as a non bottle docking system. The system is in a condition to draw waste under reduced pressure through a conduit and into the system as shown in FIG. 34. Also member 27b of capping member as shown in FIG. 18 is also shown plugging pour spout 26p of lid 26.

Turning to FIG. 34.

FIG. 34 is a top isometric view of the non-bottle docking assembly of canister 25, lid 26 and cap member 27 in a sealed structuration. Canister 25 of this figure is shown without a bottle docking capability whereas one feature of an embodiment is that system of the instant case operates a both a normal waste collection canister system when no bottles are desired to be docked and also operates as a waste collection bottle docking system. This system is functional as both a normal suction canister system and a bottle docking system. The canister in FIG. 34 remains useful in a facility in the event that the facility does not have an inventory of bottles for transformation into waste ingressing collection receptacles within the canister systems as shown in the instant case, which bottles are shown docked in the embodiments of the instant case showing bottle docking capability. FIG. 34 shows at 28 depicted in a plurality of places lid pillars and canister pillars are separated as depicted in two places and also in two places lid pillars and canister pillars are juxtaposed in two places to teach lid seal 26o and canister seal 25d are properly aligned, registered and sealed. Also shown are directional arrows depicting the clockwise motion potential of lid 26 and the counterclockwise motion potential of canister 25. The operation of sealing annular lid seal 26o with annular canister seal 25d is the operation of simply squeezing the lid pillars and canister pillars. The canister pillars that are intended to be squeezed to seal lid 26 and canister 25 at annular lid seal 26o and annular canister seal 25d is to place lid 26 onto canister 25 and simply squeeze or pinch the lid pillars having indicia "CLOSED" on 26c1 and 26c2 together with the canister pillars located in the direction of the arrows defined by the indicia "CLOSED". Similarly, when in this structuration lid pillar surface tops 26b1, 26b2 show indicia "OPEN" and to unseal seals 26o and 25d the process of squeezing lid pillars 26a2 and 26b2 together with the canister pillars shown in the direction of the "OPEN" arrows on the surfaces of lid pillars 26b2 and 26a2. The operation of unsealing canister seal 25d from lid seal 26o is to squeeze together lid pillars and canister pillars being shown as separated depicted by 28 marked twice in FIG. 34. The squeezing together of lid pillars and canister pillars as depicted twice as 28 cause the effect of canister pillar outside bottom surface 25b1h, 25b2h, 25b3h and 25b4h to ascend upwardly with respect to lid 26 and to ride up the lid/canister compression and sealing ramp of 26f1, 26f2, 26f3 and 26f4 to the extent that 25b1h, 25b2h, 25b3h and 25b4h ride up to and onto the canister pillar sealing surfaces 26g1, 26g2, 26g3 and 26g4. The movement of pillars depicted at 28 causes the sealing between lid 26 at 26o and canister 25 at 25d. Also seen in FIG. 34 is the lid pillars 26a1, a2, a3 and a4 as well as canister pillars 25b1, b2, b3 and b4. Also shown in this view at 26k is a suction tubing connection port for the connection of a patient suction wand and or a suction tip as defined in the instant case for the purposes of drawing waste material into canister 25 under reduced pressure, but not limited to that. Also shown in this view is a vacuum tubing connection port 26l for the connection to a source of reduced pressure. A conduit connects the canister system to a source of waste material. It is understood that pillars positioned opposite, and, for example, pillars 26a1 and 25b1 are opposite pillars 26a3 and 25b3 and each of these pairs of pillars may be squeezed by one hand singularly to operate the system or they may be both squeezed simultaneously by two hands to operate the canister system. The same exists for the other opposing pillars. Pillars 26a2 and 25b2 are opposite pillars 26a4 and 25b4 and each of these pairs of pillars may be squeezed together by one hand singularly to operate the system or they may be both squeezed together simultaneously to operate the system. The forces required to operate the system are confined to the offsetting counter forces and do not operate to move the entire system. This is important whereas canister systems are often on wheels, or on IV poles which are on wheels, or are mounted on other non stationary equipment which is on wheels, or other moving and non stationary base support substrates, and the counter opposing forces directed rotationally between the lid 26 and the canister 25 are designed off set and neutralize laterally directed forces which may move the substrate holding devices. The instant case embodiments are designed to the extent that the counterclockwise and clockwise forces used to operate the systems of the instant case do generate unwanted laterally generated forces when lid 26 and canister 25 are properly operated. This keeps the canister system and whatever holds the canister system within a desired footprint spatially within in the environment for which it is used. The design of the instant case also prevents the undesired rotation of the entire system as a result of the counter forces being applied on the lid and canister pillars simultaneously. Also shown in this view capping are member 27k caps and seals the lid 26 center aperture 26j whereas there is no bottle to be docked in this embodiment whereas the tubing connector of bottle plug (not shown) is not necessarily to be activated in this scenario because there no bottle being docked in this embodiment scenario of FIG. 34. FIG. 34 shows an embodiment of the instant case being employed and a normal canister system embodying novel operating features.

Figure 35:
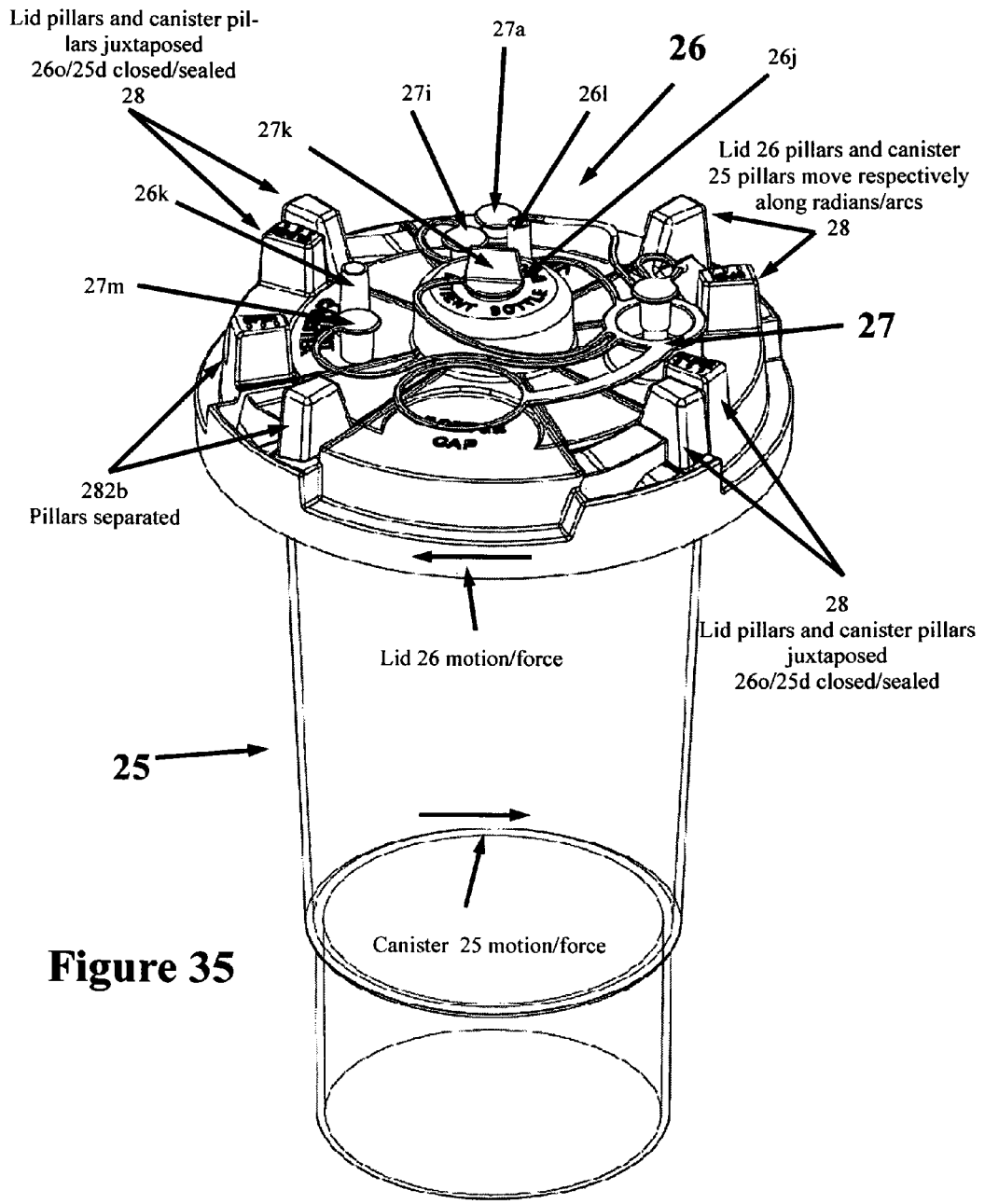
FIG. 35 is a top isometric view of FIG. 34 with locking member 27a pressed down locking the canister 25 and lid 26 into rotational security. This is accomplished by alignment of lid lock hole 26i of lid 26 and one of canister 25 lid locking holes 25a1, 2, 3, & 4 as shown in FIG. 33.

Turning to FIG. 35.

FIG. 35 is a top isometric view which is similar to FIG. 34 except that locking cap member 27a is pressed down through lid lock hole 26i of lid 26 and canister locking hole 25a1, a2, a3 and/or a4 of canister 25 as depicted in FIG. 33.

Figure 36:
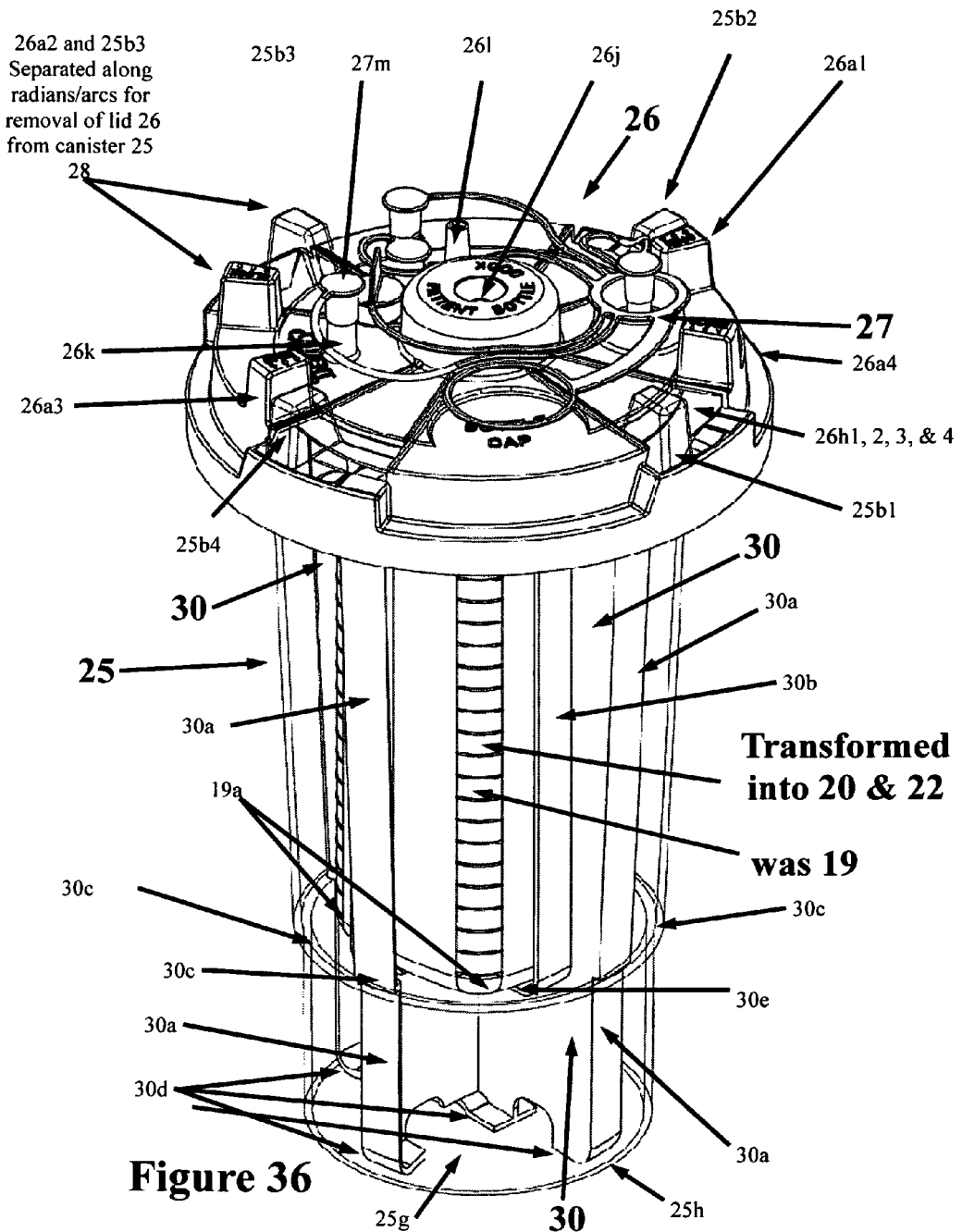
FIG. 36 is a top isometric view of an exemplary bottle docking mode of operation whereby bottle 19 is disposed in canister 25. Bottle 19 is supported by a stand 30. Bottle neck retains a plug 65 (not shown).

Turning to FIG. 36.

FIG. 36 is a top isomeric view of bottle docking system showing canister 25, lid 26, capping member 27, with the transformed bottle 19 shown and depicted as transformed into 20 and 22 as shown in FIGS. 13 14 and 15. Bottle 20 is conditioned for transformation into a waste ingressing receptacle and ultimately will dispose of waste material in a condition as shown in FIG. 15 being re-capped and sealed for the transfer of waste. Also it is shown at 25b1, 25b2, 25b3 and 25b4 that these canister pillars of canister 25 are projecting upwardly through lid apertures 26h1, 26h2, 26h3 and 26h4 for the placement of lid 26 onto canister 25 for the application of the counter rotational forces on lid pillars and canister pillars to seal lid seal 26o with canister seal 25d and to seal lid seal 26x with bottle plug 65 (not shown). Also seen in FIG. 36 is bottle holder 30. Bottle holder 30 is shown with a bottle resting surface 30e, a first indicia surface 30b for showing markings that represent how much collected material has been ingressed into bottle 19 which has been conditioned and transformed in preparation to become 20 and 22. Bottle holder 30 also shows surface 30a which is the surface closer to inside wall of canister 25. Surface 30a of bottle holder 30 is a surface which may have indicia markings for showing how much collection material has been ingressed into both the bottle 22 and the canister 25. Also shown in FIG. 36 is bottle holder 30 having bottoms depicted at 30d which rest inside canister 25 on its bottom surface 25g. 30c shows the stepped portion of the upright standards of bottle holder 30 which are located at the same location of the stepped portions along the annular wall of canister 25. Also shown in FIG. 36 is bottle bottom 19a which rests on bottle holder at 30e. It is understood that as lid pillars and canister pillars are urged for the purposes of sealing the bottle docking system, and as the canister pillars ascend up the lid ramps resulting in compression of lid 26 and canister 25 together, there is also a compression of the components of the bottle docking system such that canister inside bottom 25g and lid holder bottom 30d move together causing compression between the two, and, bottle 20 and holder surface 30e are moved together causing compression between the two, plug 65 and bottle 20 are moved together causing compression between the two, and lid 26 and canister 25 are moved together ultimately resulting in 1) sealing of canister 25 and lid 26, 2) sealing of lid 26 and bottle plug (not shown), sealing of bottle 20 and plug 65 (not shown). It is also noted that the height of lid ramps 26f1, 2, 3, & 4 is great enough so that all of the manufacturing stack up tolerances of the canister 25, lid 26, bottle 20 (in the conditioned and transformed assembly), and bottle holder 30, will all function to provide seals sufficient the contain and direct the reduced pressure of a vacuum draw path such that collection material may be ingressed into bottle 20. Similarly, when unsealing the system for disassembly, the height of unsealing ramps 25c1, 25c2, 25c3 and 25c4 as shown in FIG. 26 is sufficient to unseal canister 25 and lid 26. FIG. 36 also shows 26a2 and 25b3 separated along radians/arcs for removal of lid 26 from canister 25.

Figure 37:
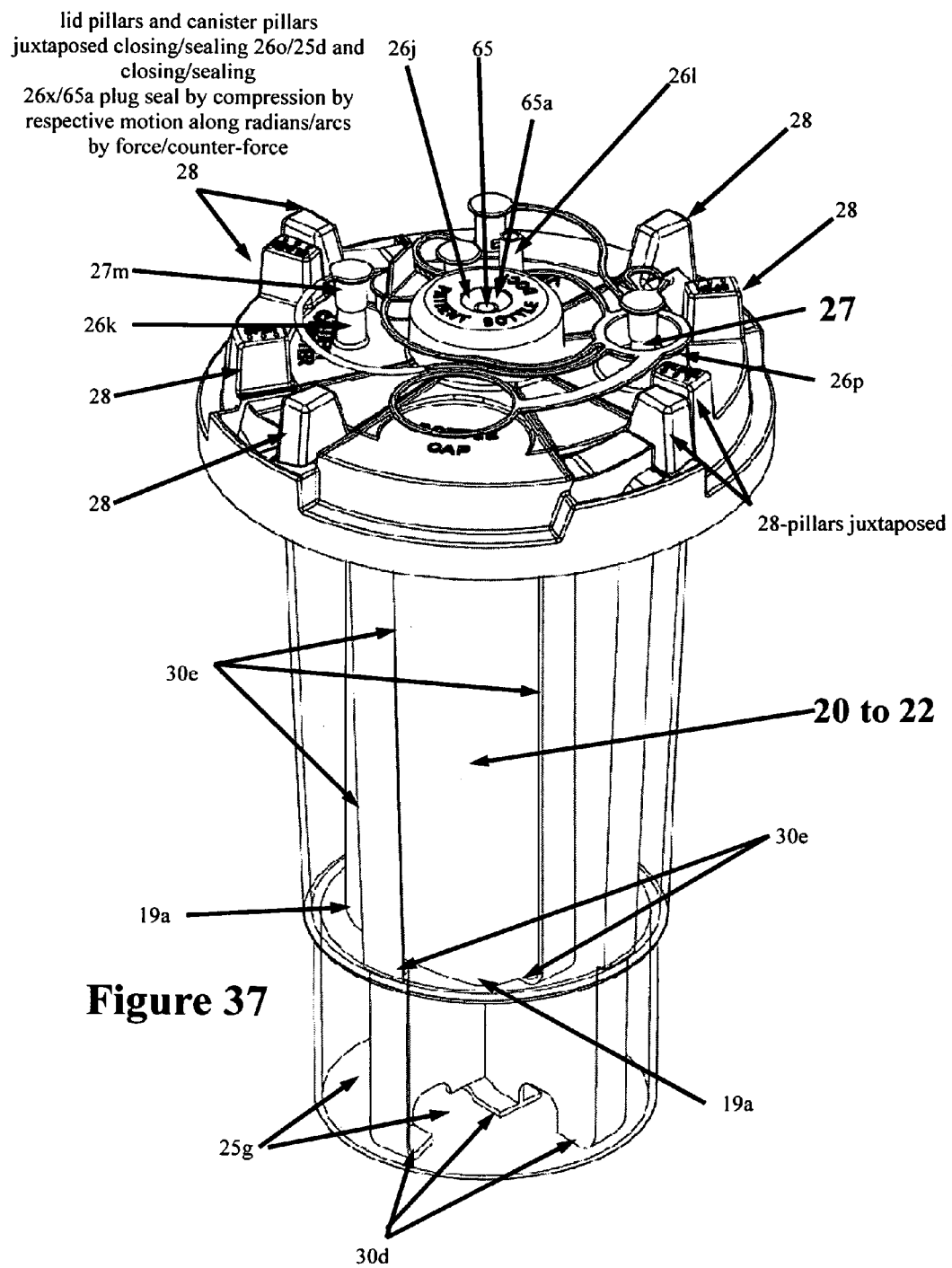
FIG. 37 is a top isometric view of an exemplary collection system in a bottle docking mode of operation.

Turning to FIG. 37.

FIG. 37 is a top isometric view showing lid pillars ad canister pillars juxtaposed closing and sealing lid seal 26o with canister seal 25d and closing and sealing lid seal 26x with bottle plug seal (not shown). Compression of the plug 65, lid 26, canister 25, bottle 20, bottle holder 30 has been accomplished to the extent sufficient to contain reduced pressure and direct the force of air drawn by a source of reduced pressure along a vacuum draw path which is substantial enough to be capable of ingressing drawn waste material from a source to ingress collection material into bottle 20 conditioning and transforming bottle 20, e.g. into a waste ingressing container. FIG. 37 also shows lid pillars and canister pillars juxtaposed closing and sealing 26o and 25d and closing and sealing 26x and 65a (not shown) by compression and respective motion along radians/arcs by force and or a counter-force. FIG. 37 also shows juxtaposed lid and canister pillars.

Figure 38:
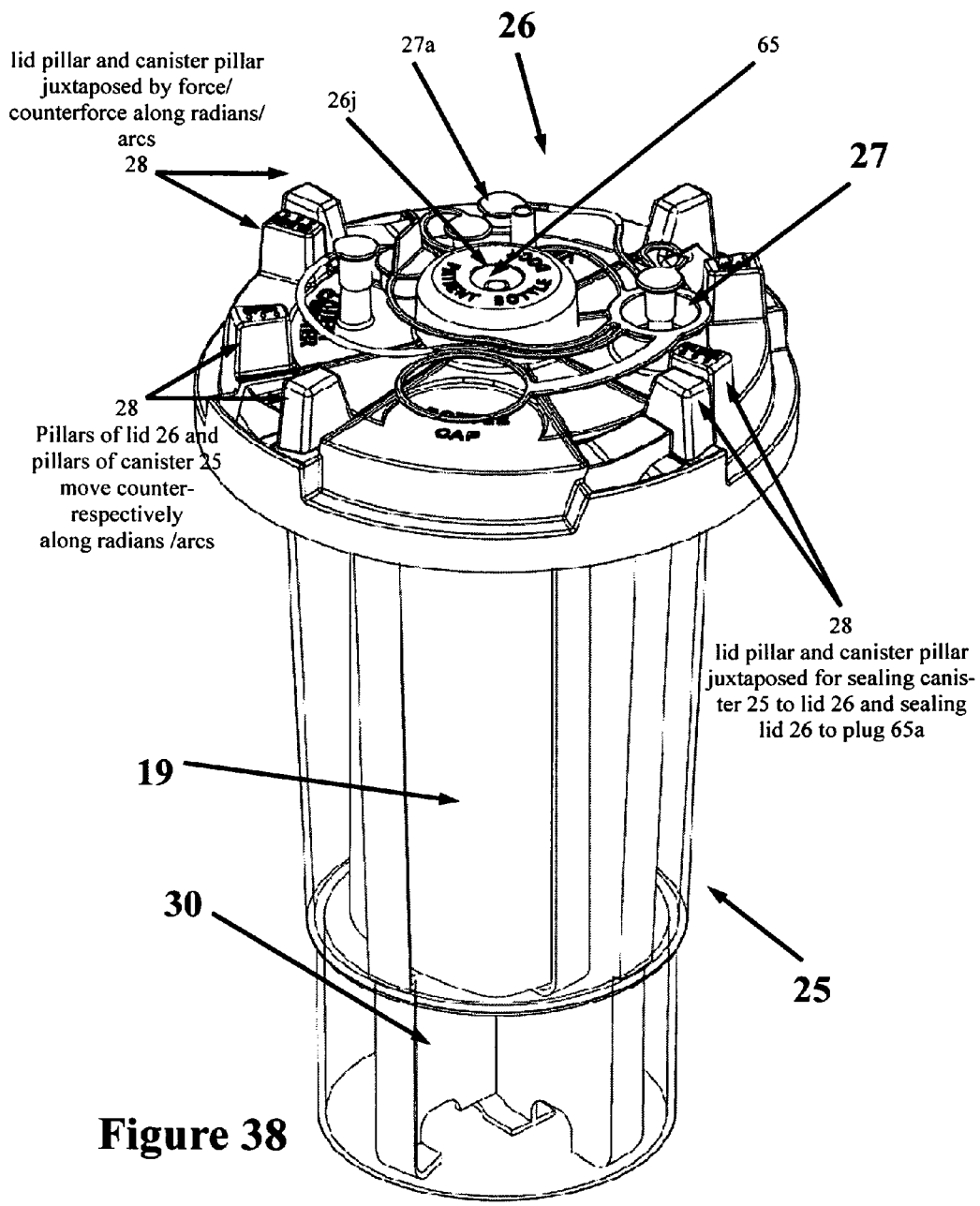
FIG. 38 is a top isometric view showing a bottle docking canister system wherein waste material has been drawn into bottle 19. Canister 25 and lid 26 are shown in a fully sealed and locked position.

Turning to FIG. 38.

FIG. 38 is a top isometric view of a bottle docking embodiment system showing cap 27a pressed down locking rotational movement between canister 25 and lid 26. Also seen at lid 26j is an aperture allowing for patient suction tubing to connect to a bottle plug (not shown) so a bottle plug and a suction tubing may be connected for creating a conduit flow control connection between a source of material to be collected and the ingressing of material to be drawn into bottle 20/22. FIG. 38 shows lid pillars and canister pillars juxtaposed by force and/or counterforce along radians/arcs. FIG. 38 also shows pillars of lid 26 and pillars of canister 25 move counter-respectively along radians/arcs. FIG. 38 also shows lid pillars and canister pillars juxtaposed for sealing canister 25 to lid 26 and sealing lid 26 to plug 65a (not shown).

Figure 39:
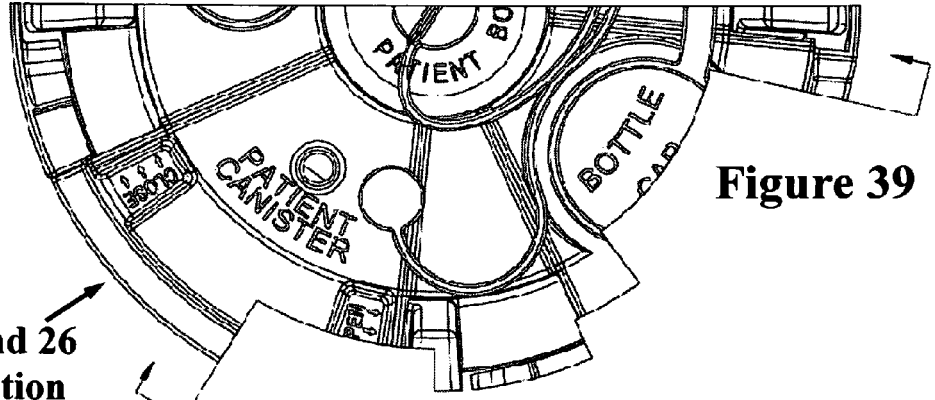
FIG. 39 is a top plan cutaway view of the sealing/closing assembly of lid 26 and canister 25 as depicted along the broken arrows.

Turning to FIG. 39.

Figure 40:
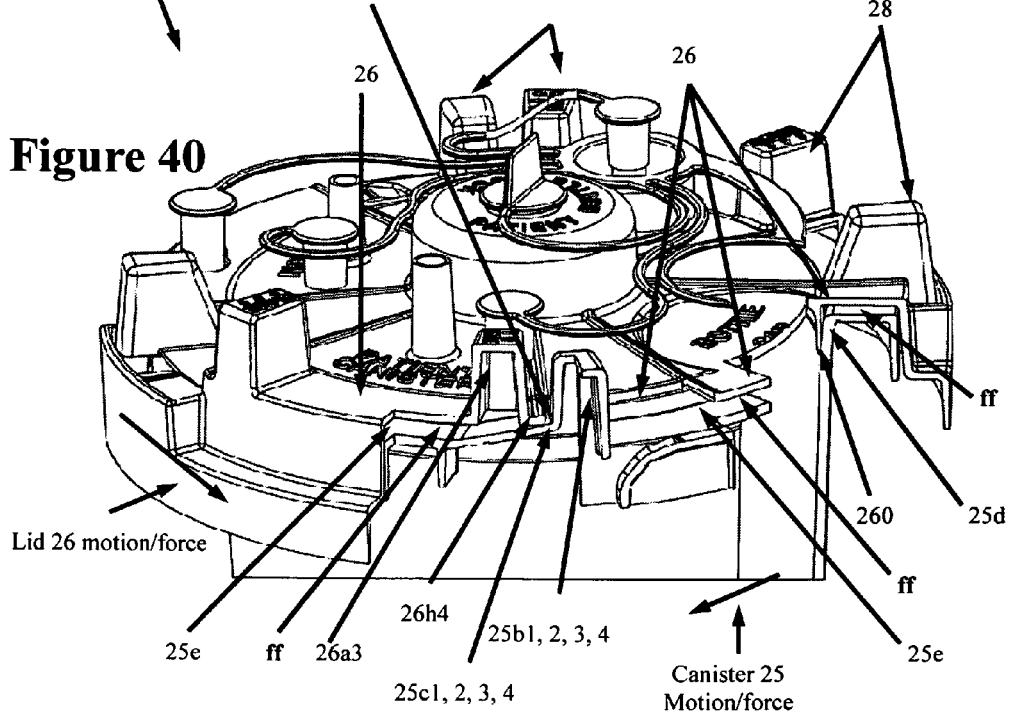
FIG. 40 is a top isometric cutaway view of FIG. 39 showing the relationship of canister 25 and lid 26 during its unsealing counter rotation. Canister and lid relationship 28 is marked in two places depicting the physical juxtaposition of the canister and lid pillar structuration motion.

FIG. 39 is a top plan cutaway view along the arrows of lid 26 and canister 25 operating at a certain rotational orientation as depicted in FIG. 40.

Turning to FIG. 40.

FIG. 40 is a top isometric view of the cutaway of canister 25 and lid 26 assembly of FIG. 39. Lid 26 motion force is shown in the counterclockwise direction. Canister 25 motion force is shown in the clockwise direction. ff defines a space/gap between lid 26 and canister 25 based on the rotational orientation between lid 26 and canister 25. Lid pillar 26a3 is shown rotationally abutted up against the counterclockwise facing side of canister pillar 25b3 and canister pillar 25b3 is abutted up against the clockwise facing edge of lid aperture 26h1 at 26e1. It is understood that lid 26 and canister 25 may be rotationally oriented in at least four separate orientations leaving the orientations of lid and canister features available to be in up to four possible initial spatial rotational arrangements. Also shown is lid aperture counterclockwise facing edges 26r1 and 26r2 having been urged up canister ramps 25c1, 2, 3, and/or 4 to effect ramp height as seen in FIG. 26 for unsealing the vacuum draw path that has contained the reduced pressure forces. The orientation of lid 26 and canister 25 in FIG. 40 produces the gap between lid 26 and canister 25 as shown by ff. Also shown is the orientation of lid seal 26o and canister seal 25d. FIG. 40 also shows lid pillars and canister pillars counter rotationally urged along radians/arcs. FIG. 40 also shows lid pillars and canister pillars allowed to separate counter-rotationally along radians/arcs.

Figure 41:
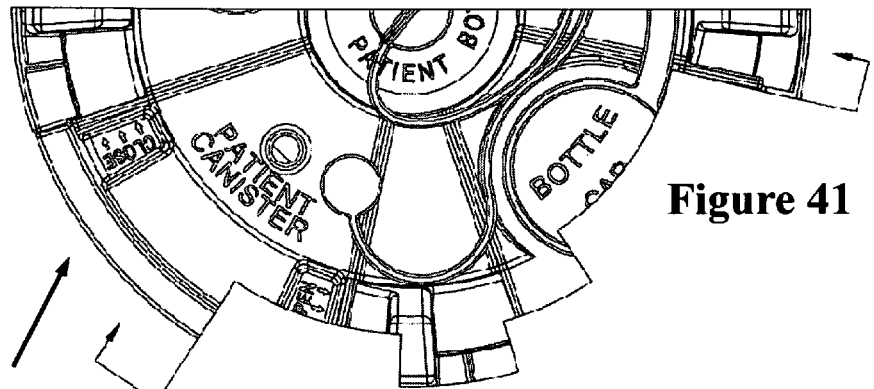
FIG. 41 is a top plan cutaway view of unsealing/opening of canister 25 and lid 26 as shown along the arrows.

Turning to FIG. 41.

Figure 42:
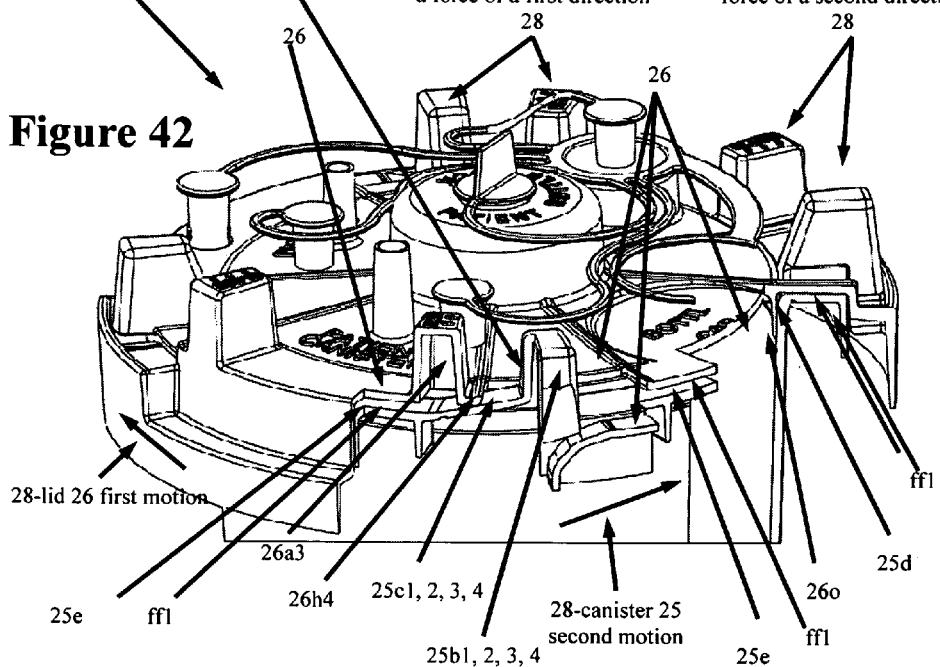
FIG. 42 is a top isometric view of FIG. 41 showing the relationship of canister 25 and lid 26. The progression of the relationship between lid 26 and canister 25 are shown going from FIGS. 46, 44, 42 and 40 depicting going between the sealed mode to the unsealed mode of lid 26 and canister 25. The progression of the relationship between lid 26 and canister 25 view in the reverse progress, e.g., from FIGS. 40-44, 42 and 46 show the opposite effect going between the unsealed mode to the sealed mode of operation.

FIG. 41 is a top plan cutaway view along the arrows of lid 26 and canister 25 showing operation at certain rotational orientations respectively between lid 26 and canister 25 as depicted in FIG. 42.

Turning to FIG. 42.

FIG. 42 is a top isometric cutaway along the arrows shown in FIG. 41 depicting the orientation of lid 26 and canister 25. Lid 26 is shown moving in a clockwise orientation and canister 25 is shown respectively being configured to be resistant to such a clockwise motion. Space/gap ff1 is shown as smaller than space/gap ff of FIG. 40 whereas the rotational orientation between lid 26 and canister 25 shows counterclockwise facing lid aperture edge at the bottom of lid pillar surfaces 26q1 and 26q2 are located at an intermediate portion of canister ramps 25c1, 2, 3, and or 4. FIG. 42 shows lid pillars and canister pillars allowed to separate counter-rotationally along radians/arcs by a force of a first direction. FIG. 42 also shows lid pillars and canister pillars counter-rotationally urged closer along radians/arcs by a force of a second direction.

Figure 43:
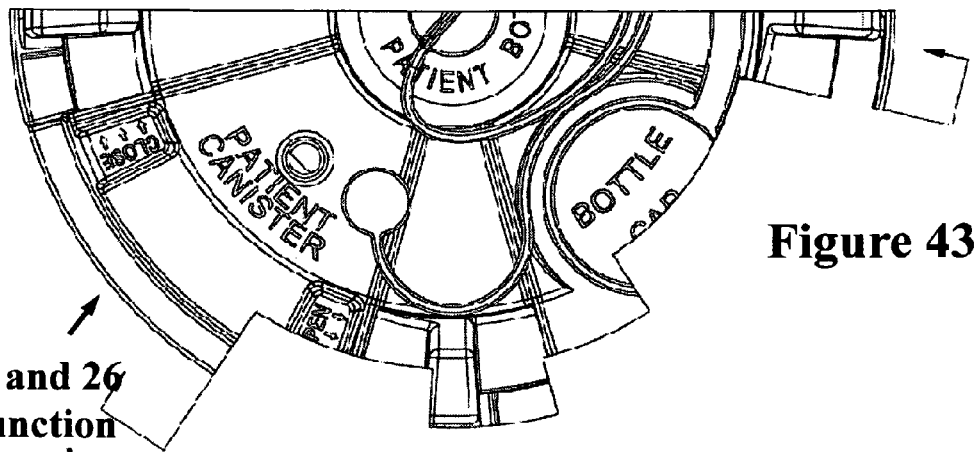
FIG. 43 is a top plan view of a cutaway of canister 25 and lid 26 as shown in FIG. 44 depicted by the arrows.

Turning to FIG. 43.

Figure 44:
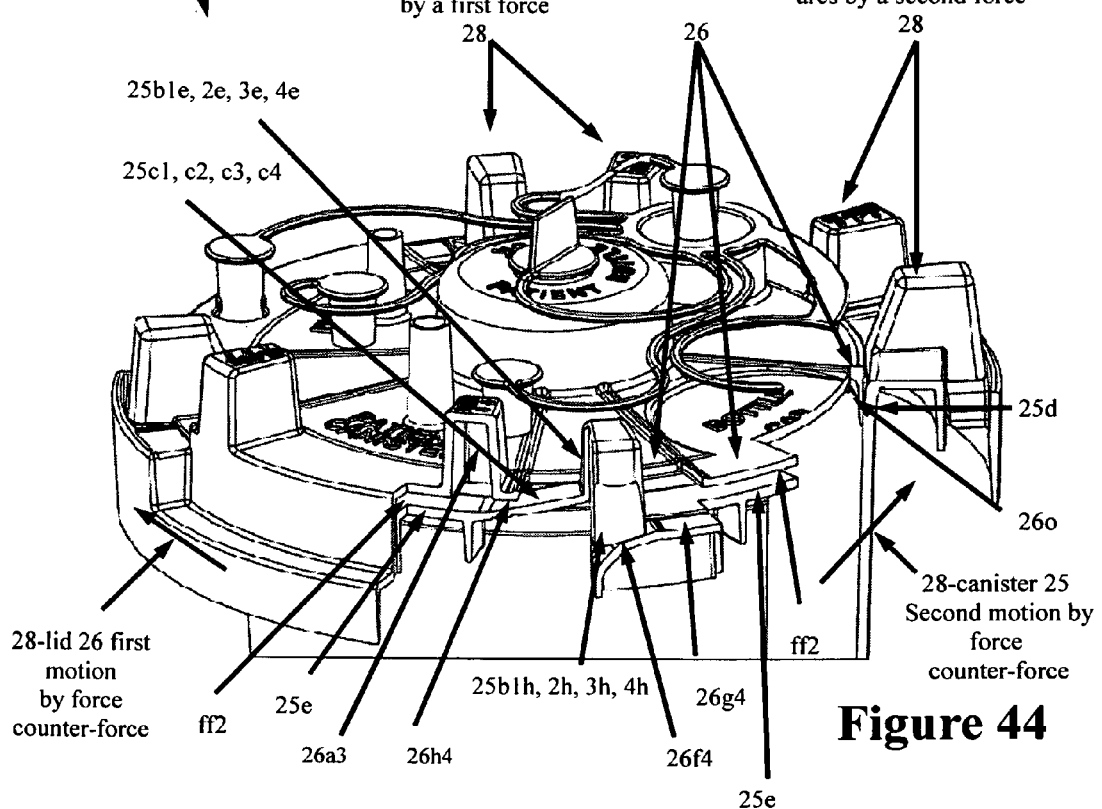
FIG. 44 is a top isometric view of the cutaway of FIG. 43 showing the counter motion between canister 25 and lid 26 to a greater extent operating to seal canister 25 to lid 26 and lid 26 to plug 65 (not shown) sealing having been established to create a reduced pressure so that waste material may be drawn into bottle 19 (or canister 25 in the event a bottle is not docked within the system.

FIG. 43 is a top plan cutaway view along the arrows of lid 26 and canister 25 showing operation at certain rotational orientation respectively between lid 26 and canister 25 as depicted in FIG. 44.

Turning to FIG. 44.

FIG. 44 is a top isometric cutaway view of lid 26 and canister 25 operation as seen in FIG. 43. FIG. 44 shows space/gap ff2 being smaller than that of ff1 as shown in FIG. 42. Canister seal 25d and lid seal 26o are shown sealed to a greater extend that that shown in FIG. 42. The bottom of lid pillar surface 26q1 and 26q2 which represent the counter clockwise facing edge of lid apertures 26h4, and 26h2 are seen further down the canister ramps 25c1, 25c2, 25c3 and or 25c4 than as shown in FIG. 42 depending upon which rotational orientation the lid 26 and canister 25 are oriented in with respect to each others rotational orientation. FIG. 44 also shows lid pillars ad canister pillars allowed to separate counter-rotationally along radians/arcs by a first force. FIG. 44 also shows lid pillars and canister pillars counter-rotationally urged closer together along radians/arcs by a second force. FIG. 44 also shows lid 26 in first motion which is a motion opposed to a counter force. FIG. 44 also shows canister 25 in second motion which is a motion opposed to a separate counter force.

Figure 45:
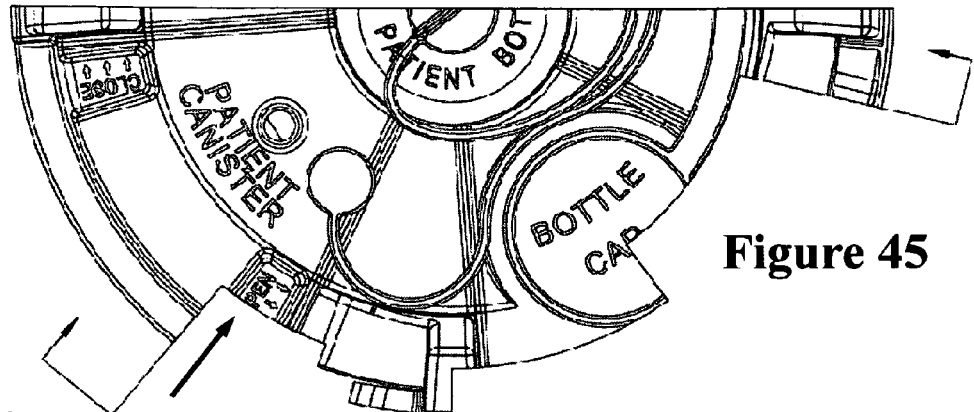
FIG. 45 is a top plan view of canister 25 and lid 26 relationship showing a cutaway of canister 25 and lid 26 along the arrows.

Turning to FIG. 45.

Figure 46:
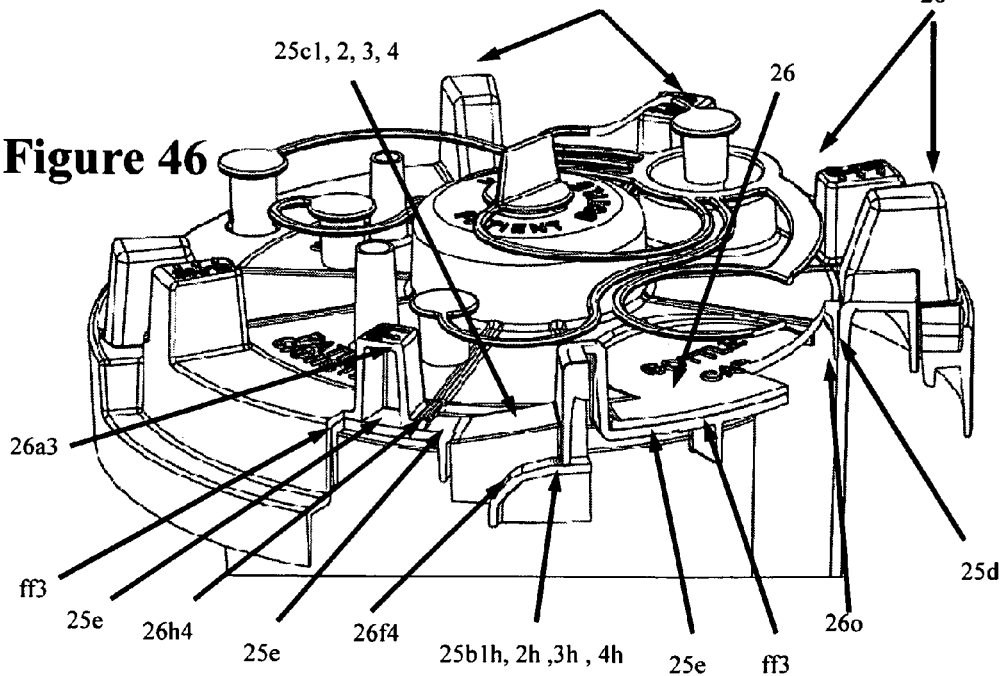
FIG. 46 is a top isometric view of cutaway of FIG. 45 depicting canister 25 and lid 26 shown in a fully sealed configuration.

FIG. 45 is a top plan cutaway view along the arrows of lid 26 and canister 25 showing operation at certain rotational orientation respectively between lid 26 and canister 25 as depicted in FIG. 46.

Turning to FIG. 46.

FIG. 46 is a top isometric cutaway view along the arrows shown in FIG. 45. FIG. 46 shows space/gap ff3 as being closed between lid 26 and canister 25 which results in lid seal 26o and canister seal 25d fully sealed by rotational orientation between lid 26 and canister 25. FIG. 46 shows separated lid pillars 26 and canister pillars 25 may be move respectively along radians/arcs. FIG. 46 also shows juxtaposed lid pillars 26 and canister pillars 25 may be moved respectively along radians/arcs. FIG. 46 also shows canister pillar bottoms 25b1h, 25b2h, 25b3h and 25b4h are positioned on lid ramps 26g1, 26g2, 26g3 and 26g4.

What is claimed is:

1. A supply chain method comprising,
   a) egressing a material from a container,
   b) retaining said container inside a canister, a reduced pressure force configured to be egressed out of said container and drawn out of a space outside said container within said canister, said space configured to form a portion of a draw path, said draw path includes a lid having at least one upwardly projecting unitarily formed pillar and said canister having at least one upwardly projecting unitarily formed pillar,
   c) moving said lid pillar towards said canister pillar forms a seal and allows said reduced pressure force to be drawn through said space and towards a source of said reduced pressure.
2. A method of claim 1 comprising,
   d) applying said reduced pressure force on the inside of said canister.
3. A method of claim 1 comprising,
   d) applying said reduced pressure force on the outside of said container.
4. A method of claim 1 comprising,
   d) applying said reduced pressure force on the inside of said container and the inside of said canister.
5. A method of claim 1 comprising,
   d) applying said reduced pressure force on the inside of said canister, outside of said container and the inside of said container.
6. A method of claim 1 comprising,
   d) drawing said reduced pressure force along the inside of said canister.
7. A method of claim 1 comprising,
   d) drawing said reduced pressure force along the outside of said container.
8. A method of claim 1 comprising,
   d) drawing said reduced pressure force along the inside of said container.
9. A method of claim 1 wherein rotational engagement between said canister and said lid in part provides said seal.
10. A method of claim 1 comprising,
    d) connecting a conduit to said lid, said conduit being configured to egress said force out of said space said reduced pressure force configured to ingress air into said container.
11. A method of claim 1 wherein said reduced pressure force includes air.
12. A method of claim 11 comprising,
    d) ingressing said air into said container along a second conduit.
13. A supply chain method of claim 12 wherein said air is contained in part by the inside of said container.
14. A supply chain method comprising,
    a) egressing a material from a container,
    b) retaining said container inside a canister, a seal between a lid and said canister, establishes flow of a vacuum force through a space between said container within said canister located along a draw path between a vacuum source and a source of waste material, said space being configured to contain the flow of a vacuum draw force, said vacuum draw force being applied on the inside of said container, said vacuum draw force being adapted to be drawn away from said canister,
    c) moving a lid pillar away from a canister pillar causes separation of said lid and said canister.
15. A method of claim 14 comprising,
    d) applying said force on the inside of said canister.
16. A method of claim 14 comprising,
    d) applying said force on the outside of said container.
17. A method of claim 14 comprising,
    d) applying said force on the inside of said container and the inside of said canister.
18. A method of claim 14 comprising,
    d) applying said force on the inside of said canister, outside of said container and the inside of said container.
19. A method of claim 14 comprising,
    d) drawing said force along the inside of said canister.
20. A method of claim 14 comprising,
    d) drawing said force along the outside of said container.
21. A method of claim 14 comprising,
    d) drawing said force along the inside of said container.
22. A method of claim 14 comprising,
    d) providing rotational engagement between said canister and said lid.
23. A method of claim 14 comprising,
    d) connecting a conduit to said lid, said conduit being configured to egress said force out of said space, said force being configured to ingress air into said container.
24. A method of claim 14 wherein said force includes air.
25. A method of claim 14 comprising,
    d) ingressing said air into said container along a second conduit.
26. A method of claim 14 wherein said force is configured to be contained in part by the inside of said container, said force being configured to emanate from said vacuum source.
27. A supply chain method comprising,
    a) egressing a material from a container,
    b) retaining said container inside a canister, a draw path configured to extend away from said container, said draw path to include a reduced pressure force being drawn along a conduit away from a space located outside said container within said canister, said draw path configured at least in part by a seal between a lid and said canister, said seal co-acting at least in part with a source of said reduced pressure, said draw path, said container, said canister and said lid to egress and ingress said reduced pressure force out of and into said space, c) applying said lid to said canister by a plurality of unitarily formed canister pillars configured to pass through a plurality of correspondingly located lid apertures to form said space, d) moving said plurality of canister pillars toward a plurality of lid pillars allows said reduced pressure to flow into and out of said space.

28. A method of claim 27 comprising, e) applying said force on the inside of said canister.

29. A method of claim 27 comprising, e) applying said force on the outside of said container.

30. A method of claim 27 comprising, e) applying said force on the inside of said container and the inside of said canister.

31. A method of claim 27 comprising, e) applying said force on the inside of said canister, outside of said container and the inside of said container.

32. A method of claim 27 comprising, e) drawing said force along the inside of said canister.

33. A method of claim 27 comprising, e) drawing said force along the outside of said container.

34. A method of claim 27 comprising, e) drawing said force along the inside of said container.

35. A method of claim 27 comprising, e) providing rotational engagement between said canister and said lid.

36. A method of claim 27 comprising, e) connecting a conduit to said lid, said conduit being configured to egress said force out of said space, said force being configured to ingress air into said container toward a source of said force.

37. A method of claim 27 wherein said force includes air.

38. A method of claim 37 comprising, e) ingressing said air into said container along a second conduit.

39. A method of claim 38 wherein said force is configured to be contained in part by the inside of said container, said force being configured to emanate from said source.

* * * * *

UNITED STATES PATENT AND TRADEMARK OFFICE
CERTIFICATE OF CORRECTION

PATENT NO. : 8,955,557 B2
APPLICATION NO. : 13/068012
DATED : February 17, 2015
INVENTOR(S) : Jack W. Romano et al.

It is certified that error appears in the above-identified patent and that said Letters Patent is hereby corrected as shown below:

In the Specification

1) Column 2, line 67: delete "time" and insert --times-- in its place to read "many times the"...
2) Column 3, line 61: delete "container" and insert --containers-- to read "containers are"...
3) Column 4, line 1: delete "purchase" and insert --purchased-- to read "is purchased to"...
4) Column 4, lines 54-55: insert --a-- between -such- and -stackable- to read "such a stackable"...
5) Column 5, line 11: delete "that" and insert --than-- to read "greater than the"... (2nd occurrence)
6) Column 5, line 39: delete "system" between -the- and -bottle- to read "so the bottle dock"...
7) Column 6, line 15: delete "the" between -for- and -product- to read "for product transfer"...
8) Column 6, line 26: delete "close" and insert --closed-- to read "producing closed top"...
9) Column 8, line 16: delete the second "and" and insert --as-- to read "advantages as disclosed"...
10) Column 9, line 40: insert --a-- between -pour- and -solution- to read "pour a solution"...
11) Column 14, line 35: delete "an" and insert --and-- to read "eliminated, and the disposal"...
12) Column 15, line 3: delete "show's" between -shows- and -a- to read "FIG. 8 shows a new"...
13) Column 15, line 55: delete "egress" and insert --egressed-- to read "has egressed out"...
14) Column 18, line 13: insert --)-- at the end of the line to read "within the system.)"...
15) Column 18, line 29: delete "garage" and insert --garbage-- to read "as garbage into"...
16) Column 19, line 1: delete "of" and insert --or-- to read "facility or a different"...
17) Column 19, line 45: delete "co" between -consumption- and -containers- to read "consumption containers"...
18) Column 19, line 46: delete "the" between -basis- and -as- to read "basis as an"...
19) Column 20, line 32: delete "placed" and insert --places-- to read "three places of"...
20) Column 21, line 10-11: delete "a" and insert --an-- at the end of the line to read "has an overabundance"...
21) Column 22, line 8: delete "conduit" and insert --Conduit-- to read "bottle 19. Conduit 23"...
22) Column 23, line 9: delete "and" between -36- and -D- to read "and 36 D at 270"...
23) Column 25, line 11: delete "at" and insert --as-- to read "seen as F"...
24) Column 25, line 43: delete "and" and insert --an-- at the beginning of the line to read "an arc shown"...

Signed and Sealed this
Fifth Day of May, 2015

Michelle K. Lee
*Director of the United States Patent and Trademark Office*

25) Column 25, line 52: delete "a" and insert --an-- to read "defines an arc"...
26) Column 25, line 54: delete "to" to read "substantially counterclockwise"...
27) Column 26, line 1: insert --of-- between -surface- and -lid- to read "surface of lid"...
28) Column 26, line 14: insert --the-- between -to- and -clockwise- to read "to the clockwise"...
29) Column 26, line 23: insert --and-- between -59- and -begins- to read "59 and begins"...
30) Column 27, line 28: delete "that" and insert --the-- to read "is the system"...
31) Column 27, line 28: insert --as-- between -operates- and -a- to read "operates as a"...
32) Column 27, line 63: delete "as" and insert --at-- to read "twice at 28"... (2nd occurrence)
33) Column 28, line 31: insert --to-- between -designed- and -off- to read "designed to off set"...
34) Column 28, lines 42-43: insert --is how-- between -view- and -capping- to read "view is how capping"...
35) Column 28, lines 42-43: delete "are member" and insert --members-- to read "capping members 27K"...
36) Column 28, line 46: delete "to be" between -necessarily- and -activated- to read "necessarily activated"...
37) Column 28, line 57: insert --a-- between -of- and -bottle- to read "of a bottle"...
38) Column 29, line 46: delete "ad" at the end of the line to read "pillars and"...
39) Column 31, line 3: delete "extend that" and insert --extent than-- to read "greater extent than"...

In the Claims

40) Column 32, line 24: delete "," between -canister- and -establishes- to read "canister establishes"...